(12) United States Patent
Wendel et al.

(10) Patent No.: US 9,624,491 B2
(45) Date of Patent: Apr. 18, 2017

(54) METHODS AND COMPOSITIONS FOR THE DETECTION AND TREATMENT OF CANCER INVOLVING MIRNAS AND MIRNA INHIBITORS AND TARGETS

(75) Inventors: Hans-Guido Wendel, New York, NY (US); Andrew L. Wolfe, New York, NY (US); Konstantinos John Mavrakis, New York, NY (US); Elisa Oricchio, New York, NY (US); Adolfo A. Ferrando, New York, NY (US); Kim De Keersmaecker, Lueven (BE); Teresa Palomero, New York, NY (US); Franki Speleman, Ghent (BE); Pieter Van Vlierberghe, Ghent (BE)

(73) Assignees: Memorial Sloan Kettering Cancer Center, New York, NY (US); Universiteit Gent, Ghent (BE); Columbia University, New York, NY (US)

( * ) Notice: Subject to any disclaimer, the term of this patent is extended or adjusted under 35 U.S.C. 154(b) by 0 days.

(21) Appl. No.: 13/581,032

(22) PCT Filed: Feb. 28, 2011

(86) PCT No.: PCT/US2011/000365
§ 371 (c)(1),
(2), (4) Date: Nov. 27, 2012

(87) PCT Pub. No.: WO2011/106104
PCT Pub. Date: Sep. 1, 2011

(65) Prior Publication Data
US 2013/0064810 A1    Mar. 14, 2013

Related U.S. Application Data

(60) Provisional application No. 61/460,217, filed on Dec. 28, 2010, provisional application No. 61/339,072, filed on Feb. 26, 2010.

(51) Int. Cl.
| | | |
|---|---|---|
| *C12N 15/11* | (2006.01) | |
| *C12N 15/113* | (2010.01) | |
| *C12Q 1/68* | (2006.01) | |

(52) U.S. Cl.
CPC .......... *C12N 15/113* (2013.01); *C12Q 1/6809* (2013.01); *C12N 2310/113* (2013.01)

(58) Field of Classification Search
CPC ............... C12Q 2600/178; C12Q 1/68; C12Q 2600/158; C12N 15/113; G01N 33/5023
See application file for complete search history.

(56) References Cited

U.S. PATENT DOCUMENTS

| | | |
|---|---|---|
| 2005/0256072 A1 | 11/2005 | Aronin et al. |
| 2005/0261218 A1 | 11/2005 | Esau et al. |
| 2007/0072204 A1* | 3/2007 | Hannon et al. ............ 435/6 |
| 2009/0092974 A1* | 4/2009 | Davison et al. ............ 435/6 |
| 2009/0131356 A1 | 5/2009 | Bader et al. |
| 2009/0143326 A1 | 6/2009 | Obad et al. |
| 2010/0029003 A1 | 2/2010 | Bartel et al. |
| 2010/0286234 A1 | 11/2010 | Elmen et al. |

FOREIGN PATENT DOCUMENTS

| | | |
|---|---|---|
| WO | WO 2006/108718 | 10/2006 |
| WO | WO 2009/108866 | 9/2009 |
| WO | WO 2009/148631 | 12/2009 |
| WO | WO 2009/152300 | 12/2009 |
| WO | WO2010144485 | 12/2010 |

OTHER PUBLICATIONS

Wendel, HG et al (2004) Survival signalling by AKT and eIF4E in oncogenesis and cancer therapy Nature 428 (6980):332-337.
Weng, AP et al (2004) Activating mutations of NOTCH1 in human T cell acute lymphoblastic leukemia Science 306 (5694):269-271.
Weng, AP et al (2006) c-Myc is an important direct target of Notch1 in T-cell acute lymphoblastic leukemia/lymphoma Genes Dev 20(15):2096-2109.
Winandy, S et al (1995) A dominant mutation in the Ikaros gene leads to rapid development of leukemia and lymphoma Cell 83(2):289-299.
Xiao, C et al (2008) Lymphoproliferative disease and autoimmunity in mice with increased miR-17-92 expression in lymphocytes Nature Immunology 9(4):405-414.
Adams, JM et al (1985) The c-myc oncogene driven by immunoglobulin enhancers induces lymphoid malignancy in transgenic mice Nature 318(6046):533-538.
Aifantis, I et al (2008) Molecular pathogenesis of T-cell leukaemia and lymphoma Nat Rev Immunol 8(5):380-390 doi: 10.1038/nri2304.
Balgobind, BV et al (2008) Leukemia-associated NF1 inactivation in patients with pediatric T-ALL and AML lacking evidence for neurofibromatosis Blood 111(8):4322-4328.

(Continued)

*Primary Examiner* — Kate Poliakova-Georgantas
(74) *Attorney, Agent, or Firm* — Mark S. Cohen; Pearl Cohen Zedek Latzer Baratz LLP

(57) ABSTRACT

The present invention relates to microRNAs (miRNAs) which are associated with cancer, particularly including hematologic malignancies, and particularly T-cell acute lymphoblastic leukemia (T-ALL), and to the assessment and modulation thereof in the treatment and management of cancer. The present invention is directed to methods and compositions for diagnosing and treating cancer, particularly T-ALL, by modulating miRNAs, and the use of miRNAs and antagonists thereof, particularly antagomirs, for predicting and assessing response to treatment, in assays for isolating and selecting antagonists, and as compositions for the treatment and management of cancer. Methods and compositions are provided for treatment or alleviation of cancer, particularly T-ALL, with antagonists/antagomirs of miRNAs, particularly one or more of miR-19b, miR-20a, miR26, miR92, miR148 and miR223.

7 Claims, 29 Drawing Sheets

(56) References Cited

OTHER PUBLICATIONS

Baltimore, D et al (2008) MicroRNAs: new regulators of immune cell development and function Nat Immunol 9 (8):839-845.
Bartel, DP (2004) MicroRNAs:genomics, biogenesis, mechanism, and function Cell 116(2):281-297.
Bartel, DP (2009) MicroRNAs: target recognition and regulatory functions Cell 136(2):215-233.
Calin, GA et al (2004) MicroRNA profiling reveals distinct signatures in B cell chronic lymphocytic leukemias Proc Natl Acad Sci USA 191(32):11755-11760.
Chang, K et al (2006) Lessons from Nature: microRNA-based shRNA libraries Nature Methods 3(9):707-714.
Chen, Y et al (2010) Altered expression of MiR-148a and MiR-152 in gastrointestinal cancers and its clinical significance J Gastrointest Surg 14(7): 1170-1179 doi:.1007/s 11605-0 10-12022.
Dail, M et al (2010) Mutant Ikzf1, KrasG12D, and Notch1 cooperate in T lineage leukemogenesis and modulate responses to targeted agents Proc Natl Acad Sci USA 107(11):5106-5111.
Egle, A et al (2004) VavP-Bcl2 transgenic mice develop follicular lymphoma preceded by germinal center hyperplasia Blood 103(6):2276-2283.
Ellisen, LW et al (1991) Tan-1, the Human Homolog of the Drosophila Notch Gene, Is Broken by Chromosomal Translocations in T Lymphoblastic Neoplasms Cell 66(4):649-661.
Evan, GI et al (1992) Induction of Apoptosis in Fibroblasts by c-myc Protein Cell 69(1):119-128.
Friedman, RC et al (2009) Most Mammalian mRNAs Are Conserved Targets of microRNAs Genome Research 19 (1):92-105.
Garzon, R et al (2009) MicroRNAs in Cancer Ann Rev Med 60:167-179.
Griffiths-Jones, S (2003) miRBase: the microRNA sequence database Methods Mol Biol 342:129-138.
Hayashita Y et al (2005) A polycistronic microRNA cluster, miR-17-92, is overexpressed in human lung cancers and enhances cell proliferation Cancer Res 65(21):9628-9632.
He, L et al (2005) A microRNA polycistron as a potential human oncogene Nature 435(7043):828-833.
Huse, JT et al (2009) The PTEN-regulating microRNA miR-26a is amplified in high-grade glioma and facilitates gliomagenesis in vivo Genes Dev 23(11):1327-1337.
Johnson, SM et al (2005) RAS is regulated by the let-7 microRNA family Cell 120(5):635-647.
Klinakis, A et al (2006) Myc is a Notch1 Transcriptional Target and a Requisite for Notch1-induced Mammary Ttumorigenesis in Mice Proceedings of the National Academy of Sciences USA 103(24):9262-9267.
Krützfeldt, J et al (2005) Silencing of microRNAs in vivo with 'antagomirs' Nature 438(7068):685-689.
Krützfeldt, J et al (2007) Specificity, duplex degradation and subcellular localization of antagomirs Nucl Acids Res 35 (9):2885-2892.
Landais, S et al (2007) Oncogenic Potential of the miR-106-363 Cluster and Its Implication in Human T-Cell Leukemia Canc Res 67(12):5699-5707.
Landgraf, P et al (2007) A Mammalian microRNA Expression Atlas Based on Small RNA Library Sequencing Cell 129 (7):1401-1414.
Lewis, BP et al (2003) Prediction of Mammalian microRNA Targets Cell 115(7):787-798.
Li, QJ et al (2007) miR-181a Is an Intrinsic Modulator of T-cell Sensitivity and Selection Cell 129(1):147-161.
Lu, J et al (2005) MicroRNA expression profiles classify human cancers Nature 435(7043):834-838.
Lui, WO et al (2007) Patterns of known and novel small RNAs in human cervical cancer Cancer Res 67(13):6031-6043.
Marçais, A et al (2010) Genetic inactivation of Ikaros is a rare event in human T-ALL Leukemia Research 34 (4):426-429.
Maser, RS et al (2007) Chromosomally unstable mouse tumours have genomic alterations similar to diverse human cancers Nature 447(7147):966-971.

Mavrakis, KJ et al (2010) Genome-wide RNA-mediated Interference Screen Identifies miR-19 Targets in Notch-induced T-cell Acute Lymphoblastic Leukaemia Nature Cell Biology 12(4):372-379.
Mullighan, CG et al (2007) Genome-wide analysis of genetic alterations in acute lymphoblastic leukaemia Nature 446 (7137):758-764.
Olive, V et al (2005) miR-19 is a key oncogenic component of mir-17-92 Leukemia 19(11):2013-2016.
O'Neil, J et al (2007) FBW7 Mutations in leukemic cells mediate NOTCH pathway activation and resistance to γ-secretase inhibitors J Exp Med 204(8):1813-1824.
Paddison, PJ et al (2004) A resource for large-scale RNA-interference-based screens in mammals Nature 428 (6981):427-431.
Palomero, T et al (2006) Activating mutations in NOTCH1 in acute myeloid leukemia and lineage switch leukemias Leukemia 20(11):1963-1966.
Palomero, T et al (2006) NOTCH1 directly regulates c-Myc and activates a feed-forward-loop transcriptional network promoting leukemic cell growth Proc Natl Acad Sci Usa 103(48):18261-18266.
Pear, Ws et al (1996) Exclusive Development of T Cell Neoplasms in Mice Transplanted with Bone Marrow Expressing Activated Notch Alleles J Exp Med 183(5):2283-2291.
Petrocca, F et al (2008) E2F1-regulated microRNAs impair TGFbeta-dependent cell-cycle arrest and apoptosis in gastric cancer Cancer Cell 13(2):272-286.
Pezzolesi, Mg et al (2008) Differential expression of Pten-targeting microRNAs miR-19a and miR-21 in Cowden syndrome Am J Hum Genet 82(5):1141-1149.
Scherr, M et al (2007) Lentivirus-mediated antagomir expression for specific inhibition of miRNA function Nucl Acids Res 35(22):e149 (doi:10.1093/nar/qkm971).
Sun, L et al (1999) Expression of dominant-negative Ikaros isoforms in T-cell acute lymphoblastic leukemia Clin Cancer Res 5(8):2112-2120.
Thompson, B et al (2007) The SCFFBW7 ubiquitin ligase complex as a tumor suppressor in T cell leukemia J Exp Med 204(8):1825-1835.
Van Vlierberghe, P et al (2006) The cryptic chromosomal deletion del(11)(p12p13) as a new activation mechanism of LMO2 in pediatric T-cell acute lymphoblastic leukemia Blood 108(10):3520-3529.
Venturini, L et al (2007) Expression of the miR-17-92 polycistron in chronic myeloid leukemia (CML) CD34+ cells Blood 109(10):4399-4405.
Visone, R et al (2009) MiRNAs and cancer Am J Pathology 174(4):1131-1138.
Volinia, S et al (2006) A microRNA expression signature of human solid tumors defines cancer gene targets Proc Natl Acad Sci USA 103(7):2257-2261.
Han, M et al (2009) Abstract 3010: MiRNA-26 Plays Essential Role in Myocyte Survival and Hypertrophy by Regulating GATA4 Circulation 120:S732.
Inomata, M et al (2009) MicroRNA-17-92 down-regulates expression of distinct targets in different B-cell lymphoma subtypes Blood 113(2):396-402.
Isken, F et al (2006) Abstract 2231: Distinct Expression Patterns of Human microRNAs in Myeloid Differentiation and Acute Myeloid Leukemia Blood 108(11):632A.
Jones, MR et al (2009) Zcchc11-dependent uridylation of microRNA directs cytokine expression Nat Cell Biol 11 (9):1157-1163.
Mavrakis, KJ et al (2011) A cooperative microRNA-tumor suppressor gene network in acute T-cell lymphoblastic leukemia (T-ALL) Nat Genet 43(7):673-678.
Mavrakis, KJ et al (2011) Cooperative control of tumor suppressor genes by a network of oncogenic microRNAs Cell Cycle 10(17):2845-2849.
Sander, S et al (2009) Repressing the repressor: a new mode of MYC action in lymphomagenesis Cell Cycle 8 (4):556-559.

(56) References Cited

OTHER PUBLICATIONS

Van der Meulen, JC et al (2009) Abstract 1061: microRNA signatures in genetic subtypes of T-cell acute lymphoblastic leukemia Haematologica—The Hematology Journal 94(Suppl.2):427.

Vasilatou, D et al (2009) The role of microRNAs in normal and malignant hematopoiesis European Journal Haematology 84(1):1-16.

Wang, Y et al (2010) MicroRNAs expression signatures are associated with lineage and survival in acute leukemias Blood Cells Mol Ds 44(3):191-197.

\* cited by examiner

Figure 4
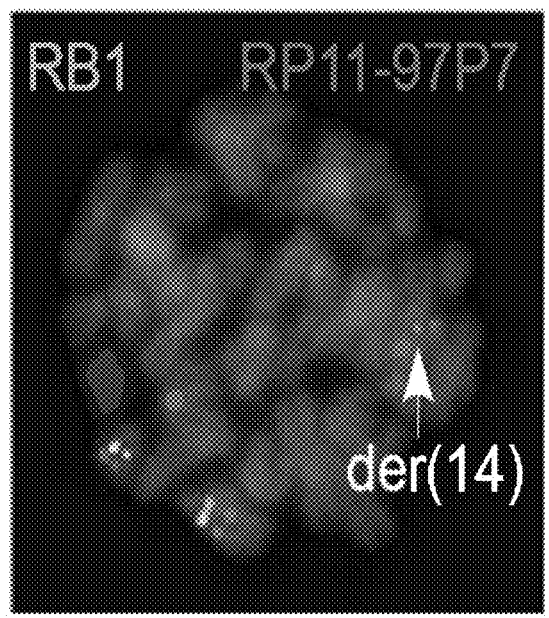
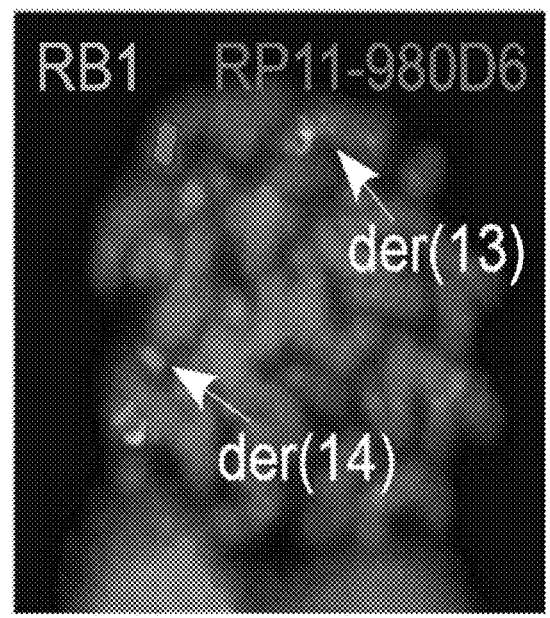

Figure 5
a
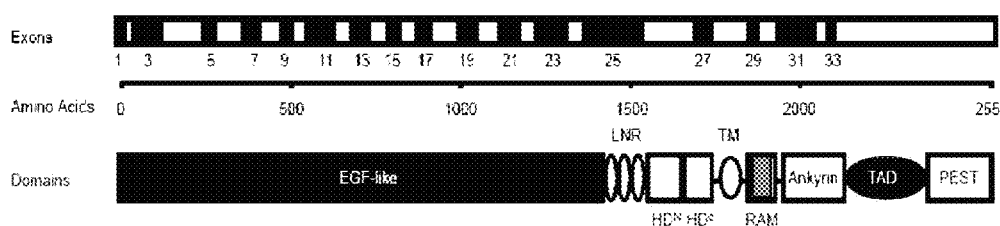
b
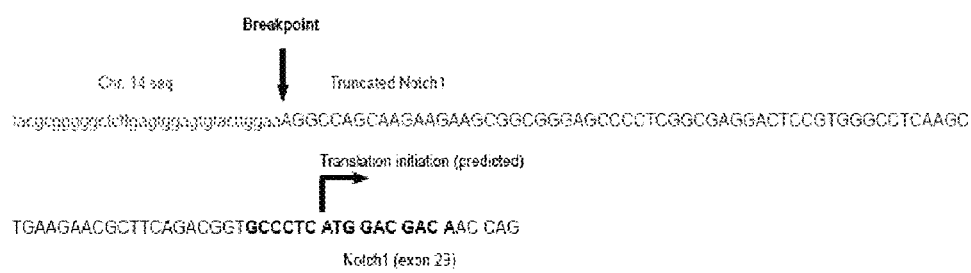
c
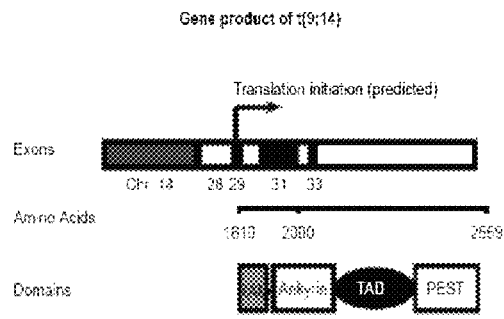

Figure 7
a
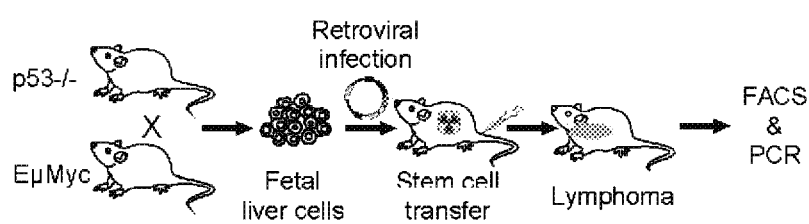
b
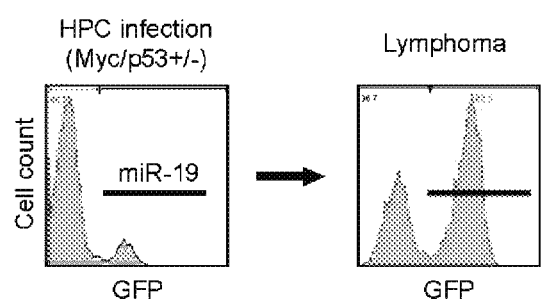
c
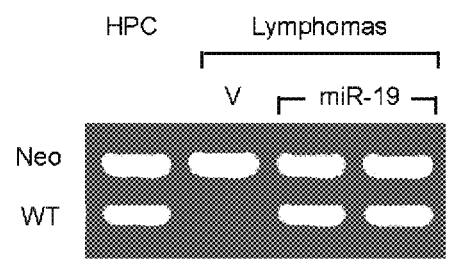

Figure 8
a
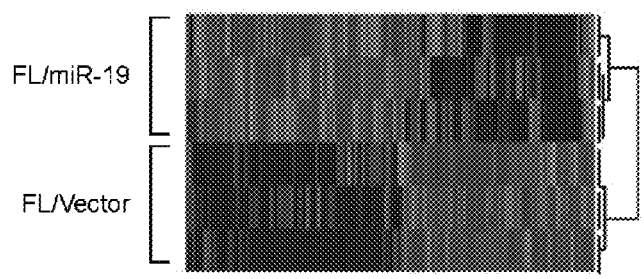
b
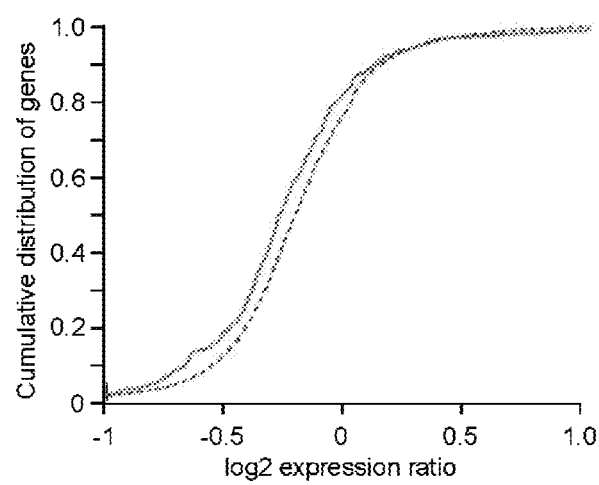
c
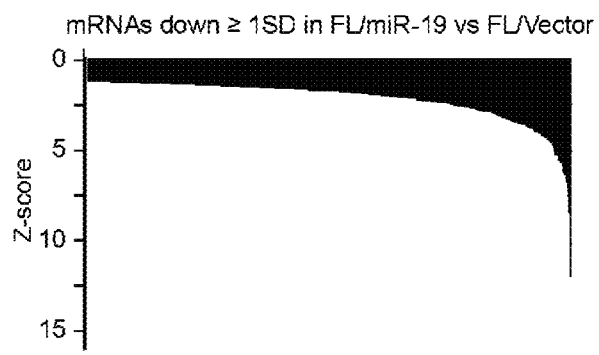

Figure 11
a
HUMAN miR-19 targets
(938 genes, including Dock5)
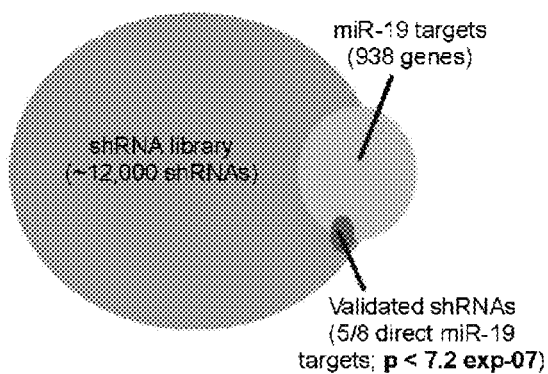
miR-19 targets
(938 genes)
shRNA library
(~12,000 shRNAs)
Validated shRNAs
(5/8 direct miR-19
targets; $p < 7.2\ exp\text{-}07$)
b
MURINE miR-19 targets
(744 genes, not including Dock5)
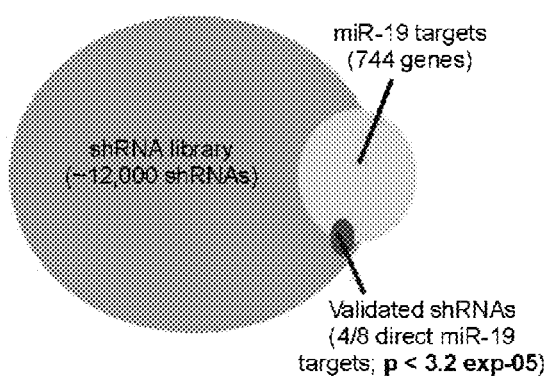
miR-19 targets
(744 genes)
shRNA library
(~12,000 shRNAs)
Validated shRNAs
(4/8 direct miR-19
targets; $p < 3.2\ exp\text{-}05$)

Figure 18
a
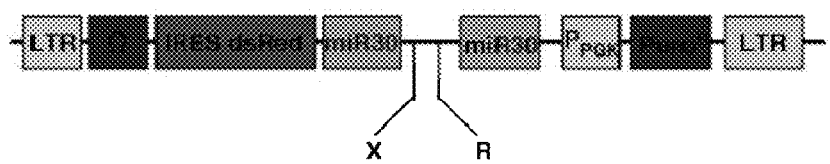
b
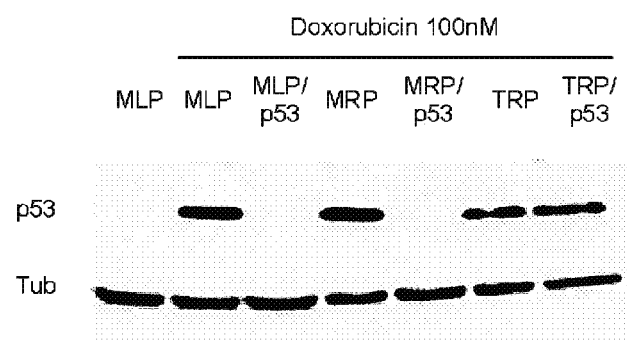
c
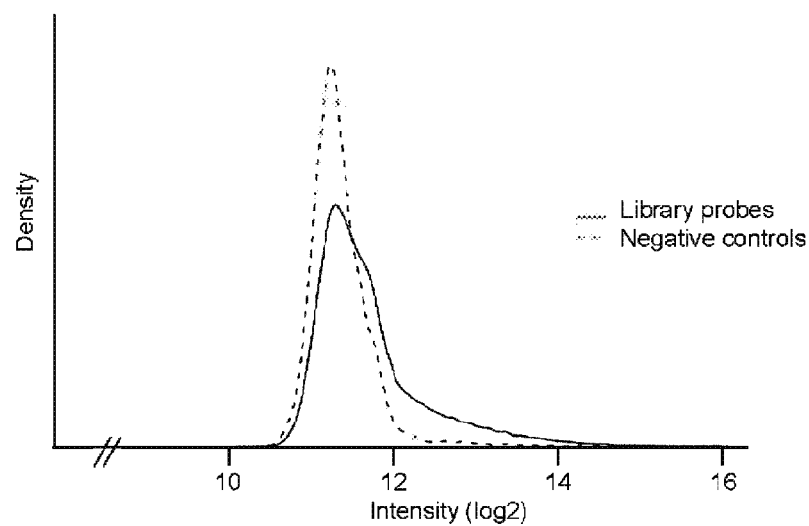

Figure 23
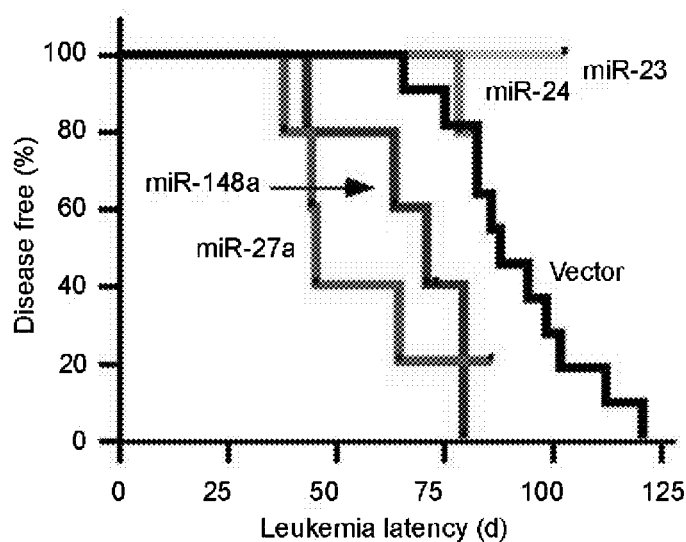
b
|  | CD4 | CD8 | Thy1 | B220 | cKit |
|---|---|---|---|---|---|
| miR-20a | 64.5 | 68.5 | 70.5 | 32 | 34 |
| miR-26a | 86.5 | 91 | 84.5 | 34.5 | 41 |
| miR-27a | 65 | 83 | 85.3 | 78 | 38.5 |
| miR-92a | 52.5 | 63.5 | 62 | 48.5 | 37.5 |
| miR-148 | 73.5 | 80.5 | 77.5 | 28 | 30 |
| miR-223 | 39.5 | 78 | 86 | 1.8 | 1.4 |
c
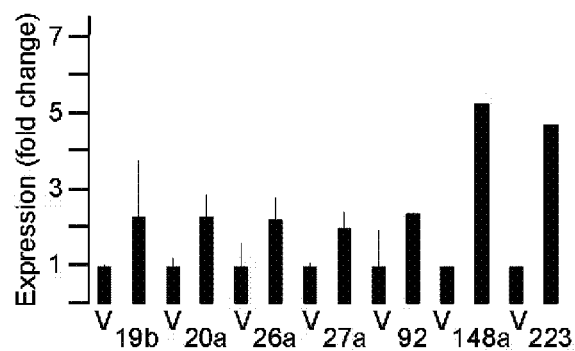

SEQUENCE LISTING

```
<160> NUMBER OF SEQ ID NOS: 18

<210> SEQ ID NO 1
<211> LENGTH: 23
<212> TYPE: RNA
<213> ORGANISM: Homo sapiens

<400> SEQUENCE: 1
ugugcaaauc uaugcaaaac uga                                                23

<210> SEQ ID NO 2
<211> LENGTH: 23
<212> TYPE: RNA
<213> ORGANISM: Homo sapiens

<400> SEQUENCE: 2
ugugcaaauc caugcaaaac uga                                                23

<210> SEQ ID NO 3
<211> LENGTH: 23
<212> TYPE: RNA
<213> ORGANISM: Homo sapiens

<400> SEQUENCE: 3
uaaagugcuu auagugcagg uag                                                23

<210> SEQ ID NO 4
```

```
<211> LENGTH: 23
<212> TYPE: RNA
<213> ORGANISM: Homo sapiens

<400> SEQUENCE: 4
caaagugcuc auagugcagg uag                                              23

<210> SEQ ID NO 5
<211> LENGTH: 22
<212> TYPE: RNA
<213> ORGANISM: Homo sapiens

<400> SEQUENCE: 5
uucaaguaau ccaggauagg cu                                               22

<210> SEQ ID NO 6
<211> LENGTH: 22
<212> TYPE: RNA
<213> ORGANISM: Homo sapiens

<400> SEQUENCE: 6
uauugcacuu gucccggccu gu                                               22

<210> SEQ ID NO 7
<211> LENGTH: 22
<212> TYPE: RNA
<213> ORGANISM: Homo sapiens

<400> SEQUENCE: 7
uauugcacuc gucccggccu cc                                               22

<210> SEQ ID NO 8
<211> LENGTH: 22
<212> TYPE: RNA
<213> ORGANISM: Homo sapiens

<400> SEQUENCE: 8
ucagugcacu acagaacuuu gu                                               22

<210> SEQ ID NO 9
<211> LENGTH: 21
<212> TYPE: RNA
<213> ORGANISM: Homo sapiens

<400> SEQUENCE: 9
ucagugcaug acagaacuug g                                                21

<210> SEQ ID NO 10
<211> LENGTH: 22
<212> TYPE: RNA
<213> ORGANISM: Homo sapiens

<400> SEQUENCE: 10
ugucaguuug ucaaauaccc ca                                               22

<210> SEQ ID NO 11
<211> LENGTH: 63
<212> TYPE: DNA
<213> ORGANISM: Artificial Sequence
<220> FEATURE:
<223> OTHER INFORMATION: antagomir sequence

<400> SEQUENCE: 11
gtgtgcaact ctatgcaaac cttacttcct gtcagtcagt tttgcataga tttgcacatt      60
```

```
ttt                                                              63

<210> SEQ ID NO 12
<211> LENGTH: 63
<212> TYPE: DNA
<213> ORGANISM: Artificial Sequence
<220> FEATURE:
<223> OTHER INFORMATION: antagomir sequence

<400> SEQUENCE: 12
gtgtgcaagt ccatgcaaac cttacttcct gtcagtcagt tttgcatgga tttgcacatt    60
ttt                                                              63

<210> SEQ ID NO 13
<211> LENGTH: 60
<212> TYPE: DNA
<213> ORGANISM: Artificial Sequence
<220> FEATURE:
<223> OTHER INFORMATION: antagomir sequence

<400> SEQUENCE: 13
ttcaagtgat ccaggatcgg atcttcctgt cagagcctat cctggattac ttgaattttt    60

<210> SEQ ID NO 14
<211> LENGTH: 60
<212> TYPE: DNA
<213> ORGANISM: Artificial Sequence
<220> FEATURE:
<223> OTHER INFORMATION: antagomir sequence

<400> SEQUENCE: 14
tattgcaatt gtcccggact atcttcctgt cagacaggcc gggacaagtg caatattttt    60

<210> SEQ ID NO 15
<211> LENGTH: 60
<212> TYPE: DNA
<213> ORGANISM: Artificial Sequence
<220> FEATURE:
<223> OTHER INFORMATION: antagomir sequence

<400> SEQUENCE: 15
tcagtgcgct acagaacgtt atcttcctgt cagacaaagt tctgtagtgc actgattttt    60

<210> SEQ ID NO 16
<211> LENGTH: 64
<212> TYPE: DNA
<213> ORGANISM: Artificial Sequence
<220> FEATURE:
<223> OTHER INFORMATION: antagomir sequence

<400> SEQUENCE: 16
tttggcactg gtagaactcc caatcttcct gtcagagtgt gagttctacc attgccaaat    60
tttt                                                             64

<210> SEQ ID NO 17
<211> LENGTH: 53
<212> TYPE: DNA
<213> ORGANISM: Artificial Sequence
<220> FEATURE:
<223> OTHER INFORMATION: antagomir sequence

<400> SEQUENCE: 17
cctaaggtta agtcgccctc gctctagcga gggcgactta accttaggtt ttt          53
```

```
<210> SEQ ID NO 18
<211> LENGTH: 134
<212> TYPE: DNA
<213> ORGANISM: Homo sapiens

<400> SEQUENCE: 18
tacgcggggg ctcttgagtg gagtgtactt ggaaaggcca gcaagaagaa gcggcgggag        60 ccectcggcg aggactccgt gggcctcaag ccctgaagaa cgcttcagac ggtgccctca       120
tggacgacaa ccag                                                         134
```

METHODS AND COMPOSITIONS FOR THE DETECTION AND TREATMENT OF CANCER INVOLVING MIRNAS AND MIRNA INHIBITORS AND TARGETS

CROSS-REFERENCE TO RELATED APPLICATIONS

This application is a National Phase Application of PCT International Application No. PCT/US11/00365, International Filing Date Feb. 28, 2011, which claims priority of U.S. Provisional Patent Application 61/460,217, filed Dec. 28, 2010, and U.S. Provisional Patent Application 61/339,072, filed Feb. 26, 2010, all of which are hereby incorporated by reference in their entirety.

FIELD OF THE INVENTION

The present invention relates to diagnosing, managing, and treating cancer, including hematologic malignancies, and particularly T-cell acute lymphoblastic leukemia (T-ALL), and for predicting and assessing response to treatment. The invention relates to microRNAs (miRNAs) which are associated with cancer, including hematological malignancies such as T-cell acute lymphoblastic leukemia (T-ALL), and to the assessment and modulation thereof in the treatment and management of cancer.

BACKGROUND OF THE INVENTION

Conventional approaches to treating cancer, including hematologic malignancies, and to predicting and assessing cancer and cancer cell responses to specific treatment regimens rely on properly classifying the type of tumor present. Proper classification, in turn, relies primarily on clinical features, tumor cell morphology, tumor cell immunophenotype and, to a lesser extent, on tumor cell chromosomal abnormalities. However, even within a given tumor type, response to specific treatment regimens is, often, quite variable, and analyses at the molecular level reveal that the tumor types defined by conventional classification schemes are, often, quite heterogeneous.

Recent efforts to classify tumors, including hematologic malignancies, have, therefore, focused on identifying the specific genetic abnormalities or molecular triggers that drive the growth or pathology of specific tumor types. Such genetic abnormalities or molecular triggers can then serve as markers of disease and/or as targets for therapy. Increasing evidence implicates aberrant expression of microRNAs (miRNAs) in most, if not all, human malignancies, and suggests that they may indeed act as either/both tumor suppressors or as oncogenes, and can have effects in numerous cancers which may have a common pathway, or in specific cancers which have particular miRNA initiators or modulators (Visone R and Croce C M (2009) Am J Pathology 174(4):1131-1138; Garzon R et al (2009) Ann Rev Med 60:167-179; Lui W-O et al (2007) Cancer Res 67(13):6031-6043).

MicroRNAs (miRNAs) are ubiquitous regulators of biological processes involved in normal development, in differentiation and in diseases, including cancer. They act by regulating gene expression at the transcriptional and translational levels (Bartel et al (2004) Cell 116:281-297). miRNAs were initially discovered by analysis of mutations causing developmental defects in *Caenorhabditis elegans* (Lee R. C. et al (1993) Cell, 75, 843-854) and altered miRNA expression has been further demonstrated in human cancer, including leukemia (Calin G. A. et al (2004) PNAS USA 101: 11755-11760; Hayashita Y et al (2005) Cancer Res 65:9628-9632; Johnson S. M. et al (2005) Cell 120: 635-647; Lu J et al (2005) Nature 435:834-838; Venturini L et al (2007) Blood 109:4399-4405). MicroRNAs (miRNA) regulate gene expression in a sequence specific manner by hybridization and recruitment of multi-protein complexes to complementary messenger RNA (mRNA) target sequences. miRNA function can transiently be antagonized by antagomirs—chemically modified oligonucleotides complementary to individual miRNAs.

A single miRNA can target hundreds of messenger RNAs and thereby modulate protein output from their respective genes (Bartel D P (2009) Cell 136:215-233). Therefore a single or specific set of miRNAs may control discrete physiological processes by regulating the production of a few critical proteins that coordinate single or interrelated cellular events (e.g., cell proliferation) (Baltimore D et al (2008) Nat Immunol 9:839-845; Bartel D P (2009) Cell 136:215-233).

The 17~92 cluster of miRNAs is highly expressed in hematopoietic cancers and enhances lymphoproliferation and c-Myc-induced leukemogenesis/lymphomagenesis in vivo (He, et al., 2005) (Xiao, et al., 2008). The 17~92 cluster and its paralogues are also expressed in diverse solid tumors, including those derived from breast, colon, lung, pancreas, prostate, and stomach (Volinia, et al., 2006) (Petrocca, et al., 2008). Thus far, however, the function of and the targets regulated by individual miRNAs, in particular of those encoded on polycistronic transcripts, such as the 17~92 cluster, are largely unknown.

Although numerous miRNAs are known and have been identified (known miRNAs are accessible by name with sequence information and characteristics via public database(s) including the miRBase database, mirbase.org; Griffiths-Jones S (2003) Methods Mol Biol 342:129-138), their specific roles in initiation and/or progression of disease(s) and their particular value as targets for therapies or as modulators of disease, including cancer remain largely ill-defined. Therefore, it should be apparent that there still exists a need in the art for a specific elucidation of the relevance of individual or collective miRNAs in cancers, including in specific cancers, for diagnosis and management of disease and for the development of specific therapies directed against individual or collective miRNAs for cancer.

The citation of references herein shall not be construed as an admission that such is prior art to the present invention.

SUMMARY OF THE INVENTION

In its broadest aspect, the present invention extends to methods and compositions for diagnosing and treating cancers, including hematologic malignancies, and for predicting and assessing their response to treatment. Specific miRNAs are provided as participants in the pathogenesis of cancer, particularly hematological malignancies, particularly leukemias and lymphomas, and demonstrated as effective targets in prevention, treatment or alleviation of the disease(s).

The data presented, herein demonstrate that miRNAs, particularly miR-19b, miR-20a, miR-26, miR-92, miR-148 and miR-223 account for the majority of miRNA expression in the cancer, T-cell acute lymphocytic leukemia (T-ALL). Collectively, the novel set of miRNAs (miR-19b, miR-20a, miR-26, miR-92, miR-148 and miR-223) downregulate the activity of a common set of tumor suppressor genes, including PTEN, BCL2L11, NF1, FBXW7, IKZF1 and PHF6, implicated in the pathogenesis of various cancers. These miRNAs are now demonstrated to modulate tumor suppressor genes, particularly in T-ALL, via overlapping and cooperative effects on their expression and are capable of promoting T-ALL in animal models.

In accordance with the invention, the expression of one or more miRNAs, miR-19b, miR-20a, miR-26, miR-92, miR-148 and/or miR-223, can be used for the diagnosis of hematologic malignancies, including T-ALL, for predicting response to specific therapeutic regimens and/or for monitoring response to therapy. Antagonists/antagomirs of miR-19b, miR-20a, miR-26, miR-92, miR-148 and/or miR-223, and particularly of miR-19b, miR-26a, miR-92 and/or miR-223, alone or particularly in combination, are candidate therapeutics against cancers, including hematologic malignancies, and any cancer(s) or condition(s) showing altered expression or overexpression of miR-19b, miR-20a, miR-26, miR-92, miR-148 and/or miR-223.

The present invention relates to methods of modulating cancer via methods and compositions for the specific inhibition of specific miRNAs, particularly one or more of, two or more of, three or more of, or all of miR-19b, miR-20a, miR-26, miR-92, miR-148 and/or miR-223. The compositions and methods of the present invention inhibit the expression and/or activity of miR-19b, miR-20a, miR-26, miR-92, miR-148 and/or miR-223. In particular, the invention provides genetic approaches and nucleic acids for the specific inhibition of one or more or miR-19b, miR-20a, miR-26, miR-92, miR-148 and/or miR-223. It is herein demonstrated that on specific inhibition of one or more of the miRNAs of the present invention, the oncogenesis and leukemogenesis is disrupted and proliferation of tumor or cancer cells is inhibited.

The present invention provides oligonucleotides and nucleic acids which specifically inhibit or block the expression and activity of miRNA(s), particularly including one or more of miR-19b, miR-20a, miR-26, miR-92, miR-148 and/or miR-223. Antagomirs of the miRNAs are provided and assessed herein, with demonstrated anti-oncogenic and anti-leukemogenic activity. In an aspect of the invention, antisense oligonucleotides and the expression of nucleic acid complementary to one or more of miR-19b, miR-20a, miR-26, miR-92, miR-148 and/or miR-223 specifically inhibit expression and/or activity of said one or more miRs and block miRNA mediated tumorigenesis and cancer cell proliferation.

A composition is provided herein for use in treatment of a hematological malignancy comprising one or more antagomir which is complementary to one or more miRNA selected from miR-19, miR-20, miR-26, miR-92, miR-148 and miR-223. The invention further provides a composition comprising one or more oligonucleotide which is substantially complementary to one or more miRNA selected from miR-19, miR-20, miR-26, miR-92, miR-148 and miR-223 for use in treatment of a hematological malignancy. In an aspect of the invention, the hematological malignancy is selected from T-cell acute lymphoblastic leukemia (T-ALL), B-cell acute lymphoblastic leukemia (B-ALL), diffuse large B-cell lymphoma (DLBCL) and Burkitt's lymphoma. In a particular aspect the malignancy is a leukemia, particularly T-ALL.

The invention includes a composition for use in treatment of cancer comprising at least two antagomirs or oligonucleotides complementary to at least two miRNAs selected from miR-19, miR-20, miR-26, miR-92, miR-148 and miR-223. The composition may particularly comprise at least two antagomirs or oligonucleotides complementary to at least two miRNAs selected from miR-19, miR26 and miR-92.

In a further embodiment, the invention includes an antisense oligonucleotide or an antagomir comprising a sequence substantially complementary to at least one of the miRNA sequences provided herein, selected from miR-19, miR-20, miR-26, miR-92, miR-148 and miR-223. The antagonist or antagomir may be substantially complementary to the miRNA target sequences set out in Table 1. In particular, antagomirs, antagonists or oligonucleotides of the invention include oligonucleotides comprising a sequence substantially complementary to nucleotides selected from the group of SEQ IDs 1-10 as set out in Table 1, or a subset of nucleotides thereof sufficient to inhibit the expression or activity of one or more of said miRNA sequences SEQ ID NOs 1-10. The invention includes antisense oligonucleotides or antagomirs comprising one or more sequence selected from the group of those set out in Table 2, or as set out in SEQ ID NOS: 11-15.

In an aspect of the composition of the invention, the one or more antagomir or oligonucleotide comprises at least one modified nucleotide. In a particular aspect, the antagomirs, nucleic acids and oligonucleotides of the present invention may be modified, either by manipulation of the chemical backbone of the nucleic acids or by covalent or non-covalent attachment of other moieties. In each or any case, such manipulation or attachment may serve to modify the stability, cellular, tissue or organ uptake, or otherwise enhance efficacy of the nucleic acids and oligonucleotides. In further aspects of the invention, the antagomirs or oligonucleotides may be covalently linked to other molecules, including but not limited to polypeptides, carbohydrates, lipid or lipid-like moieties, ligands, chemical agents or compounds, which may serve to enhance the uptake, stability or to target the oligonucleotides.

The composition of the invention may further comprise one or more additional compound selected from anti-cancer agents or therapeutics, anti-mitotic agents, apoptotic agents or antibodies, or immune modulators. A composition of the present invention may be administered alone or in combination with other treatments, therapeutics or agents, either simultaneously or sequentially dependent upon the condition to be treated. In addition, the present invention contemplates and includes compositions comprising the one or more specific miR antagonist/antagomir herein described and other agents or therapeutics such as anti-cancer agents or therapeutics, anti-mitotic agents, apoptotic agents or antibodies, or immune modulators. More generally these anti-cancer agents may be tyrosine kinase inhibitors or phosphorylation cascade inhibitors, post-translational modulators, cell growth or division inhibitors (e.g. anti-mitotics), inhibitors or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. In addition, the composition may be administered with immune modulators, such as interleukins, tumor necrosis factor (TNF) or other growth factors, colony stimulating factors, cytokines or hormones such as dexamethasone which stimulate the immune response and reduction or elimination of cancer cells or tumors. The composition may also be administered with anti-tumor antigen antibodies.

The invention includes a pharmaceutical composition comprising a therapeutically effective amount of an antagomir or oligonucleotide substantially complementary to one or more miRNA selected from miR-19, miR-20, miR-26, miR-92, miR-148 and miR-223 and a pharmaceutically acceptable carrier or diluent.

In a further embodiment, the present invention relates to certain therapeutic methods which would be based upon the activity of the miRNAs and modulation thereof, in particular in inhibition of the activity and/or expression of one or more miRNA associated with oncogenesis or leukemogenesis. For example, drugs or other binding partners to the miRNAs, as in anagomirs or oligonucleotides, for instance, may be administered to inhibit miRNA expression or activity, as in the potentiation of anti-cancer therapy.

Methods for inhibiting expression of one or more miRNA particularly selected from miR-19, miR-20, miR-26, miR-92, miR-148 and miR-223 are provided. In particular, a method of inhibiting the expression of one or more miRNAs indicated as relevant in the invention is provided, comprising contacting cells which express one or more miRNAs with an effective amount of the antagomir or oligonucleotide of the present invention whereby expression or activity of said one or more miRNAs is inhibited.

The invention further includes a method of treating or preventing a condition, such as cancer or other hyperproliferative disorder, associated with the expression of the miRNAs of the invention or heightened expression of said miRNAs in a mammal comprising administering to said mammal a therapeutically effective amount of a compound or agent which inhibits the expression or activity of the miRNAs, particularly miR-19, miR-20, miR-26, miR-92, miR-148 and/or miR-223. In one aspect of this method, said compound or agent is an antisense oligonucleotide or antagomir which specifically hybridizes to one or more miRNA of miR-19, miR-20, miR-26, miR-92, miR-148 and miR-223.

In a further aspect, a method of treating or inhibiting the progression of cancer in a mammal is included, comprising administering to a mammal a therapeutically effective amount of a compound or agent which inhibits the expression, or activity of the miRNAs, particularly miR-19, miR-20, miR-26, miR-92, miR-148 and/or miR-223. Cancers which are susceptible to the invention's method include cancer selected from the group of pancreatic cancer, lung cancer, skin cancer, urinary tract cancer, bladder cancer, liver cancer, thyroid cancer, colon cancer, intestinal cancer, gastric cancer, leukemia, lymphoma, neuroblastoma, head and neck cancer, breast cancer, ovarian cancer, stomach cancer, esophageal cancer and prostate cancer. In a particular aspect, the cancer is a hematological malignancy, particularly selected from T-cell acute lymphoblastic leukemia (T-ALL), B-cell acute lymphoblastic leukemia (B-ALL), diffuse large B-cell lymphoma (DLBCL) and Burkitt's lymphoma. In a particular aspect the cancer is a leukemia, particularly T-ALL.

The invention provides a method of enhancing or increasing the expression of a tumor suppressor gene selected from Pten, Bim/Bcl2l11, Phf6, Ikzf1, Nf1 and Fbxw7 comprising contacting cells which are capable of expressing one or more of said tumor suppressor gene with one or more antagomir or oligonucleotide substantially complementary to one or more miRNA selected from miR-19, miR-20, miR-26, miR-92, miR-148 and miR-223. In an aspect, the method comprises contacting cells with at least two antagomirs or oligonucleotides substantially complementary to at least two miRNAs selected from miR-19, miR26 and miR-92.

The invention further provides a method of treating or alleviating cancer wherein the miR17~92 cluster is amplified of overexpressed comprising administering one or more compound that inhibits the expression or activity of one or more miRNA selected from miR-19, miR-20, miR-26, miR-92, miR-148 and miR-223. In an aspect, the method includes wherein one or more compound that inhibits miR-19, miR-26 and miR-92 is administered.

The diagnostic and medical utility of the present invention extends to the use of the present in assays to screen for or evaluate cancer, malignancy, lymphoma, and/or leukemia in a mammal, particularly a human patient. Thus, methods for monitoring cancer and/or evaluating response to treatment are provided wherein the expression or activity of one or more miRNA selected from miR-19, miR-20, miR-26, miR-92, miR-148 and miR-223 is assessed. In one such aspect, the activity of at least two miRNAs associated with cancer, selected from miR-19, miR-20, miR-26, miR-92, miR-148 and miR-223 is determined and assessed, so as to monitor or evaluate cancer or response to cancer treatment, such as at the molecular level. For instance, a reduction in the expression and/or activity of one or more miRNAs selected from miR-19, miR-20, miR-26, miR-92, miR-148 and miR-223 may be associated with an improved prognosis or positive response to a cancer treatment or therapeutic agent. The present invention further includes an assay system which may be prepared in the form of a test kit for the quantitative analysis of the extent of the presence of the miRNAs hereof, or to identify drugs or other agents that may mimic or block their activity.

In an aspect of the invention, a method is provided for monitoring cancer or evaluating response to cancer therapy in a mammal comprising:
(a) obtaining a cellular sample from said mammal;
(b) measuring the expression or activity of at least two miRNAs selected from miR-19, miR-20, miR-26, miR-92, miR-148 and miR-223 in said sample; and
(c) comparing the expression or activity of said at least two miRNAs to that in or from a reference sample;
wherein the expression or activity of at least two of said miRNAs is altered relative to the reference sample. In one aspect of this method, the expression or activity of three or more miRNAs is measured, compared, and altered. In an additional aspect, the cancer is selected from the group of pancreatic cancer, lung cancer, skin cancer, urinary tract cancer, bladder cancer, liver cancer, thyroid cancer, colon cancer, intestinal cancer, leukemia, lymphoma, neuroblastoma, glioblastoma, head and neck cancer, breast cancer, ovarian cancer, stomach cancer, gastrointestinal cancer, esophageal cancer and prostate cancer. In a particular aspect, the cancer is a hematological malignancy.

In addition, a method is provided for identifying compounds or agents which inhibit the expression of one or more miRNAs associated with cancer comprising the steps of:
(a) incubating a cell expressing an miRNA selected from miR-19, miR-20, miR-26, miR-92, miR-148 and miR-223 in the presence and absence of a candidate compound or agent; and
(b) detecting or measuring the expression or activity of said miRNA selected from miR-19, miR-20, miR-26, miR-92, miR-148 and miR-223 in the presence and absence of a candidate compound or agent,
whereby a decrease in the expression of said miRNA selected from miR-19, miR-20, miR-26, miR-92, miR-148 and miR-223 in the presence of said candidate compound or agent versus in the absence of said candidate compound or agent indicates that said compound or agent inhibits the expression of miRNA selected from miR-19, miR-20, miR-26, miR-92, miR-148 and miR-223.

The invention thus provides a method for identifying a compound for treatment or prevention of a hematological malignancy, wherein said compound antagonizes or inhibits the expression or activity of an miRNA associated with said malignancy comprising:
(a) contacting a compound with a cell expressing one or more miRNA selected from miR-19, miR-20, miR-26, miR-92, miR-148 and miR-223; and
(b) determining the expression or activity of one or more of said miRNA;
wherein the expression or activity of said miRNA is inhibited or reduced.

In an aspect of the method, the expression or activity of said one or more miRNA is assessed by determining the amount of said miRNA, the activity or expression of one or more miRNA target tumor suppressor gene, or the growth or viability of a leukemia or lymphoma cell expressing said miRNA. In a further aspect of the method, the one or more miRNA target tumor suppressor gene is selected from Pten, Bim/Bcl2l11, Phf6, Ikzf1, Nf1 and Fbxw7. In an additional aspect, a method is provided wherein the leukemia or lymphoma cell is a T-ALL patient cell sample or T-ALL cell line.

The invention includes a method for detecting or evaluating a hematological malignancy in a mammal comprising:
(a) obtaining a sample of blood or blood cells from said mammal;
(b) measuring the expression or activity of one or more miRNA selected from miR-19, miR-20, miR-26, miR-92, miR-148 and miR-223; and
(c) comparing the expression or activity of said one or more miRNA to that in or from a reference sample;
wherein the expression or activity of at least one of said one or more miRNA is increased relative to the reference sample.

The present invention includes a method for detecting or evaluating cancer in a mammal comprising:
(a) obtaining a cellular sample from said mammal;
(b) measuring the expression or activity of at least two miRNAs selected from miR-19, miR-20, miR-26, miR-92, miR-148 and miR-223 in said sample; and
(c) comparing the expression or activity of said at least two miRNAs to that in or from a reference sample;
wherein the expression or activity of at least two of said miRNAs is increased relative to the reference sample.

In an aspect of the above methods, the expression or activity of two or more miRNAs is measured, compared, and increased. In one aspect of the above methods, the expression or activity of three or more miRNAs is measured, compared, and increased. In a further aspect, the cancer is selected from the group of pancreatic cancer, lung cancer, skin cancer, urinary tract cancer, bladder cancer, liver cancer, thyroid cancer, colon cancer, intestinal cancer, leukemia, lymphoma, neuroblastoma, glioblastoma, head and neck cancer, breast cancer, ovarian cancer, stomach cancer, gastrointestinal cancer, esophageal cancer and prostate cancer. In a particular aspect, the cancer is a hematological malignancy, particularly selected from T-cell acute lymphoblastic leukemia (T-ALL), B-cell acute lymphoblastic leukemia (B-ALL), diffuse large B-cell lymphoma (DLBCL) and Burkitt's lymphoma. In a particular aspect the cancer is a leukemia, particularly T-ALL.

The antagomirs or oligonucleotides of the present invention may be labeled with a detectable label. In particular aspects, the label may be selected from enzymes, ligands, chemicals which fluoresce and radioactive elements. In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Other objects and advantages will become apparent to those skilled in the art from a review of the following description which proceeds with reference to the following illustrative drawings.

BRIEF DESCRIPTION OF THE DRAWINGS

FIG. 4. Cytogenetic characterization of the novel t(13;14)(q32;q11) translocation in T-ALL. Higher resolution of double-color FISH analysis highlighting the existence of a T-ALL oncogene localizing to the 17~92 cluster (same as shown in FIG. 3). Analysis using a RB1 probe (green) in 13q14 and genomic clones RP11-97P7 and RP11-980D6 overlapping the 17~92 locus in 13q32 (red). Probe RP11-97P7 shows a split signal with retention of half of the clone in chromosome 13 and the other half mapping to the derivative chromosome 14. Probe RP11-980D6 shows some retention of signal in chromosome 13 with most of the clone mapping to the derivative chromosome 14.

FIG. 5. Molecular characterization of the t(9;14) Notch1 transcript. (a) Notch1 gene structure and protein domains corresponding to the full-length Notch1 transcript. (b) 5'RACE sequence of Notch1 truncated transcript expressed in leukemic lymphoblasts. The chimeric Notch1-chromosome 14 sequence (SEQ ID NO:18) encompasses Notch1 sequences distal to the breakpoint located in Notch1 exon 28. The first ATG codon for this mRNA is located in Notch1 exon 29. The sequence corresponding to the 5'RACE primer located in Notch1 exon 29 is indicated in bold text. (c) Structure of the truncated Notch1 mRNA generated by the t(9;14).

FIG. 7. miR-19 cooperates with c-Myc and blocks p53-dependent apoptosis in EµMyc lymphoma. (a) Schematic of experimental design to generate miR-19-expressing lymphomas derived from EµMyc/p53$^{+/-}$ HPCs. (b) miR-19-expressing HPCs are rapidly enriched during Myc-driven lymphomagenesis in vivo. (c) PCR to assess loss of heterozygosity in the p53 locus in vector- and miR-19-expressing lymphomas derived from EµMyc/p53$^{+/-}$ HPCs. (Neo and WT indicate the knockout and wild type alleles of p53.)

FIG. 8. Gene expression analysis of parental and mIR-19 transduced FL5-12 cells. (a) Heat-map illustration of the unsupervised clustering analysis reveals differences in gene expression between parental (FL/Vector) and miR-19-expressing FL5-12 cells (FL/miR-19). (b) Comparison of the expression change of predicted miR-19 targets represented on the array (336 genes, red line) versus all represented genes (8065 genes, black line) ($p<2e-04$; KS-test). (c) Histogram of genes whose expression is down regulated by >1SD in FL5-12/miR-19 cells compared to parental cells. Globally, miR-19 targets are significantly more down regulated than other genes; however there is no significant enrichment of miR-19 targets among genes showing more pronounced (1.5 or 2 SD) reductions in expression.

FIG. 11. Diagrammatic summary of the results of the shRNA screen. (a) From a large-scale shRNA library of ~12,000 shRNAs and 7,853 unique targets, shRNAs against eight genes were shown to phenocopy miR-19. Five of these eight genes contained a miR-19 seed match compared to 938 predicted miR-19 targets. Hence, the genetic screen results in a highly significant enrichment for miR-19 target genes ($p<7.2$ exp-07, Fisher's exact test). (b) Identical analysis for the murine genome, which contains 744 predicted miR-19 target genes, and where the murine Dock5 gene is not a target. Fisher's exact test confirms enrichment for miR-19 targets in the murine genome ($p<3.2$ exp-05).

FIG. 18. Retroviral shRNA library vector. (a) Diagram of the MSCV-based MRP retroviral library vector used in the shRNA library screen. Note that, in validation experiments. a GFP-expressing version of this construct (MLP) was used for ease of detection. (b) Immunoblot of lysates from primary fibroblasts treated with doxorubicin to induce p53 or untreated and transduced with the indicated vector constructs with and without the shRNA against p53. Both MRP and MLP vectors expressing the p53 shRNA produce efficient protein knockdown. (c) Comparison of signal intensity from arrayed half-hairpins that either match. shRNAs present in the library (library probes) or negative controls to determine signal/background ratio.

FIG. 23. Candidate miRNAs act as oncogenes in a murine T-ALL model. a. Kaplan-Meier analysis of leukemia-free survival after transplantation of HPCs expressing NOTCH1-ICN and vector (black, n=13) or miR-27 (red, n=5; p<0.05 compared to vector), miR-24 (magenta, n=5; p=0.5), miR-23a (green, n=5; p<0.05) or miR-148a (blue, n=7; p<0.05). b. Analysis of surface marker expression on murine T-ALLs, with the percentage of cells staining positive for the indicated marker. c. Quantitative RT-PCR measurement of miRNA expression in murine leukemic cells expressing the indicated miRNA compared to leukemias arising in vector controls.

Bold letters indicate miRNAs that are highly expressed in human T-ALL; the width of each line is proportional to the calculated strength and conservation of the miRNA-mRNA interaction.

Figure 28:
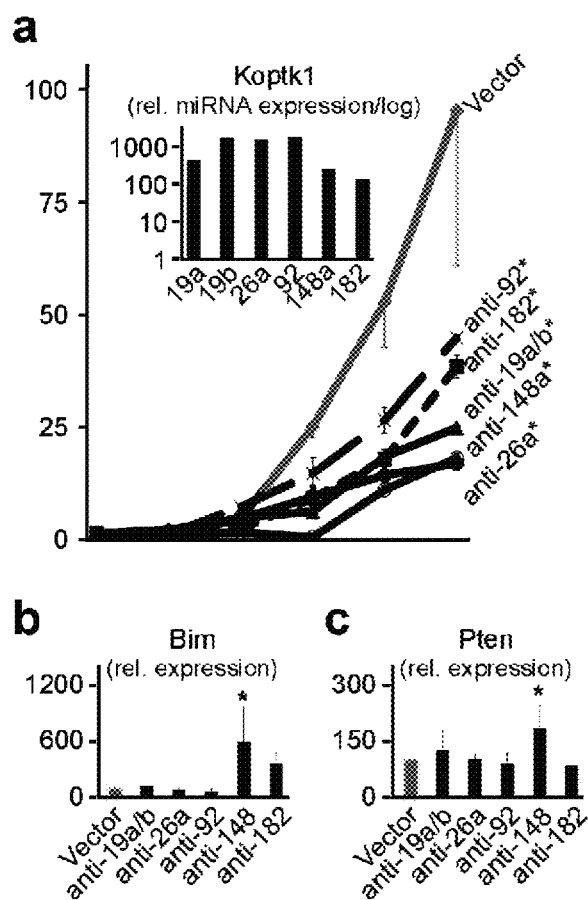

FIG. 28. Antagomir studies in the human Koptk1 T-ALL cell line. a. Cell number during in vitro culture of Koptk1 cells expressing the indicated antagomirs (mean and SD for each time point, * indicates significant (p<0.05) growth delay). b and c. Quantitative RT-PCR of BCL2L11 (b) and PTEN (c) mRNA levels in Koptk1 cells expressing the indicated antagomirs (mean and SD, * is p<0.05 compared to vector).

Figure 29:
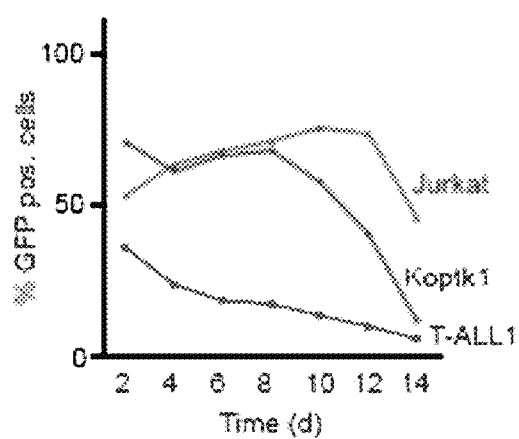

FIG. 29. Antagomir to miR-223 exhibits anti-proliferative effects in T-ALL cell lines. Results of a competition assay. T-ALL lines (Koptk1, T-ALL1, and Jurkat) were transduced with a lentivirus construct encoding miR-223 antagomir and GFP. Expression of GFP was assessed by FACS every 48 hrs.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "miRNAs", "miRs", "microRNAs", miRNA Targets", and any variants not specifically listed, may be used herein interchangeably, and as used throughout the present application and claims refer to nucleic acid materials, including ribonucleic acids, RNAs, including single or multiple RNAs, and extends to miRNAS including those selected from miR-19, miR-20, miR-26, miR-92, miR-148 and miR-223 and those having the nucleic acid sequence data described herein and presented in TABLE 1 (SEQ ID NOs: 1-10), and the profile of activities set forth herein and in the Claims. Accordingly, sequences displaying substantially equivalent or altered activity are likewise contemplated. These modifications may be deliberate, for example, such as modifications obtained through site-directed mutagenesis, or may be accidental, such as those obtained through mutations in hosts or variants thereof. Also, the terms "miRNAs", "miRs", "microRNAs" and "miRNA Targets" are intended to include within their scope nucleic acids specifically recited herein as well as all substantially homologous analogs and allelic variations.

The terms "oligonucleotides", "antisense", "antisense oligonucleotides", "antagomirs", "miRNA antagomirs" and any variants not specifically listed, may be used herein interchangeably, and as used throughout the present application and claims refer to nucleic acid material including single or multiple nucleic acids, and extends to those oligonucleotides or antagomirs complementary to the miRNA nucleic acid sequences described herein, including as presented in TABLE 1 and the complementary sequences of TABLE 2 and having the profile of activities set forth herein and in the Claims, particularly in being capable of inhibiting the expression of one or more miRNAs hereof, particularly inhibiting one or more miRNA selected from miR-19, miR-20, miR-26, miR-92, miR-148 and miR-223. In particular, the oligonucleotides of the present invention may be substantially complementary to nucleic acid sequence specific to miRNA selected from miR-19, miR-20, miR-26, miR-92, miR-148 and miR-223, as provided in SEQ ID NO: 11-15, or to a portion thereof, as provided for example in TABLE 2. Accordingly, nucleic acids or analogs thereof displaying substantially equivalent or altered activity are likewise contemplated. These modifications may be deliberate, for example, such as modifications obtained through site-directed mutagenesis, or may be accidental, such as those obtained as variants or through mutations in hosts that are producers of the nucleic acids or of the antagomirs/oligonucleotides. The term "oligonucleotide," as used herein in referring to the antagonists of the present invention, is defined as a molecule comprised of two or more ribonucleotides, preferably more than three. Its exact size will depend upon many factors which, in turn, depend upon the ultimate function and use of the oligonucleotide.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense.

As used herein, the term 'antagonist' is used to describe a compound that does not provoke a biological response itself upon binding to a receptor, but blocks or dampens agonist-mediated responses.

The term 'assay' means any process used to measure a specific property of a compound. A 'screening assay' means a process used to characterize or select compounds based upon their activity from a collection of compounds.

The term 'binding affinity' is a property that describes how strongly two or more compounds associate with each other in a non-covalent relationship. Binding affinities can be characterized qualitatively, (such as 'strong', 'weak', 'high', or 'low') or quantitatively (such as measuring the $K_D$).

The term 'carrier' means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

The term 'complex' means the entity created when two or more compounds bind to, contact, or associate with each other.

The term 'compound' is used herein in the context of a 'test compound' or a 'drug candidate compound' described in connection with the assays of the present invention. As such, these compounds comprise organic or inorganic compounds, derived synthetically, recombinantly, or from natural sources.

The term 'fragment of a polynucleotide' relates to oligonucleotides that comprise a stretch of contiguous nucleic acid residues that exhibit substantially a similar, but not necessarily identical, activity as the complete sequence. In a particular aspect, 'fragment' may refer to a oligonucleotide comprising a nucleic acid sequence of at least 5 nucleic acid residues (preferably, at least 10 nucleic acid residues, at least 15 nucleic acid residues, at least 20 nucleic acid residues, at least 25 nucleic acid residues, at least 40 nucleic acid residues, at least 50 nucleic acid residues, at least 60 nucleic residues, at least 70 nucleic acid residues, at least 80 nucleic acid residues, at least 90 nucleic acid residues, at least 100 nucleic acid residues, at least 125 nucleic acid residues, at least 150 nucleic acid residues, at least 175 nucleic acid residues, at least 200 nucleic acid residues, or at least 250 nucleic acid residues) of the nucleic acid sequence of said complete sequence.

The term 'fragment of a polypeptide' relates to peptides, oligopeptides, polypeptides, proteins, monomers, subunits and enzymes that comprise a stretch of contiguous amino acid residues, and exhibit substantially a similar, but not necessarily identical, functional or expression activity as the complete sequence. In a particular aspect, 'fragment' may refer to a peptide or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of said complete sequence.

The term 'polynucleotide' means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more particularly 70 percent of its base pairs are in common, most particularly 90 percent, and in a particular embodiment, 100 percent of its base pairs. The polynucleotides include polyribonucleic acids, polydeoxyribonucleic acids, and synthetic analogues thereof. It also includes nucleic acids with modified backbones such as peptide nucleic acid (PNA), polysiloxane, and 2'-O-(2-methoxy)ethylphosphorothioate. The polynucleotides are described by sequences that vary in length, that range from about 10 to about 5000 bases, particularly about 100 to about 4000 bases, more particularly about 250 to about 2500 bases. One polynucleotide embodiment comprises from about 10 to about 30 bases in length. A particular embodiment of polynucleotide is the polyribonucleotide of from about 17 to about 22 nucleotides, more commonly described as small interfering RNAs (siRNAs—both double stranded siRNA molecules and, self-complementary single-stranded siRNA molecules (shRNA)). Another particular embodiment are nucleic acids with modified backbones such as peptide nucleic acid (PNA), polysiloxane, and 2'-O-(2-methoxy)ethylphosphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection. Polynucleotides herein are selected to be 'substantially' complementary to different strands of a particular target DNA sequence. This means that the polynucleotides must be sufficiently complementary to hybridize with their respective strands. Therefore, the polynucleotide sequence need not reflect the exact sequence of the target sequence. For example, a non-complementary nucleotide fragment may be attached to the 5' end of the polynucleotide, with the remainder of the polynucleotide sequence being complementary to the strand. Alternatively, non-complementary bases or longer sequences can be interspersed into the polynucleotide, provided that the polynucleotide sequence has sufficient complementarity with the sequence of the strand to hybridize therewith under stringent conditions or to form the template for the synthesis of an extension product.

The term "cancer" refers to a malignant or benign growth of cells in the blood, skin or in body organs, for example but without limitation, hematological malignancy, breast, prostate, lung, gastrointestinal, liver, neuroblastoma, glioblastoma, kidney, pancreas, stomach or bowel. A cancer tends to infiltrate into adjacent tissue and spread (metastasize) to distant organs, for example to bone, liver, lung or the brain. As used herein the term cancer includes both metastatic tumour cell types, such as but not limited to, melanoma, lymphoma, leukemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20$^N$C below the predicted or determined $T_m$ with washes of higher stringency, if desired.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell- or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

Mutations can be made in the sequences hereof such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following are examples of various groupings of amino acids:
Amino acids with nonpolar R groups: Alanine, Valine, Leucine, Isoleucine, Proline, Phenylalanine, Tryptophan, Methionine
Amino acids with uncharged polar R groups: Glycine, Serine, Threonine, Cysteine, Tyrosine, Asparagine, Glutamine
Amino acids with charged polar R groups (negatively charged at Ph 6.0): Aspartic acid Glutamic acid
Basic amino acids (positively charged at pH 6.0): Lysine, Arginine, Histidine (at pH 6.0) Another grouping may be those amino acids with phenyl groups: Phenylalanine, Tryptophan, Tyrosine
Another grouping may be according to molecular weight (i.e., size of R groups): Glycine (75), Alanine (89), Serine (105), Proline (115), Valine (117), Threonine (119), Cysteine (121), Leucine (131), Isoleucine (131), Asparagine (132), Aspartic acid (133), Glutamine (146), Lysine (146), Glutamic acid (147), Methionine (149), Histidine (at pH 6.0) (155), Phenylalanine (165), Arginine (174), Tyrosine (181), Tryptophan (204)

Particularly preferred substitutions are: Lys for Arg and vice versa such that a positive charge may be maintained; Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein. Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

An "antibody combining site" is that structural portion of an antibody molecule comprised of heavy and light chain variable and hypervariable regions that specifically binds antigen. The phrase "antibody molecule" in its various grammatical forms as used herein contemplates both an intact immunoglobulin molecule and an immunologically active portion of an immunoglobulin molecule. The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Therapeutically effective amount' means that amount of a drug, compound, antimicrobial, antibody, or pharmaceutical agent that will elicit the biological or medical response of a subject that is being sought by a medical doctor or other clinician. In particular, with regard to gram-positive bacterial infections and growth of gram-positive bacteria, the term "effective amount" is intended to include an effective amount of a compound or agent that will bring about a biologically meaningful decrease in the amount of or extent of infection of gram-positive bacteria, including having a bacteriocidal and/or bacteriostatic effect. The phrase "therapeutically effective amount" is used herein to mean an amount sufficient to prevent, and preferably reduce by at least about 30 percent, more preferably by at least 50 percent, most preferably by at least 90 percent, a clinically significant change in the growth or amount of infectious bacteria, or other feature of pathology such as for example, elevated fever or white cell count as may attend its presence and activity.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

The phrase "pharmaceutically acceptable" refers to molecular entities and compositions that are physiologically tolerable and do not typically produce an allergic or similar untoward reaction, such as gastric upset, dizziness and the like, when administered to a human.

In its primary aspect, the present invention concerns the identification of a miRNAs associated with oncogenesis and leukemogenesis and modulation or monitoring thereof in the management and treatment of cancer. The present invention is thus based on the discovery that agents that inhibit the expression and or activity of the miRNA Targets (including one or more of miR-19b, miR-20a, miR-26, miR-92, miR-148 and/or miR-223, including as set out below in Table 1) disclosed herein are able to result in inhibition of progression of cancer (including preventing leukemogenesis in animal models), and in suppression of the inhibitory effects of the miRNA Targets on tumor suppressor genes, in particular the tumor suppressor genes Pten, Bim/Bcl2l11, Phf6, Ikzf1, Nf1 and/or Fbzw7. The present invention therefore provides miRNA Targets which are involved in or associated with cancer or ongogenesis, methods for screening for agents capable of inhibiting the activity or expression of the miRNA Targets, and uses of these agents in the prevention and/or treatment of cancers and diseases associated with elevated expression of the miRNA Targets, such as cancers associated with miR 17~92 translocations, hematological cancers, breast cancer, glioblastoma and melanoma.

TABLE 1

OF miRNA TARGETS

| miRNA | Seed Sequence | SEQ ID NO: |
|---|---|---|
| miR-19a | UGUGCAAAUCUAUGCAAAACUGA | SEQ ID NO: 1 |
| miR-19b | UGUGCAAAUCCAUGCAAAACUGA | SEQ ID NO: 2 |
| miR-20a | UAAAGUGCUUAUAGUGCAGGUAG | SEQ ID NO: 3 |
| miR-20b | CAAAGUGCUCAUAGUGCAGGUAG | SEQ ID NO: 4 |
| miR-26a | UUCAAGUAAUCCAGGAUAGGCU | SEQ ID NO: 5 |
| miR-92a | UAUUGCACUUGUCCCGGCCUGU | SEQ ID NO: 6 |
| miR-92b | UAUUGCACUCGUCCCGGCCUCC | SEQ ID NO: 7 |
| miR-148a | UCAGUGCACUACAGAACUUUGU | SEQ ID NO: 8 |
| miR-152 | UCAGUGCAUGACAGAACUUGG | SEQ ID NO: 9 |
| miR-223 | UGUCAGUUUGUCAAAUACCCCA | SEQ ID NO: 10 |

The present invention relates to methods and compositions for the specific inhibition of expression and/or activity of one or more miRNAs particularly associated with oncogenesis or leukemogenesis, including in combination, such miRNAs selected from miR19, miR20, miR26, miR92, miR148 and miR223, including as set out in the Table above. It is notable that certain miR5 possess overlapping activity and sequences which are substantially equivalent, for example miR19 may encompass each and both of miR19a and miR19b, miR20 may encompass each and both of miR20a and miR20b, etc. In particular, the invention provides genetic approaches and nucleic acids for the specific inhibition of the miRNA Target(s). It is herein demonstrated that on specific inhibition of one or more of the miRNA Targets the oncogenic/leukemogenic pathway is disrupted and, specifically, that leukemogenesis, leukemia cell proliferation are inhibited, or are blocked. In particular, antagomirs, antisense oligonucleotides and the expression of nucleic acid complementary to one or more miRNA Target(s) specifically inhibit expression or activity of said one or more miRNA Target(s) and block miR mediated tumorigenesis.

Antagomirs

The present invention provides an antagomir, oligonucleotide, nucleic acid which is substantially complementary to one or more miRNA Target(s), particularly miRNA selected from miR19b, miR26a, miR26, miR92, miR148 and miR223, wherein said oligonucleotide inhibits the expression or activity of one or more miRNA Target(s). Exemplary antagomirs are provided in TABLE 2 below. The below exemplary sequences were utilized and their activity demonstrated in the Examples provided herein.

TABLE 2

OF ANTAGOMIRS

| miRNA TARGET | ANTAGOMIR SEQUENCE 5'-3' | SEQ ID NO: |
|---|---|---|
| miR19a | GTGTGCAACTCTATGCAAACCTTACTTCCTGTCAGTCAGTTTTGCATAGATTTGCACATTTTT | 11 |
| miR19b | GTGTGCAAGTCCATGCAAACCTTACTTCCTGTCAGTCAGTTTTGCATGGATTTGCACATTTTT | 12 |
| miR26a | TTCAAGTGATCCAGGATCGGATCTTCCTGTCAGAGCCTATCCTGGATTACTTGAATTTTT | 13 |
| miR92a | TATTGCAATTGTCCCGGACTATCTTCCTGTCAGACAGGCCGGGACAAGTGCAATATTTTT | 14 |
| miR148 | TCAGTGCGCTACAGAACGTTATCTTCCTGTCAGACAAAGTTCTGTAGTGCACTGATTTTT | 15 |
| miR182 (control) | TTTGGCACTGGTAGAACTCCCAATCTTCCTGTCAGAGTGTGAGTTCTACCATTGCCAAATTTTT | 16 |
| scrambld control (MZIP000) | CCTAAGGTTAAGTCGCCCTCGCTCTAGCGAGGGCGACTTAACCTTAGGTTTTT | 17 |

The above exemplary antagomirs are available commercially as miRZIPs™ from System Biosciences (Mountain View, Calif.; systembio.com).

Stoffel and colleagues first described silencing of miRNAs in vivo with "antagomirs" in 2005 (Krutzfeldt J et al (2005) Nature 438(7068):685-689). Intravenous administration of antagomirs against specific miRNAs resulted in marked reduction of corresponding miRNA levels in specific organs. Chemically modified single-stranded RNA analogues complementary to a specific miRNA are effective as antagomirs. Oligonucleotides have been described linked to cholesterol molecule to enhance uptake and improve target degradation and with phosphorothioate modifications (Krutzfeld J et al (2007) Nucl Adids Res 35(9):2885-2892). Pharmaceutical compositions of shortened and modified oligonucleotide antagomirs have been described including in US2010/0286234 and WO 2010/144485 A1. Scherr et al have described lentivirus-mediated antagomir expression systems for specific inhibition of miRNA function (Scherr M et al (2007) Nucl Acids Res 35(22):e149 (doi:10.1093/nar/qkm971). Lentivirus antagomirs are available commercially, including as miRZIPs™ from System Biosciences, as well as microRNA mimics meridian from Dharmacon/Thermo-Scientific. The knowledge of miRNA sequences (including publicly available in databases such as mirBase) and commercial and public availability of antagomirs, lentivirus constructs, and synthetic oligonucleotides makes antagomirs/oligonucleotides as exemplary miRNA Target(s) inhibitors available for testing, assessment and evaluation. Thus, one of skill in the art can readily design, make or acquire suitable antagomirs or oligonucleotides for use and application in accordance with the present invention.

The invention includes an antisense oligonucleotide or an antagomir comprising a sequence substantially complementary to at least one of the miRNA sequences provided herein, selected from miR-19, miR-20, miR-26, miR-92, miR-148 and miR-223. The antagonist or antagomir may be substantially complementary to the miRNA target sequences set out in Table 1. In particular, antagomirs, antagonists or oligonucleotides of the invention include oligonucleotides comprising a sequence substantially complementary to nucleotides selected from the group of SEQ IDs 1-10 as set out in Table 1, or a subset of nucleotides thereof sufficient to inhibit the expression or activity of one or more of said miRNA sequences SEQ ID NOs 1-10. The invention includes antisense oligonucleotides or antagomirs comprising one or more sequence selected from the group of those set out in Table 2, or as set out in SEQ ID NOS: 11-15.

The one or more antagomir or oligonucleotide of the invention may comprise at least one modified nucleotide. In a particular aspect, the antagomirs, nucleic acids and oligonucleotides of the present invention may be modified, either by manipulation of the chemical backbone of the nucleic acids or by covalent or non-covalent attachment of other moieties. In each or any case, such manipulation or attachment may serve to modify the stability, cellular, tissue or organ uptake, or otherwise enhance efficacy of the nucleic acids and oligonucleotides. In further aspects of the invention, the antagomirs or oligonucleotides may be covalently linked to other molecules, including but not limited to polypeptides, carbohydrates, lipid or lipid-like moieties, ligands, chemical agents or compounds, which may serve to enhance the uptake, stability or to target the oligonucleotides. The oligonucleotides or antagomirs of the present invention may be combined with oligonucleotides directed to other targets, by mixture or by non-covalent or covalent attachment.

The skilled artisan can readily utilize any of several strategies to facilitate and simplify the selection process for nucleic acids and oligonucleotides effective in inhibition of one or more miRNA Target(s), as selected from miR-19, miR-20, miR-26, miR-92, miR-148 and miR-223. Predictions of the binding energy or calculation of thermodynamic indices between an oligonucleotide and a complementary sequence in an mRNA molecule may be utilized (Chiang et al. (1991) J. Biol. Chem. 266:18162-18171; Stull et al. (1992) Nucl. Acids Res. 20:3501-3508). Antisense oligonucleotides may be selected on the basis of secondary structure (Wickstrom et al (1991) in Prospects for Antisense Nucleic Acid Therapy of Cancer and AIDS, Wickstrom, ed., Wiley-Liss, Inc., New York, pp. 7-24; Lima et al. (1992) Biochem. 31:12055-12061). Schmidt and Thompson (U.S. Pat. No. 6,416,951) describe a method for identifying a functional antisense agent comprising hybridizing an RNA with an oligonucleotide and measuring in real time the kinetics of hybridization by hybridizing in the presence of an intercalation dye or incorporating a label and measuring the spectroscopic properties of the dye or the label's signal in the presence of unlabelled oligonucleotide. In addition, any of a variety of computer programs may be utilized which predict suitable antisense oligonucleotide or antagomir sequences or antisense targets utilizing various criteria recognized by the skilled artisan, including for example the absence of self-complementarity, the absence hairpin loops, the absence of stable homodimer and duplex formation (stability being assessed by predicted energy in kcal/mol). Examples of such computer programs are readily available and known to the skilled artisan and include the OLIGO 4 or OLIGO 6 program (Molecular Biology Insights, Inc., Cascade, Colo.) and the Oligo Tech program (Oligo Therapeutics Inc., Wilsonville, Oreg.).

In addition, antisense oligonucleotides suitable in the present invention may be identified by screening an oligonucleotide library, or a library of nucleic acid molecules, under hybridization conditions and selecting for those which hybridize to the target RNA or nucleic acid (see for example U.S. Pat. No. 6,500,615). Mishra and Toulme have also developed a selection procedure based on selective amplification of oligonucleotides that bind target (Mishra et al (1994) Life Sciences 317:977-982). Oligonucleotides may also be selected by their ability to mediate cleavage of target RNA by RNAse H, by selection and characterization of the cleavage fragments (Ho et al (1996) Nucl Acids Res 24:1901-1907; Ho et al (1998) Nature Biotechnology 16:59-630). Generation and targeting of oligonucleotides to GGGA motifs of RNA molecules has also been described (U.S. Pat. No. 6,277,981).

Inhibition of miRNA Target(s) expression can be measured in ways which are routine in the art, for example by RT-PCR analysis, Northern blot assay of RNA expression or Western blot assay of protein expression (e.g., of tumor suppressor gene sequences) as well known to the skilled artisan. Effects on cell proliferation or tumor cell growth can also be measured, in vitro or in vivo, in cell, tumor or animal model systems, by methods well known to the skilled artisan, including as taught in the examples of the instant application. Similarly, inhibition of miRNA Target(s) activity, particularly tumor suppressor gene expression activity may be measured.

"Substantially complementary" is used to indicate a sufficient degree of complementarity such that stable and specific binding occurs between the DNA or RNA target and the oligonucleotide or nucleic acid. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility or expression, and there is a sufficient degree of complementarity to avoid non-specific binding of the oligonucleotide to non-target sequences under physiological conditions in the case of in vivo assays or therapeutic treatment or, in the case of in vitro assays, under conditions in which the assays are conducted.

In the context of this invention, the term "oligonucleotide" refers to an oligomer or polymer of nucleotide or nucleoside monomers consisting of naturally occurring bases, sugars and intersugar (backbone) linkages. Oligonucleotide includes oligomers comprising non-naturally occurring monomers, or portions thereof, which function similarly and such modified or substituted oligonucleotides may be preferred over native forms because of for example, enhanced cellular uptake and increased stability against nucleases. The oligonucleotides of the present invention may contain two or more chemically distinct regions, each made up of at least one nucleotide, for instance, at least one region of modified nucleotides that confers one or more beneficial properties (for example, increased nuclease resistance, increased uptake into cells, increased binding affinity for the RNA target) and a region that is a substrate for enzymes capable of cleaving RNA:DNA or RNA:RNA hybrids (for example, RNase H—a cellular endonuclease which cleaves the RNA strand of an RNA:DNA duplex).

In a preferred embodiment, the region of the oligonucleotide or antagomir which is modified to increase miRNA binding affinity comprises at least one nucleotide modified at the 2' position of the sugar, most preferably a 2'-O-alkyl, 2'-O-alkyl-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. In another preferred embodiment, the oligonucleotide is modified to enhance nuclease resistance. Cells contain a variety of exo- and endo-nucleases which can degrade nucleic acids. A number of nucleotide and nucleoside modifications have been shown to confer relatively greater resistance to nuclease digestion. Oligonucleotides which contain at least one phosphorothioate modification are presently more preferred (Geary, R. S. et al (1997) Anticancer Drug Des 12:383-93; Henry, S. P. et al (1997) Anticancer Drug Des 12:395-408; Banerjee, D. (2001) Curr Opin Investig Drugs 2:574-80). In some cases, oligonucleotide modifications which enhance target binding affinity are also, independently, able to enhance nuclease resistance.

Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones. The amide backbones disclosed by De Mesmaeker et al. (1995) Acc. Chem. Res. 28:366-374) are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., Science, 1991, 254, 1497). Oligonucleotides may also contain one or more substituted sugar moieties. Preferred oligonucleotides comprise one of the following at the 2' position: OH, SH, $SCH_3$, F, OCN, heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. Similar modifications may also be made at other positions on the oligonucleotide, particularly the 3' position of the sugar on the 3' terminal nucleotide and the 5' position of 5' terminal nucleotide.

Oligonucleotides or antagomirs may also include, additionally or alternatively base modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (5-me-C) (Sanghvi, Y. S., in Crooke, S. T. and Lebleu, B., eds., Antisense Research and Applications, CRC Press, Boca Raton, 1993, pp. 276-278), 5-hydroxymethylcytosine (HMC), glycosyl HMC and gentobiosyl HMC, as well as synthetic nucleobases, including but not limited to, 2-aminoadenine, 2-thiouracil, 2-thiothymine, 5-bromouracil, 5-hydroxymethyluracil, 8-azaguanine, 7-deazaguanine (Kornberg, A., DNA Replication, W.H. Freeman & Co., San Francisco, 1980, pp 75-T7; Gebeyehu, G., et al., 1987, Nucl. Acids Res. 15:4513). A "universal" base known in the art, e.g., inosine, may be included.

Another modification of the oligonucleotides or antagomirs of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al. (1989) Proc. Natl. Acad. Sci. USA 86: 6553), cholic acid (Manoharan et al. (1994) Bioorg. Med. Chem. Let. 4:1053), a thioether, for example, hexyl-5-tritylthiol (Manoharan et al. (1992) Ann. N.Y. Acad. Sci. 660: 306; Manoharan et al. (1993) Bioorg. Med. Chem. Let. 3: 2765), a thiocholesterol (Oberhauser et al. (1992) Nucl. Acids Res. 20:533), an aliphatic chain, for example, dodecandiol or undecyl residues (Saison-Behmoaras et al. (1991) EMBO J. 10:111; Kabanov et al. (1990) FEBS Lett. 259: 327; Svinarchuk et al. (1993) Biochimie 75:49), a phospholipid, a polyamine or a polyethylene glycol chain (Manoharan et al. (1995) Nucleosides & Nucleotides 14:969). Oligonucleotides comprising lipophilic moieties, and methods for preparing such oligonucleotides are known in the art, for example, U.S. Pat. Nos. 5,138,045, 5,218,105 and 5,459, 255. Farrel and Kloster (U.S. Pat. No. 6,310,047) describe the enhancement of delivery and of in vivo nuclease resistance of antisense oligonucleotides using high affinity DNA binding polynuclear platinum compounds. It is not necessary for all positions in a given oligonucleotide or antagomir to be uniformly modified, and more than one of the aforementioned modifications may be incorporated in a single oligonucleotide or even at a single nucleoside within an oligonucleotide.

The oligonucleotides and antagomirs in accordance with this invention preferably are from about 8 to about 50 nucleotides in length. Particularly preferred oligonucleotides are from 10 to 30 nucleotides in length, particularly preferred are from 15 to 25 nucleotides. In the context of this invention it is understood that this encompasses non-naturally occurring oligomers as hereinbefore described, having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the skilled artisan. It is also well known to use similar techniques to prepare other oligonucleotides such as the phosphorothioates and alkylated derivatives.

The possibilities both diagnostic and therapeutic that are raised by the recognition and understanding of the role and activity of the miRNA Target(s) in oncogenesis and leukemogenesis and their collective expression in tumor/cancer cells, derive from the fact that the miRNA appear to participate in direct and causal interaction(s) with cancer-relevant genes including tumor suppressor genes, and have activity in inducing or facilitating cancer cell proliferation or maintenance. As suggested earlier and elaborated further on herein, the present invention contemplates pharmaceutical intervention in the cascade of reactions in which the miRNAs Target(s) are involved or implicated, to modulate the activity initiated by the miRNAs.

Methods for inhibiting expression of one or more miRNA particularly selected from miR-19, miR-20, miR-26, miR-92, miR-148 and miR-223 are thus provided. In particular, a method of inhibiting the expression of one or more miRNAs indicated as relevant in the invention is provided, comprising contacting cells which express one or more miRNAs with an effective amount of the antagomir or oligonucleotide of the present invention whereby expression or activity of said one or more miRNAs is inhibited.

The invention further includes a method of treating or preventing a condition, such as cancer or other hyperproliferative disorder, associated with the expression of the miRNAs of the invention or heightened expression of said miRNAs in a mammal comprising administering to said mammal a therapeutically effective amount of a compound or agent which inhibits the expression or activity of the miRNAs, particularly miR-19, miR-20, miR-26, miR-92, miR-148 and/or miR-223. In one aspect of this method, said compound or agent is an antisense oligonucleotide or antagomir which specifically hybridizes to one or more miRNA of miR-19, miR-20, miR-26, miR-92, miR-148 and miR-223.

Assays

The diagnostic and medical utility of the present invention extends to the use of the present miRNA Target(s) in assays to screen for or evaluate cancer, malignancy, lymphoma, and/or leukemia in a mammal, particularly a human patient. The present invention thus includes an assay system which may be prepared in the form of a test kit for the quantitative analysis of the extent of the presence of the miRNAs hereof, or to identify drugs or other agents that may mimic or block their activity.

In addition, a method is provided for identifying compounds or agents which inhibit the expression of one or more miRNAs associated with cancer comprising the steps of:
(a) incubating a cell expressing an miRNA selected from miR-19, miR-20, miR-26, miR-92, miR-148 and miR-223 in the presence and absence of a candidate compound or agent; and
(b) detecting or measuring the expression or activity of said miRNA selected from miR-19, miR-20, miR-26, miR-92, miR-148 and miR-223 in the presence and absence of a candidate compound or agent,
whereby a decrease in the expression of said miRNA selected from miR-19, miR-20, miR-26, miR-92, miR-148 and miR-223 in the presence of said candidate compound or agent versus in the absence of said candidate compound or agent indicates that said compound or agent inhibits the expression of miRNA selected from miR-19, miR-20, miR-26, miR-92, miR-148 and miR-223.

In an aspect of the method, the expression or activity of said one or more miRNA is assessed by determining the amount of said miRNA, the activity or expression of one or more miRNA target tumor suppressor gene, or the growth or viability of a leukemia or lymphoma cell expressing said miRNA. Exemplary such methods are provided herein, including in the examples and otherwise are known to and/or within the capability of one skilled in the art. miRNA expression may be determined using, for example RT-PCR assays. For example, the one or more miRNA target tumor suppressor gene(s), eg selected from Pten, Bim/Bcl2l11, Phf6, Ikzf1, Nf1 and Fbxw7, may be monitored to determine and evaluate miRNA expression or activity. Alternatively, a leukemia or lymphoma cell, such as a T-ALL patient cell sample or T-ALL cell line, may be evaluated for growth in determining miRNA activity or expression. Animal models may also be utilized.

Cancer, including lymphoma or leukemia may be assessed or monitored by determining expression of one or more miRNAs, particularly selected from miR19, miR20, miR26, miR92, miR148 and/or miR223. The invention thus includes a method for detecting or evaluating a malignancy, including a hematological malignancy, in a mammal comprising:
(a) obtaining a sample of blood or blood cells from said mammal;
(b) measuring the expression or activity of one or more miRNA selected from miR-19, miR-20, miR-26, miR-92, miR-148 and miR-223; and
(c) comparing the expression or activity of said one or more miRNA to that in or from a reference sample;
wherein the expression or activity of at least one of said one or more miRNA is increased relative to the reference sample.

A method is contemplated and provided for detecting or evaluating cancer in a mammal comprising:
(a) obtaining a cellular sample from said mammal;
(b) measuring the expression or activity of at least two miRNAs selected from miR-19, miR-20, miR-26, miR-92, miR-148 and miR-223 in said sample; and
(c) comparing the expression or activity of said at least two miRNAs to that in or from a reference sample;
wherein the expression or activity of at least two of said miRNAs is increased relative to the reference sample.

In an aspect of the above methods, the expression or activity of two or more miRNAs is measured, compared, and increased. In one aspect of the above methods, the expression or activity of three or more miRNAs is measured, compared, and increased. In a further aspect, the cancer is selected from the group of pancreatic cancer, lung cancer, skin cancer, urinary tract cancer, bladder cancer, liver cancer, thyroid cancer, colon cancer, intestinal cancer, leukemia, lymphoma, neuroblastoma, glioblastoma, head and neck cancer, breast cancer, ovarian cancer, stomach cancer, gastrointestinal cancer, esophageal cancer and prostate cancer. In a particular aspect, the cancer is a hematological malignancy, particularly selected from T-cell acute lymphoblastic leukemia (T-ALL), B-cell acute lymphoblastic leukemia (B-ALL), diffuse large B-cell lymphoma (DLBCL) and Burkitt's lymphoma. In a particular aspect the cancer is a leukemia, particularly T-ALL.

In vivo animal models of cancer or animal xenograft studies may be utilized by the skilled artisan to further or additionally screen, assess, and/or verify the role of the miRNA(s) of the present invention and to assess, identify and characterize modulators of the miRNA(s), including antagomirs, of the present invention, including further assessing modulation of miRNA expression, modulation of miRNA target genes or proteins, and inhibiting tumor progression, growth, resistance and/or infiltration. Exemplary cancer or tumor model(s) are provided and utilized herein in the examples, including a murine model of NOTCH1-induced T-ALL (Pear W S et al (1996) J Exp Med 183(5): 2283-2291; Wendel N H G et al (2004) Nature 428(6980): 332-337). Suitable animal models include, but are not limited to models of various cancers and hyperproliferative conditions. Any suitable cancer model may be utilized. Exemplary and useful animal models of hematological malignancies include: follicular lymphoma model using Bcl2 transgene controlled by Vav gene regulatory sequences (VavP) (Egle A et al (2004) Blood 103(6): 2276-2283); lymphoid malignancy transgenic mouse model using c-myc oncogene coupled to the immunoglobulin mu or kappa enhancer (Adams J M et al (1985) Nature 318(6046):533-38).

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The miRNA Target(s) or its binding partner(s) can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

In a further embodiment of this invention, commercial test kits suitable for use by a medical specialist may be prepared to determine the presence or absence of predetermined miRNA activity or capability in suspected target or cancer cells. In accordance with the testing techniques discussed above, one class of such kits will contain at least the labeled miRNA or its binding partner, for instance a tumor suppressor gene, and directions, of course, depending upon the method selected, e.g., "competitive," and the like. The kits may also contain peripheral reagents such as buffers, stabilizers, etc.

Compositions

The present invention further contemplates therapeutic compositions useful in practicing the therapeutic methods of this invention. A subject therapeutic composition includes, in admixture, a pharmaceutically acceptable excipient (carrier) and one or more of an antagomir, oligonucleotide, miRNA Target antagonist, as described herein as an active ingredient. In a preferred embodiment, the composition comprises an agent capable of modulating the specific binding of the miRNAs of the present invention to their target(s) within a target cell, particularly a cancer cell or pre-cancerous cell.

The preparation of therapeutic compositions which contain antagomirs, oligonucleotides or miRNA antagonists as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An antagomir(s), oligonucleotide(s) or miRNA antagonist(s) can be formulated into the therapeutic composition as neutralized pharmaceutically acceptable salt forms. Pharmaceutically acceptable salts include the acid addition salts and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic antagomirs, oligonucleotides or miRNA antagonists-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of miRNA capacity desired. Precise amounts of active ingredient required to be administered depend on the judgment of the practitioner and are peculiar to each individual.

As used herein, "pg" means picogram, "ng" means nanogram, "ug" or "μg" mean microgram, "mg" means milligram, "ul" or "μl" mean microliter, "ml" means milliliter, "l" means liter.

The therapeutic compositions may further include an effective amount of the nucleic acid or oligonucleotide, and one or more of the following active ingredients or agents: a chemotherapeutic agent, a radiotherapeutic agent, an immunomodulatory agent, an anti-mitotic agent.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration. For oral administration, it has been found that oligonucleotides with at least one 2'-substituted ribonucleotide are particularly useful because of their absortion and distribution characteristics. U.S. Pat. No. 5,591,721 (Agrawal et al.) and may be suitable for oral administration. Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral, intrathecal or intraventricular administration may include sterile aqueous solutions which may also contain buffers, diluents and other suitable additives. In addition to such pharmaceutical carriers, cationic lipids may be included in the formulation to facilitate oligonucleotide uptake. One such composition shown to facilitate uptake is Lipofectin (BRL Bethesda, Md.).

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual oligonucleotides, and can generally be calculated based on IC50s or EC50s in in vitro and in vivo animal studies. For example, given the molecular weight of compound (derived from oligonucleotide sequence and chemical structure) and an effective dose such as an IC50, for example (derived experimentally), a dose in mg/kg is routinely calculated.

As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the nucleic acid sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, R1.1, B-W and L-M cells, African Green Monkey kidney cells (e.g., COS1, COS 7, BSC1, BSC40, and BMT10), insect cells (e.g., Sf9), and human cells and plant cells in tissue culture.

It will be understood that not all vectors, expression control sequences and hosts will function equally well to express the nucleic acid sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular nucleic acid sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Synthetic DNA/RNA sequences allow convenient construction of genes which will express miRNA analogs or "muteins". Alternatively, DNA encoding muteins can be made by site-directed mutagenesis of native RNA, genes or cDNAs, and muteins can be made directly using conventional polypeptide synthesis. A general method for site-specific incorporation of unnatural amino acids into proteins is described in Christopher J. Noren, Spencer J. Anthony-Cahill, Michael C. Griffith, Peter G. Schultz, Science, 244: 182-188 (April 1989). This method may be used to create analogs with unnatural amino acids.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated. Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

MicroRNAs (miRNAs) are ubiquitous regulators of biological processes involved in normal development, in differentiation and in diseases, including cancer. They act by regulating gene expression at the transcriptional and translational levels (Bartel, 2004). The 17~92 cluster of miRNAs is highly expressed in hematopoietic cancers and enhances lymphoproliferation and c-Myc-induced leukemogenesis/lymphomagenesis in vivo (He, et al., 2005) (Xiao, et al., 2008). The 17~92 cluster and its paralogues are also expressed in diverse solid tumors, including those derived from breast, colon, lung, pancreas, prostate, and stomach (Volinia, et al., 2006) (Petrocca, et al., 2008).

Using an in vitro hematopoietic transformation assay, we determined that, of the miRNAs in the 17~92 cluster, surprisingly, overexpression of only miR-19 protects interleukin-3 (IL3)-deprived FL5-12 lymphocytes from apoptotic death. We also: (1) demonstrated that miR-19 is highly overexpressed in aggressive leukemias and lymphomas, including T-cell acute lymphoblastic leukemia (T-ALL), B-cell acute lymphoblastic leukemia (B-ALL), diffuse large B-cell lymphoma (DLBCL) and Burkitt's lymphoma but not in follicular B-cell lymphoma; (2) identified a novel (although likely rare) chromosomal rearrangement associated with T-ALL that juxtaposes the miR-17~92 cluster with the T-cell receptor locus [t(13;14)(q32;q11)] and that occurs together with a second translocation that results in the expression of a constitutively activated/truncated (exons 29-34) form of NOTCH1; and (3) demonstrated that miR-19 promotes both NOTCH1-induced T-ALL and c-Myc-induced Burkitt's lymphoma.

Using an unbiased genetic screen for shRNAs that recapitulate miR-19's activity in the hematopoietic transformation assay, we identified eight genes (five with miR-19 seed sequences) as miR-19 targets involved in lymphocyte survival: Bim (pro-apoptotic), Pten (tumor suppressor), Prkaa1 (the α subunit of AMP-activated kinase), Ppp2r5e (the ε isoform of PP2A) and Dock5 (dedicator of cytokinesis-5), all of which are direct miR-19 targets, and Fox01 and Fox03 (Fox transcription factors) and Bnip3 (a regulator of Rheb/mTOR and Bcl2 binding protein), which are not.

Using quantitative real-time polymerase chain reaction (qRT-PCR), reporter assays in combination with mutational analysis of the miR-19 binding sites and an miR-19 antagomir, we confirmed that expression of Bim, Pten, Prkaa1 and Pppp2r5e is directly regulated, in lymphocytes, by miR-19 and that each gene contributes to lymphocyte survival in the hematopoietic transformation assay. In addition, miR-19 produced a clear reduction in PPP2R5E, PRKAA1 and BIM, although not in PTEN, protein levels, while the mirR-19 antagomir produced increases in the levels of the miR-19 target proteins PPP2R5E, PRKAA1, BIM and PTEN. (The murine Dock5 gene does not contain the miR-19 seed match present in the human gene and is not a target of miR-19 in FL5-12 cells.)

These data demonstrate that miR-19 coordinates a PI-3K-related program of cell survival and that measuring miR-19 expression can be used for the diagnosis of leukemias and lymphomas, for predicting response to specific therapeutic regimens and/or for monitoring response to therapy. They further indicate antagonists/antagomirs of miR-19 as effective therapeutics against cancers, including hematologic malignancies, overexpressing miR-19.

Figure 1:
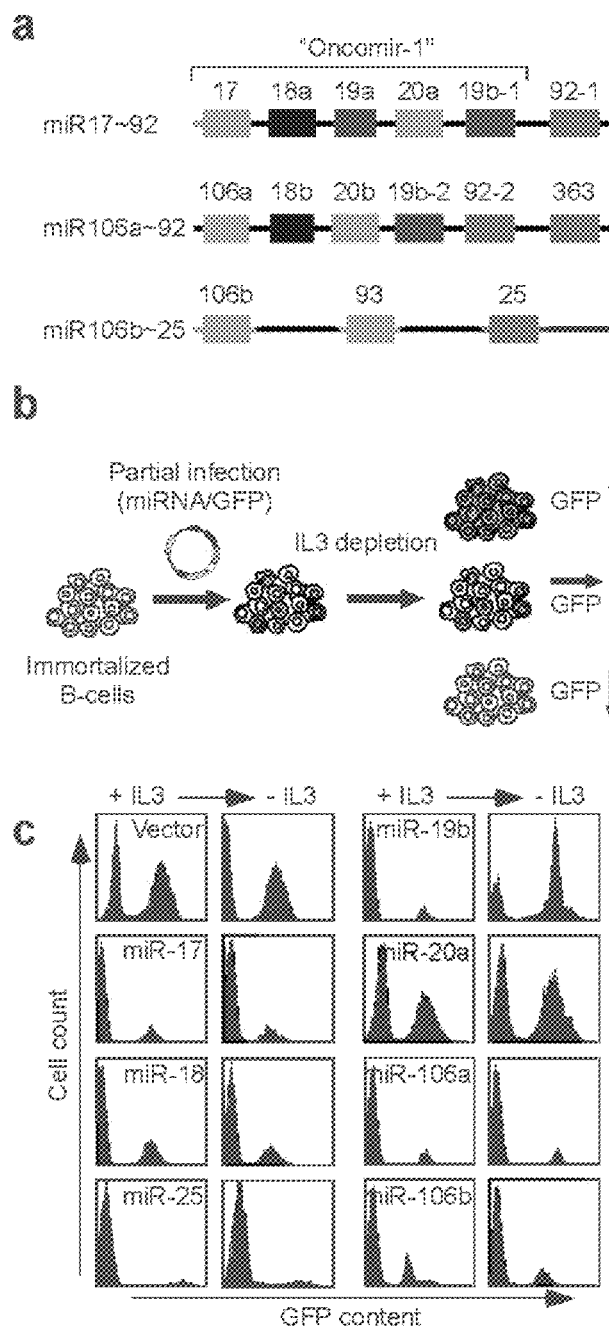
FIG. 1. miR-19 enhances cytokine-independent survival in vitro. (a) Genomic organization of the 17~92 cluster (including "oncomir-1") and its paralogues. miRNAs shown in identical color share common seed sequences. (b) Schematic of the competition assay for cytokine-independent survival of immortalized FL5-12 lymphocytes. (c) FACS profiles showing that FL5-12 cells transduced with miR-19 expand upon IL3 depletion, while populations transduced with empty vector or the other 17~92 miRNAs do not.
Figure 2:
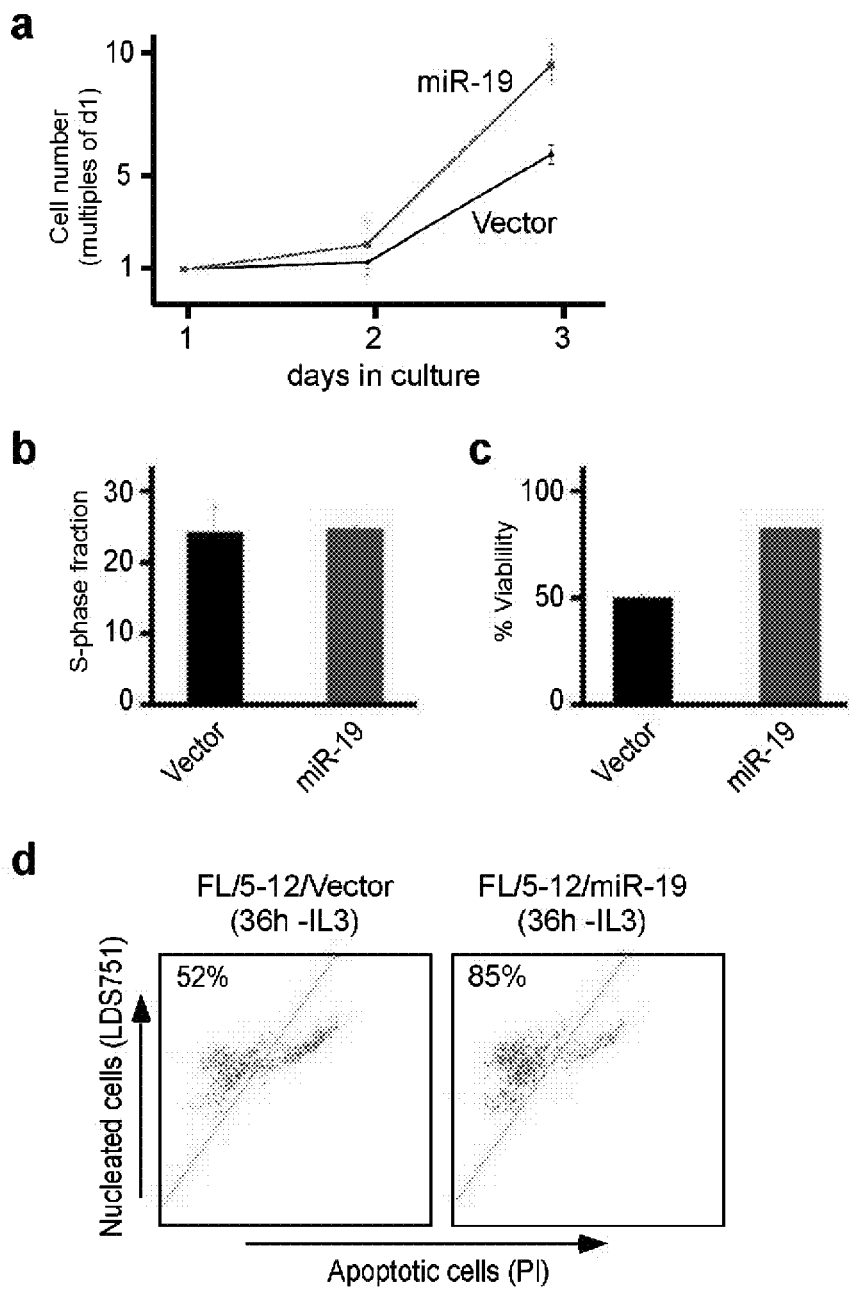
FIG. 2. miR-19 enhances lymphocyte survival in vitro. (a) Growth curve of FL5-12 cells in complete media expressing empty vector (vector) or miR-19 (miR-19) normalized to cell number on day 1 ($p<0.009$) (b) S-phase fraction in synchronized FL5-12 cells 24 h after release (Vector: 24%±3%; miR-19: 24.5%±0.5; $p=0.8$). (c) Viability in FL5-12 cells transduced with vector or miR-19 and withdrawn from IL3 for 48 h (Vector: mean 49%±1%; miR-19: 82%±1.5%; $p<6exp-06$). (d) Representative FACS profiles measuring cell viability in FL5-12/vector cells compared to FL5-12/miR-19. The percentage of viable cells after IL3 depletion is indicated.
Figure 3:
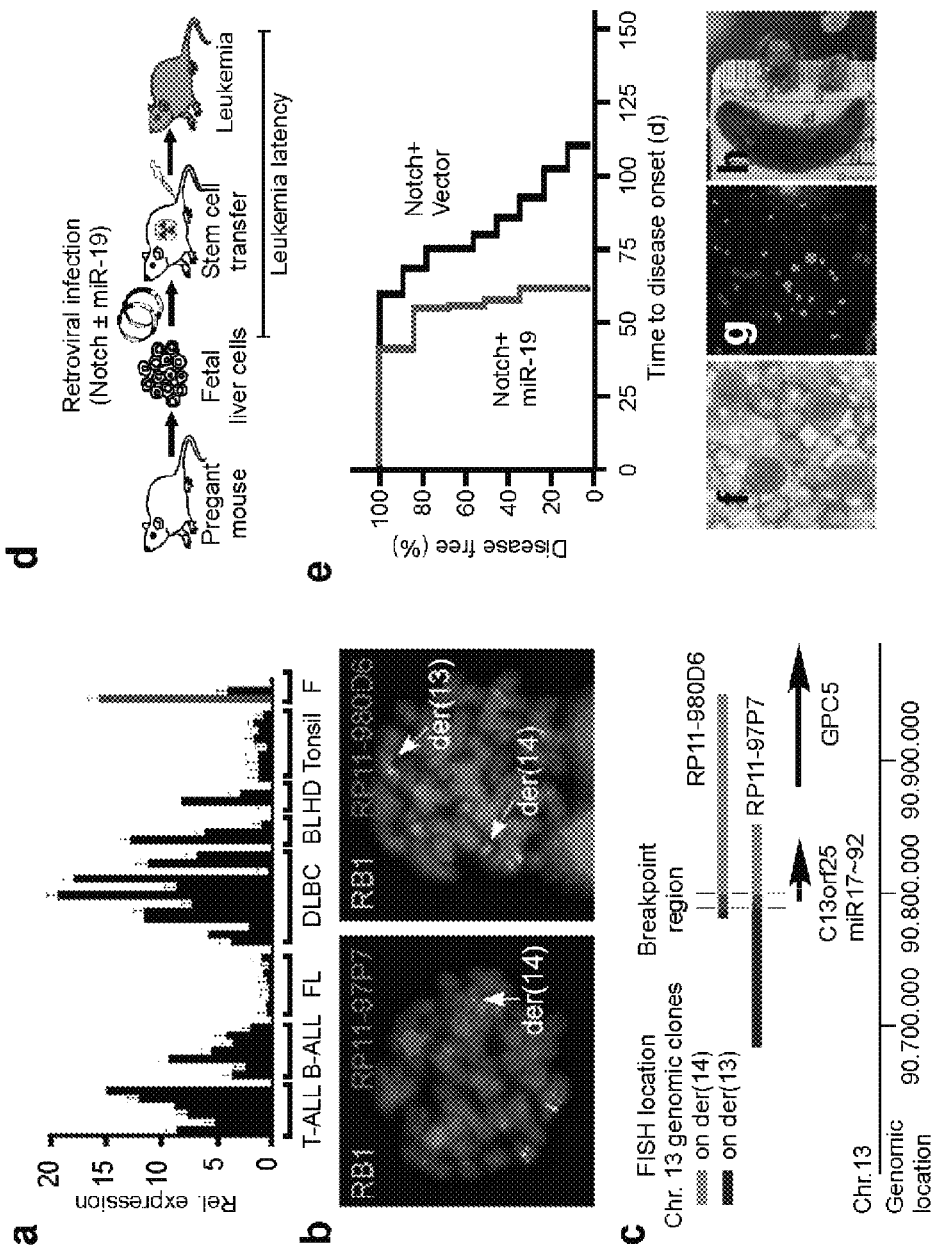
FIG. 3. miR-19 is a human oncogene and target of a novel translocation in T-All. (a) qRT-PCR measurement of miR-19 expression in a panel of human lymphoid malignancies: (T-/B-ALL) T- and B-cell acute lymphoblastic leukemia; (FL) follicular lymphoma; (DLBCL) diffuse large B-cell lymphoma; (BL) Burkitt's lymphoma; (HD) Hodgkin's disease; (Tonsil) lymphocytes from reactive tonsils; (F) FL5-12 cells, parental (black bar) or transduced with miR-19 (red bar); values shown are mean±SD. (b) Double-color FISH analysis of t(13;14)(q32;q11) using a RB1 probe (green) in 13q14 and genomic clones RP11-97P7 and RP11-980D6 overlapping the 17~92 locus in 13q32 (red). (c) Graphic representation of FISH results. (d) Mouse model of Notch-induced T-ALL (e) Kaplan-Meier analysis of leukemia-free survival after hematopoietic progenitor cell (HPC) transplantation with Notch-ICN+miR-19 (red; n=6) or with Notch-ICN+vector (black; n=9). (f)-(h) Representative microphotographs of Notch/miR-19 induced ALL. (f) Leukemic blasts on blood smear. (g) Effacement of the bone marrow by miR-19/green fluorescent protein (GFP)-expressing leukemic cells. (h) Splenomegaly and lymphomas. The pathologic appearance of Notch1-induced leukemia is identical (not shown).
Figure 6:
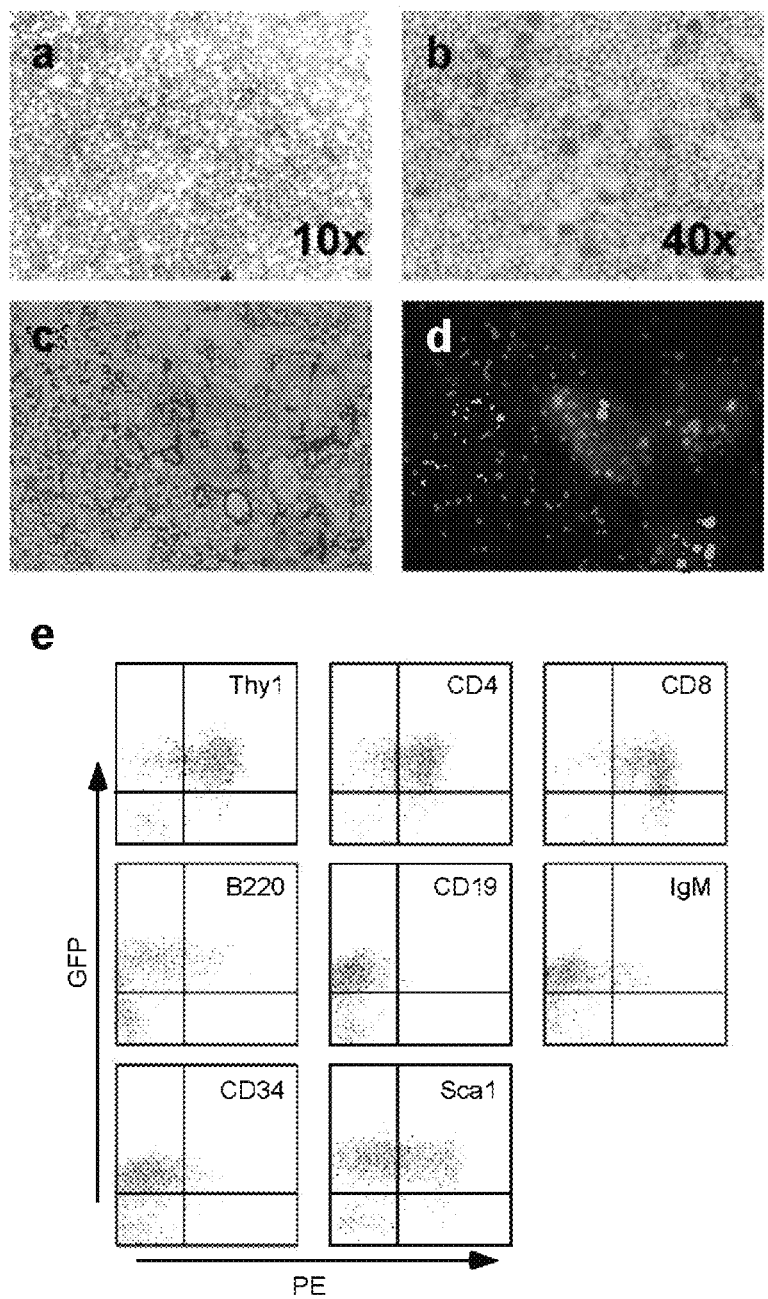
FIG. 6. Characterization of miR-19/Notch-1 induced T-ALL. (a) Representative microphotograph of a blood smear from a leukemic animal at low (10×) magnification. (b) High (40×) magnification of leukemic blasts. (c) Unstained bone marrow smear. (d) GFP fluorescence identifies widespread infiltration of marrow by leukemic cells. (e) Immunophenotyping of GFP positive ALL cells using PE-labeled antibodies to the indicated surface markers. Leukemia arising in Notch1-transduced HPCs showed the same features (not shown) but a longer latency.

The Oncogenic Activities of miR-19 are Unique Among the miRNAS of the 17~29 Cluster and its Paralogues An established in vitro assay of hematopoietic transformation (Plas, Talapatra, Edinger, Rathmell, & Thompson, 2001) was used to identify the key oncogenic activities within the 17~92 cluster and its paralogues. All miRNAs representing families of unique seed sequences, specifically miR-17, miR-18a, miR-19b-1 (miR-19), miR-20a, miR-106a, miR-106b and miR-25 were tested (FIG. 1a). The assay is based on the IL3 dependence of FL5-12 lymphocytes, which undergo apoptosis when removed from IL3. In competition experiments, FL5-12 cells were partially transduced with GFP plus individual miRNAs or empty vector and these mixed populations were monitored by fluorescence-activated cell sorting (FACS) for changes in their relative proportions (FIG. 1b). FL5-12 cells expressing miR-19 were rapidly enriched over parental cells upon IL3 depletion, and none of the other miRNAs were associated with this protective effect (miR-19: p<0.002, all other miR-NAs and vector p>0.05 by t-test) (FIG. 1c). This effect was primarily due to protection from apoptosis and did not significantly change cell cycle kinetics (FIG. 2). Hence, within the 17~92 cluster and its paralogues, miR-19 has a distinct ability to enhance lymphocyte survival in vitro.

miR-19 is Highly Expressed in Certain Leukemias and Lymphomas and is the Target of a Novel Chromosomal Rearrangement in T-Cell Leukemia Expression of miR-19 in human lymphatic malignancies was assessed. Compared to non-malignant lymphocytes from tonsils, there was a 5-17× increase in miR-19 expression in T-ALL and somewhat smaller increase in B-ALL (FIG. 3a). Moreover, a novel rearrangement was observed in T-ALL—a translocation, t(13;14)(q32;q11), that juxtaposes the miR-17~92 cluster with the T-cell receptor locus (TCRA/D) (FIGS. 3b and c and FIG. 4). This change occurs together with a second translocation—t(9;14)(q34;q11)— that affects the other TCRA/D allele and produces expression of a constitutively active and truncated form of Notch1 (exons 29-34) (FIG. 5) (Palermo, et al., 2006), (Ellisen, et al., 1991) (FIG. 5b: SEQ ID NO:18). miR-19 was also highly expressed in aggressive B-cell lymphomas such as DLBCL and Burkitt's lymphoma but less abundant in indolent follicular lymphomas. Notably, retroviral expression of miR-19 in the FL5-12 cells produced levels comparable to those in some tumor specimens (FIG. 3a). Thus, miR-19 is highly expressed in aggressive lymphatic cancers and is the target of a novel chromosomal rearrangement in T-cell leukemia.

miR-19 Drives the Development of Aggressive T- and B-Cell Lineage Malignancies In Vivo Can miR-19 drive the development of lymphatic malignancies in vivo? Based on the miR-19 expression and translocation data, miR-19 was assessed in a mouse model of T-ALL (Pear, et al., 1996). Briefly, most cases of T-ALL carry mutations in the Notch1 gene, and, like the t(9;14) (q34;q11) translocation, these generate the constitutively active intracellular domain of NOTCH1 (Notch-ICN) (Weng, et al., 2004). To test miR-19's ability to promote Notch-ICN-induced T-ALL in vivo, HPCs were adoptively transferred into irradiated recipients (FIG. 3d). Mice receiving HPCs expressing Notch-ICN and miR-19 rapidly succumbed to T-ALL, and all of these animals were moribund within two months. At the same time, 80% of the mice receiving HPCs expressing only Notch-ICN remained disease free (p=0.0003) (FIG. 3e). Pathology confirmed the diagnosis of T-ALL with abundant blasts on blood smears, infiltration of the marrow, spleen and lymph nodes, and exclusive expression of T-cell markers (FIG. 3f-h and FIG. 6). miR-19 exhibited similar effects in the EμMyc model of Burkitt's lymphoma, indicating its ability to co-operate with c-Myc by blocking p53-dependent apoptosis—as reported for the entire cluster (He, et al., 2005) (FIG. 7). Hence, miR-19 acts, in vivo, as an oncogene in aggressive malignancies arising from B- and T-cell lineages.

Identification of the Targets Responsible for miR-19's Oncogenic Activity

Target Prediction and Gene Expression Analysis

The molecular targets responsible for miR-19's oncogenic activity were determined. Initially, computational target identification and gene expression analyses were combined. Targetscan retrieved 938 human and 744 murine potential miR-19 targets. Gene expression profiles in FL5-12 cells transduced with miR-19 or vector showed only modest changes in expression [mean fold change of 0.2±a standard deviation (SD) of 0.39] (FIG. 8). Overall, expression levels of all predicted miR-19 targets, including the Pten tumor suppressor gene, were more reduced than other genes (p<2e-04, by the Kolmogorov-Smirnov test). However, there was no significant enrichment of miR-19 targets among genes showing more pronounced (1.5 or 2 SD) reductions in expression (p>0.46 at 2 SD; p>0.077 at 1.5 SD, Fisher's exact test) (FIG. 8).

Figure 9:
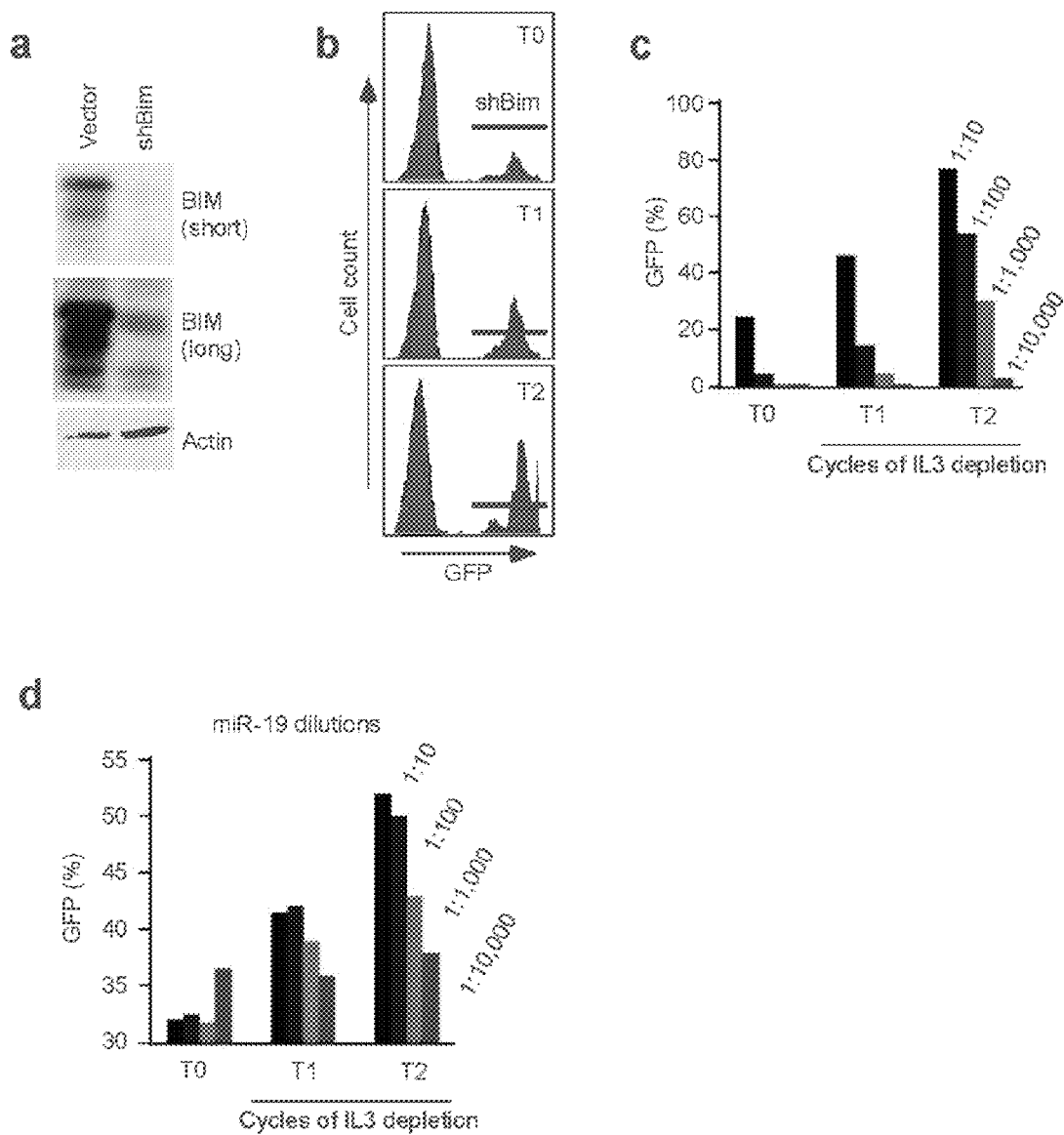
FIG. 9. Optimization Studies for the short hairpin RNA (shRNA) screen. (a) Immunoblot of FL5-12 cells showing knockdown of BIM/BCl2L11 protein (short and long exposures) by an shRNA against Bim compared to vector. (b) FL5-12 cells expressing the Bim shRNA and GFP are enriched in subsequent cycles of IL3 depletion and rescue. T0 is untreated; T1 is one cycle of IL3 depletion and IL3 rescue; T2 is two cycles. (c) Library reconstruction experiment in which the positive control shRNA linked to GFP is diluted with empty vector from 1:10 up to 1:10,000. Enrichment of shRNA- and GFP-expressing cells is readily detected at dilutions of 1:1,000 and possibly even at 1:10,000. (d) Library reconstruction experiment conducted as in (c) and using increasing dilutions of miR-19 to characterize in detail miR-19 in the screening assay. Based on these findings the library was constructed to a complexity of ~1,000 shRNAs per pool.

Short-Hairpin RNA Genetic Screen as an Unbiased Functional Assay for miR-19 Targets It was hypothesized that an unbiased genetic screen might be an alternative way to identify miR-19 targets involved in lymphocyte survival. Specifically, it was hypothesized that a shRNA screen (Paddison, et al., 2004) for genes whose knockdown phenocopies miR-19 in lymphocytes would identify the genes responsible for miR-19's activity. Control experiments were conducted using an shRNA against Bim (Bcl2L11), a known target of the 17~92 cluster (FIG. 9a-c). A screening protocol involving transduction of FL5-12 cells with pools of ~1,000 shRNAs and two cycles of IL3 depletion or continued passage in complete media (FIG. 10a) was devised. Custom half-hairpin arrays (Chang, Elledge, & Hannon, 2006) were used to measure changes in the abundance of shRNAs in treated (IL3⁻) versus untreated (IL3⁺) samples after one or two rounds of selection (T1 and T2). Unsupervised clustering showed good reproducibility between biological replicates (A-C; mean correlation r=0.60±0.17) and revealed a progressive shift in shRNAs with subsequent cycles of IL3 depletion (FIG. 10b). Statistical tools were used to identify biologically significant signals. Significance analysis of microarrays (SAM) identified changes in individual shRNAs (FIG. 10c), while gene set analysis (GSA) defined groups of shRNAs targeting the same genes. The GSA identified 14 genes, each targeted by at least two, and up to five, different shRNAs; the top 'hit' was the alpha subunit of AMP-activated kinase (Prkaa1), targeted by five independent shRNAs (FIG. 10d).

Validation of Putative miR-19 Targets Using Short-Hairpin RNAs

Candidate genes were initially validated using the same shRNA experimental system. Nearly all genes identified from the GSA analysis as well as protein-coding genes from the SAM analysis above an arbitrary threshold (≥1.65 fold increase, p<0.05) were included. In total, >70 genes and typically three shRNAs targeting each were re-tested. Ultimately, shRNAs targeting eight genes produced a survival benefit in FL5-12 cells depleted of IL3 [in triplicate experiments, p for vector (not shown)>0.2 and p for all eight shRNAs<0.05, t-test] (FIG. 10e). Strikingly, five of these genes harbored the miR-19 seed sequence. Besides the pro-apoptotic Bim, these were the tumor suppressor gene Pten, the alpha subunit of AMP-activated kinase (Prkaa1), the epsilon isoform of PP2A (Ppp2r5e) and the dedicator of cytokinesis-5 gene (Dock5). In addition, three genes that were not direct miR-19 targets, namely the FoxO transcription factors FoxO1 and FoxO3 and Bnip3, a regulator of Rheb/mTOR and Bcl2 binding protein, were also validated in this assay as targets of miR-19. Taken together, the results of an unbiased genetic screen for shRNAs that behave like miR-19 show a highly significant enrichment for genes that contain miR-19 binding sites (p<7.17e-07 Fisher's exact test) (FIG. 11a). Unlike the human Dock5 gene, the mouse gene is not predicted to be a miR-19 target, but calculation of the enrichment statistics for the murine genome confirmed high significance levels (p<3.2 exp-05 by Fisher's exact test) (FIG. 11b). Likely, the genes identified are functionally relevant targets of miR-19 in hematopoietic cell survival. Consequently, they represent potential therapeutic targets for the treatment of cancers, especially hematologic malignancies.

Figure 12:
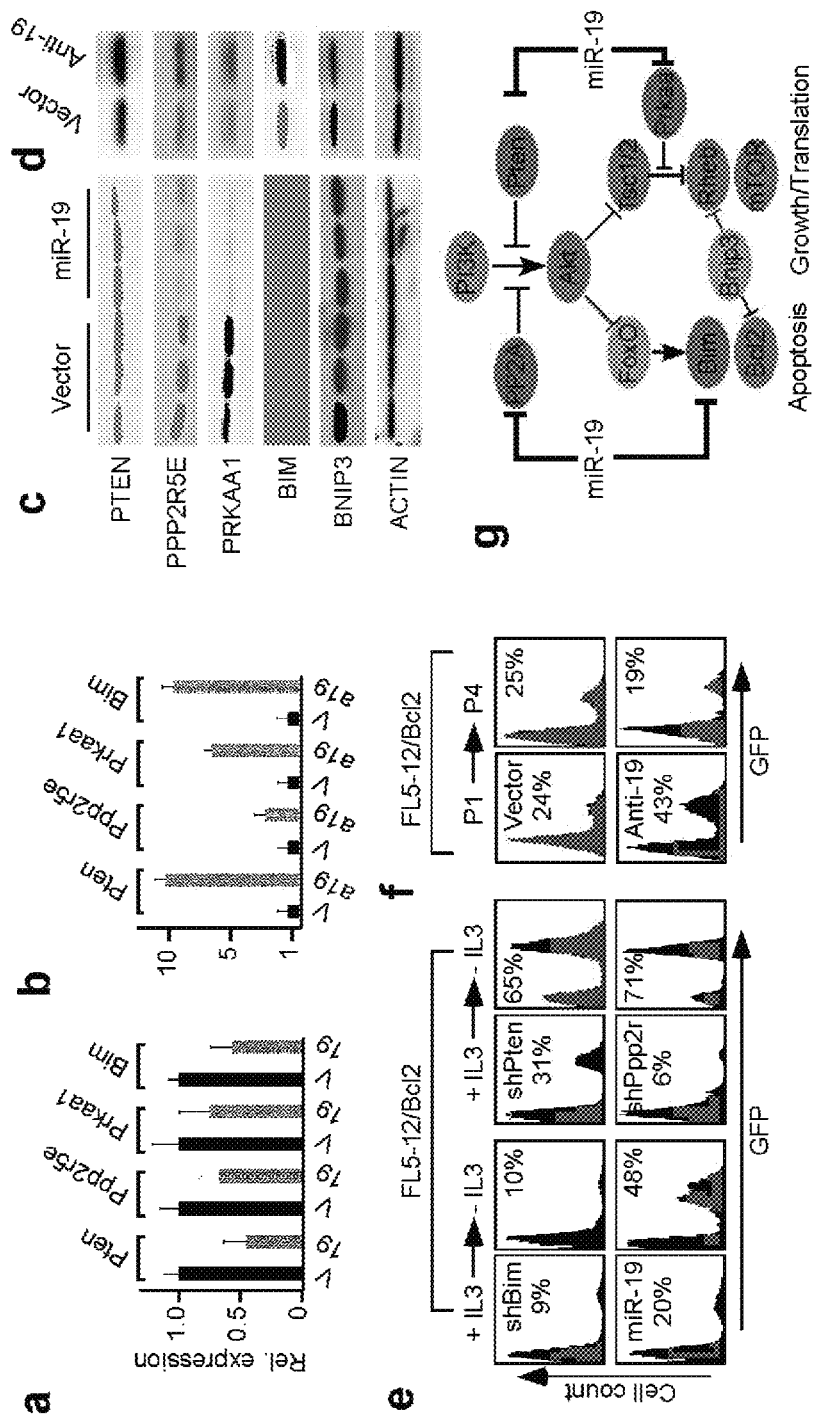
FIG. 12. the identified genes are actual and relevant targets of miR-19. (a) qRT-PCR for the indicated genes on cDNA prepared from vector (black bars) or miR-19 transduced (shaded bars) FL5-12 cells. Expression levels (mean±SD) are normalized to the vector controls (relative expression). (b) qRT-PCR comparing FL5-12 cells transduced with vector (black bars) and antagomirs to miR-19 (shaded bars) analyzed as above. (c) and (d) Immunoblot on lysates from vector, miR-19- (c) or antagomir-19- (d) transduced FL5-12 cells probed for the indicated proteins. (e) FACS profiles of FL5-12 cells co-expressing Bcl2 (FL5-12/Bcl2) and GFP and the indicated shRNAs or miR-19. Cells are shifted from complete (+IL3) to IL3 deficient media (—IL3) to assess Bcl2 independent effects on lymphocyte survival. (f) FACS analysis of FL5-12/Bcl2 cells transduced with GFP and antagomir (anti-19) or vector and grown in complete media. (g) Diagram indicating the multilevel control of PI3K survival signals by miR-19.
Figure 13:
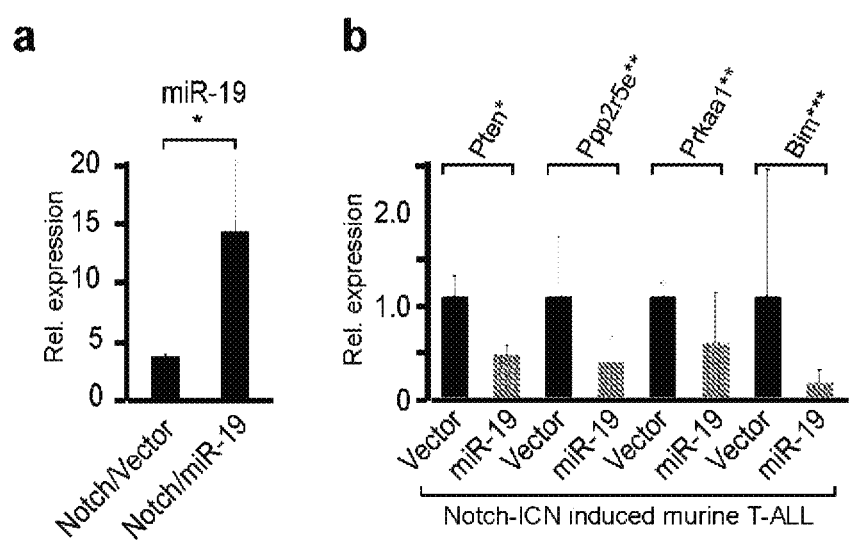
FIG. 13. miR-19 and target gene expression in murine T-ALL. (a) miR-19 expression is increased in T-ALL derived from HPCs transduced with Notch1 and miR-19 compared to Notch1 alone. (b) The mRNA expression of several target genes is reduced in murine T-ALL driven by Notch1 and miR-19 compared to Notch1 alone (*$p<0.05$; $p<0.1$; *$p>0.1$).
Figure 14:
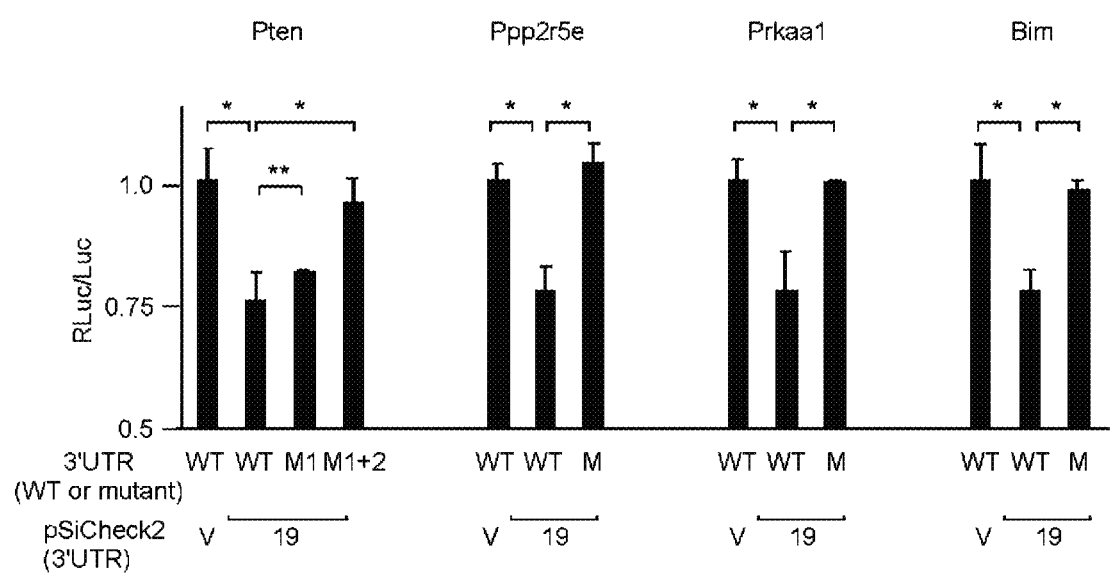
FIG. 14. Reporter assay for 3' untranslated region (3'UTR) repression by miR-19. The 3'UTR of the indicated genes was subcloned into a dual luciferase reporter construct (pSiCheck2) and inhibition of the 3'UTR by miR-19 is indicated as mean±SD ratio of Renila to Firefly luciferase activity (RLuc/Luc). WT indicates the wild type 3'UTR. M indicates the 3'UTR where the miR-19 binding site has been mutated. In the case of Pten, one site (M1) or both sites (M1+M2) were mutated [* indicates significant ($p<0.05$) changes; ** indicates non-significant ($p>0.05$) changes.]
Figure 15:
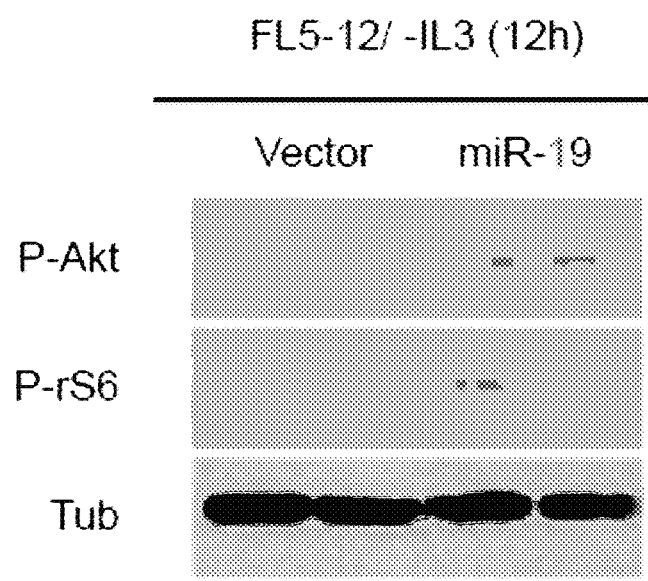
FIG. 15. miR-19 induces activation of Akt and ribosomal S6 phosphorylation. Immunoblot of FL5-12 cells transduced with vector or miR-19, withdrawn from IL3 for 12 hours and probed with the indicated antibodies.

Confirmation that miR-19 Regulates the Expression of the Genes Identified as miR-19 Targets Does miR-19 actually regulate the expression of the genes identified as targets of miR-19? qRT-PCR demonstrated that miR-19 produced up to 2× reductions in the mRNA levels of Pten, Ppp2r5r, Prkaa1 and Bim in FL5-12 cells and in murine T-ALL samples (FIG. 12a and FIG. 13). Reporter assays and mutagenesis of the miR-19 binding sites confirmed direct 3' untranslated region (UTR) inhibition via the miR-19 binding sites for these genes (FIG. 14). Conversely, an antagomir against miR-19 caused an increase in mRNA levels (FIG. 12b), and both miR-19 and the antagomir had measurable effects on protein levels. For example, miR-19 produced a clear reduction in PPP2R5E, PRKAA1, and BIM (FIG. 12c) and directly activated ribosomal S6 phosphorylation, a downstream readout of PI3K activity (FIG. 15). And while miR-19 had no detectable effect on PTEN protein, its mRNA was clearly decreased. The antagomir produced increases in all miR-19 target proteins including PTEN (FIG. 12d). As expected, neither miR-19 nor the antagomir had an effect on Bnip3 (FIGS. 12c and d). Also, the mouse Dock5 gene does not contain the seed match present in the human gene, and accordingly it is not a target in FL5-12 cells. The larger effects of the antagomir compared to miR-19 expression may indicate that these genes are tonically suppressed by endogenous miR-19 in proliferating cells. These findings confirm that the expression of Bim, Prkaa1, Pten and Ppp2r5e is regulated by miR-19 in lymphocytes.

Assessing the Relative Contribution of the miR-19 Targets to the Oncogenic Activity of miR-19

Figure 16:
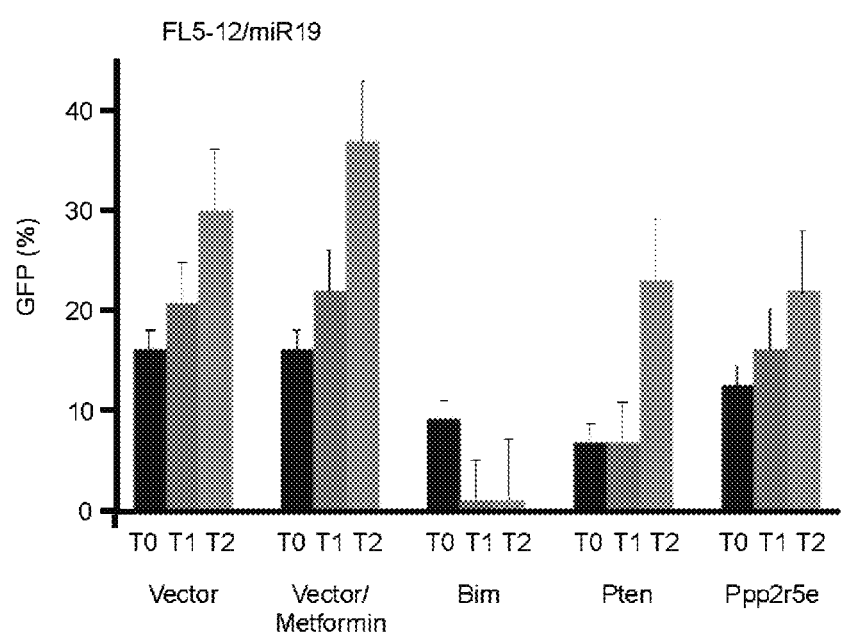
FIG. 16. Complementation experiments—cDNA expression. Summary of FACS results for enrichment of cells co-expressing miR-19/GFP and the indicated cDNAs or empty vector or treated with 1 μM metformin to activate AMP-kinase activity. T0 in presence of IL3, T1 and T2 subsequent time points following Il3 depletion. Standard error (SEM) is indicated; in all cases, p (for T2 vs. T0)<0.05. Expression of the pro-apoptotic BIM protein rapidly induced cell death in FL5-12 cells. Neither the other cDNAs nor metformin treatment abrogated miR-19's protective function.

The relative contribution of the novel miR-19 targets was assessed. The pro-apoptotic BIM protein opposes BCL2 and is an important regulator of lymphocyte survival (Bouillet, et al., 1999). To assess whether miR-19 has Bim-independent effects, complementation studies were conducted with FL5-12 cells engineered to stably express Bcl2 (FL5-12/Bcl2 cells). As expected, Bim shRNA conferred no additional benefit, whereas miR19 and the shRNAs against Pten and Pp2r5e showed continued enrichment in the presence of Bcl2 (FIG. 12e). Conversely, an antagomir against miR-19 produced anti-proliferative effects; FL5-12/Bcl2 cells expressing the antagomir were lost upon continued passage (FIG. 12f). Similarly, expression of miR-19 was associated with continued proliferation in the presence of metformin-activated AMP kinase or expression of Pten or Pp2r5e (FIG. 16). Hence, miR-19 acts through multiple target genes including regulators of PI3K-related survival signals in lymphocytes (FIG. 12g).

Materials and Methods

Cell Culture, Viability, Proliferation Assays and Vector Constructs

Figure 17:
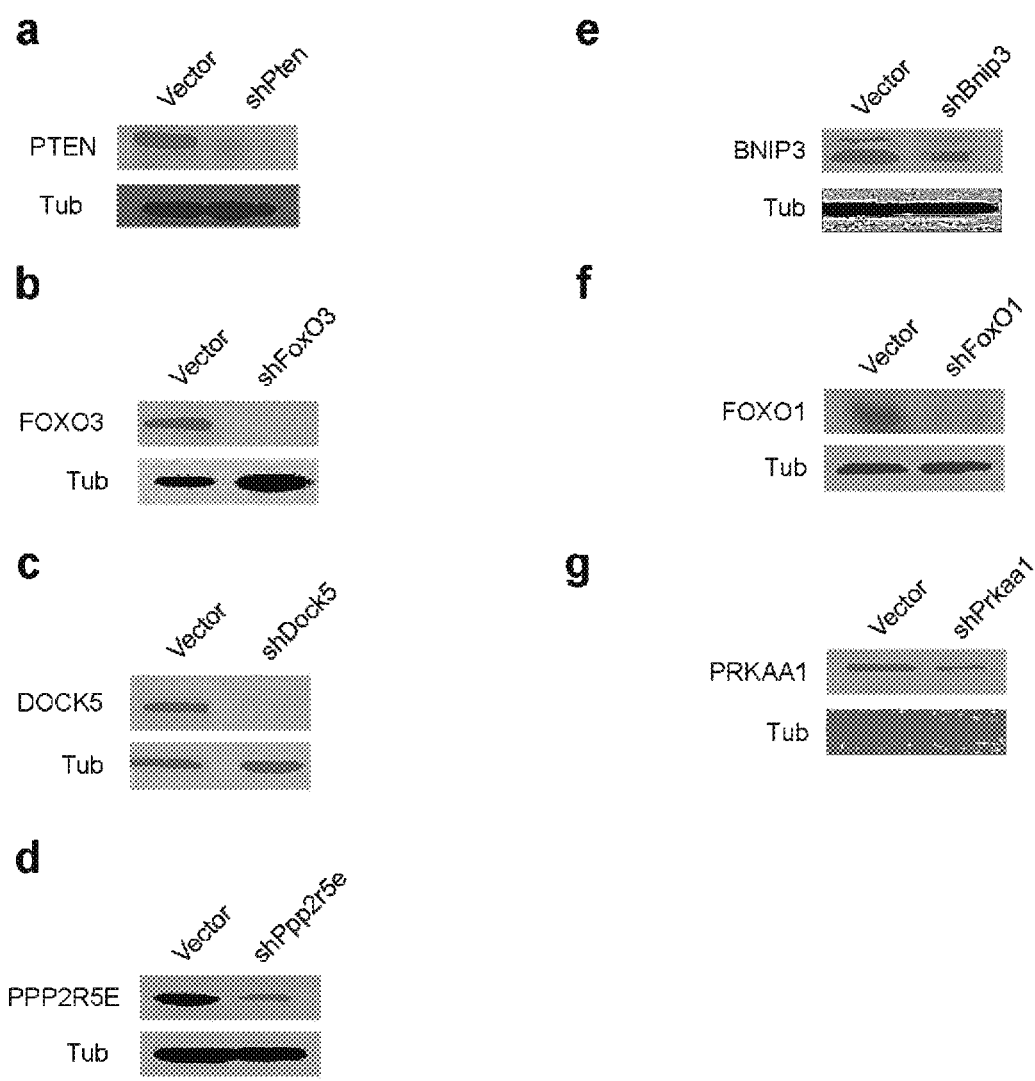
FIG. 17. Protein knockdown by shRNA constructs. (a)-(g) Immunoblot of cells transduced with the indicated shRNA constructs or empty vector and probed for the indicated proteins. Shown in each case is the most efficient shRNA of at least three shRNAs tested.

FL5-12 murine lymphocytes, IL3 depletion studies and viral transductions were as described (Mavrakis, et al., 2008) (Plas, Talapatra, Edinger, Rathmell, & Thompson, 2001). Cell cycle and cell death assays based on uptake of DNA staining dye (LDS751) using Cell cycle and Viacount assays from Guava Technologies were performed as reported (Mavrakis, et al., 2008). The retroviral vectors are based on murine stem cell virus (MSCV) and include the miRNA expression vectors encoding miRs 17, 18a, 19b-1 (miR-19), 106a, 106b, 25 (He, et al., 2005), the vectors encoding Notch-ICN (a gift from W. Pear) (Pear, et al., 1996) and Bcl2 (Wendel, et al., 2004), the individual shRNA vectors (FIG. 17) and the library vector (MRP) (FIGS. 18a and b). miRNA inhibitor oligonucleotides (antagomirs) MZIP19a-PA-1, MZIP19b-PA-1, and scrambled control (MZIP000-PA-1) were from System Biosciences.

Generation of Mice

The mouse models of Notch1-induced T-ALL and the EμMyc lymphoma based on adoptive transfer of retrovirally transduced HPCs have been reported (Pear, et al., 1996), (Wendel, et al., 2004). Data were analyzed in Kaplan-Meier format using the log-rank (Mantel-Cox) test for statistical significance. The p53 loss of heterozygosity polymerase chain reaction (LOH PCR) and immunophenotyping by surface marker analysis were as described (Wendel, et al., 2004).

Western Blot Analysis

Immunoblots were performed from whole cell lysates as described (Wendel, et al., 2004). Briefly, 50 μg of protein/sample were resolved on SDS-PAGE gels and transferred to Immobilon-P-membranes (Millipore). Antibodies were against Prkaa1 (2532, 1:1000, Cell Signaling), Bim/Bcl2L11 (AAP-330, 1:1000, Assay Designs), FoxO1 (94545, 1:1000, Cell Signaling), FoxO3a (9467, 1:1000, Cell Signaling) Phospho-FoxO3a (94665, 1:1000, Cell Signaling), Ppp2r5e (NB 100-845, NOVUS), Pten (9559, 1:1000, Cell Signaling), tubulin (1:5000; Sigma, B-5-1-2), actin (1:5000; Sigma, AC-15), Bnip3 (3769, 1:1000, Cell Signaling), phosphorylated S6 (2215, 1:1000, Cell Signaling), phosphorylated Akt (4058, 1:1000, Cell Signaling) and Dock5 [a generous gift from Alan Hall (MSKCC)]. Enhanced chemiluminescence was used for detection (ECL, Amersham).

Real-Time Quantitative PCR

Total RNA and miRNA-enriched RNA were extracted from cells and tumor samples using Allprep DNA/RNA/Protein Kits (Qiagen) and miRNeasy Mini Kits (Qiagen), respectively. Pathological diagnosis was by expert hematopathologists at Weill Cornell Medical College. cDNA synthesis and qRT-PCR and analysis by the ΔΔ Ct method were as described (Mavrakis, et al., 2008). TaqMan Gene Expression Assays were used for Bcl2L11 (Mm00437796_m1), Dock5 (Mm00555757_m1), FoxO1 (Mm00490672_m1), FoxO3 (Mm01185722_m1), Ppp2r5e (Mm00803759_m1), Prkaa1 (Mm01296695_m1) and Pten (Mm01212532_m1).

Mouse GAPD (GAPDH) (4352932) and miR-19b (000396) were from Applied Biosystems. Expression was normalized to RNU6B (001093, Applied Biosystems).

Luciferase Assays

The Dock5, Ppp2r5e, Prkaa1, and Bim 3'-UTR fragments were generated by PCR and cloned into the psi-CHECK-2 vector (Promega). The assays were performed as described (Xiao, et al., 2008). Binding site mutants were generated by site-directed mutagenesis.

Karyotype and Fluorescence In Situ Hybridization (FISH) Analysis

Metaphase chromosome preparations made from primary patient lymphoblasts were subjected to karyotype analysis following standard procedures. Genomic clones RP11-97P7 and RP11-980D6 located at 13q32 were from Invitrogen. DNA was labeled by nick translation using spectrum orange dUTP fluorochrome (Vysis, Downers Grove, Ill.). A spectrum green-labeled RB1 probe was used as control for chromosome 13q hybridization. FISH was performed by standard methods on cells used for cytogenetic analysis. Hybridization signals were scored on at least 20 metaphase spreads on DAPI stained slides using the Cytovision Imaging system attached to a Nikon Eclipse 600 microscope (Applied Imaging, Santa Clara, Calif.).

5' RACE Amplification of Aberrant Notch1 Transcripts mRNA was extracted from primary patient lymphoblasts using the Nucleotrap mRNA extraction kit from Clontech, and 5'RACE was performed with the SMART RACE kit (Clontech) using an oligonucleotide primer complementary to the sequence of exon 29 of the Notch1 gene (5'-TCGTC-CATGAGGGCACCGTCTGAAG-3').

Pooled shRNA Library Screen

The technology underlying this pooled shRNA screen and also the use of half-hairpin array detection has been described (Mavrakis, et al., 2008), (Silva, et al., 2008), (Chang, Elledge, & Hannon, 2006). Briefly, the shRNA library was cloned into the MRP vector and protein knockdown confirmed for a p53 shRNA. FL5-12 cells were transduced at low multiplicity of infection with library pools containing 1,000 shRNAs, split into triplicates and each subjected to two cycles of IL3 depletion and rescue. Samples were collected after viability had recovered for DNA isolation, PCR amplification of integrated shRNAs or the library as a reference, labeled and hybridized. Data generated (Nimblescan software) from image scans (Axon 4000BScanner) were imported into R version 2.4 for processing and analysis. Each Nimblegen 12-plex custom array consists of 12,033 half-hairpin probes. Most were represented by shRNAs in the library, and the remainder used for background estimation. As expected, these negative control spots showed lower intensities than the experimental probes on each array. Signal values less than the background were replaced with the background estimate to dampen large ratios due to low signal. The two channels for each array were then normalized using LOESS normalization; log ratios of the normalized intensity were utilized in further analyses.

Data Analysis for Pooled shRNA Screens

The analyses were performed using the Bioconductor linear models for microarray (LIMMA) (Yang, Paquet, & Dudoit, 2006), Significance Analysis of Microarrays (SAM) (Tusher, Tibshirani, & Chu, 2001) and Gene Set Analysis (GSA) (Efron & Tibshirani, 2007) libraries in R. Correlations between biological replicates were calculated for each time point, principal component analyses (PCA) to determine the magnitude of experimental effects and biological replicates. Biological replicates did not constitute a major source of variation in the experiment. The mean correlation for biological replicates was 0.60 (±0.17) and likely reflected random variations as populations drifted in culture. Biologically significant signals were identified using the SAM software to select probes reflecting differences in relative abundance of shRNAs. The unpaired, two class algorithm, which assumes independent samples of each feature across the conditions, was used. Q values are calculated empirically and used for identifying significant features. Overall, a gene was scored as being a potential candidate if its shRNA probe was found to fulfill these criteria: ≥1.65 fold change (FC), p<0.05, and current gene bank annotation with a corresponding protein. Further testing was performed using GSA to identify candidates based on data from multiple hairpins targeting the same gene, as each gene is targeted by two to four hairpins, their fold changes are summed. This statistic was compared to the same statistic from exhaustive permutation to arrive at empirical p-values for each gene. All gene sets showing positive fold-change in the GSA analysis were included in validations (except olfactory receptor481). These cut-offs are relatively arbitrary and were chosen as a conservative criterion to minimize false positives.

Computational Analysis of shRNA Off-Target Effects

Several computational analyses were performed to investigate whether the results of the screen might be attributable to off-target effects. Two hypotheses were considered: (1) that shRNAs overrepresented in the screen have sequence similarity to miR-19 itself and hence mimic miR-19 activity via sites in 3' UTRs; (2) that results of the screen are explainable by microRNA-like off-target effects on a few key genes.

For the first hypothesis, all shRNAs were ranked by ungapped sequence similarity of (a) the shRNA "seed" (positions 2-8) to the miR-19 seed region and (b) the shRNA to the full-length miR-19a and miR-19b sequences. No shRNAs in the library had the same 7-mer seed region as miR-19; among the shRNAs whose seed region matched the miR-19 7-mer seed at 6 positions (12 shRNAs with 6-mer seeds matching positions 3-8, 2 shRNAs with 6-mer seeds matching positions 2-7), none were in the top 100 shRNAs overrepresented in the screen. The maximal sequence similarity between shRNAs in the library and the full-length miR-19a/b sequences was a 13-base ungapped match; 25 shRNAs had this degree of similarity to miR-19a and/or miR-19b, but none of them occurred in the top 100 overrepresented shRNAs from the screen. Moreover, Spearman rank correlation (|rho|<0.01) between the ranking of shRNAs by overrepresentation in the screen and these similarity comparisons to miR-19 was poor.

Next, whether shRNAs that were highly ranked in the screen were more likely to have predicted off-target effects on PTEN, PRKAA1, BCL2L11, PPP2R5E, DOCK5, FOXO1, FOXO3 and BNIP3, compared to the full library was considered. If this were true, overrepresentation of an shRNA in the screen might be explainable through off-target silencing of these key genes. To predict potential microRNA-like off-target effects of shRNAs, 3' UTRs in the entire mouse genome were scanned for matches to 7-mer seed sequences (positions 2-8, no conservation filter) of shRNAs in the library. A gene with a 7-mer seed match for a given shRNA was considered to be a predicted off-target for this shRNA. We then tested if, for any of the 8 genes, the set of shRNAs that were predicted to "off-target" the gene were enriched in the top K overrepresented shRNAs from the screen, as compared to the full shRNA library. Values of K ranging from 2 to 250 were used, and no statistical significance by a Fisher's exact test for any value of K (p>0.05 in all cases for each gene) was found. These controls indicate that the shRNAs are not similar to miR-19 itself, and that the screen result could be explained by off-target effects of top ranked shRNAs on key genes.

The enrichment statistic with respect to the number of unique targets of the ~12000 shRNAs in the library and the subset of these targets that were also predicted miR-19 targets were computed using Fisher's exact test to account for the small number of 'hits'. This analysis was done for both the human and the murine genome. Target predictions were as per Targetscan 5.1.

Expression Array Analysis

Total RNA was isolated as above and analyzed for quality using the RNA 6000 NanoAssay and a Bioanalyzer 2100 (Agilent). 2 mg of total RNA was used for cDNA synthesis. Synthesis, linear amplification, and labeling of cRNA were accomplished by in-vitro transcription using the MessageAmp aRNA Kit (Ambion) and biotinylated nucleotides (Enzo Diagnostics). Ten micrograms of labeled and fragmented cRNA were then hybridized to the GeneChip according to the manufacturer (Affymetrix). Chips were scanned within the GS3000 scanner (Affymetrix), quantified using GCOS 1.4 (GeneChip Operating Software, Affymetrix), and analyzed using Partek software (Partek® Genomic Suite™ 6.4). The 'affy' and 'gcrma' libraries in the 'R' software package were used to perform robust multi-array analysis (RMA) normalization of microarray probe-level data. In addition, the 'mas5' function was used to identify present/absent calls for probes. Probes were removed from further analysis if more than one probe was absent in the technical replicates. To identify accurate target genes of probe, a BLAST search was performed using the 'blastn' program on the "Affymetrix Mouse430A_2 Target Sequences" against mouse transcripts from RefSeq Release 35. The parameters: −v1 −b1 −e 0.05 −S1 were used in the BLAST search. To calculate log expression ratio of genes, a median polish over probe-level data was performed to obtain gene expression values (i.e. the median of probe intensities across replicates was computed and the median of these probe values over probes targeting the same gene was used) and the log difference of experiment vs. control was calculated. For statistical analysis, the data were centered using the mean log 2 (expression change) of genes and normalized to have unit variance in log 2 (expression change) across all genes. This normalization results in a modified Z-transformation of the data (Z score).

Kolmogorov-Smirnov (KS) Statistic

To compare the expression changes for miR-19 targets versus all genes, their distributions of log (expression change) values were compared using a one-sided KS statistic, which assesses whether the distribution of expression changes for one set is significantly shifted downwards (down-regulated) compared to the distribution for the other set. The KS statistic computes the maximum difference in value of the empirical cumulative distribution functions (cdfs):

$$\sup_x(F_1(x) - F_2(x)),$$

where $$F_j(x) = \frac{1}{n} \sum_{i=1}^{n_j} I_{X_i \leq x}$$

is the empirical cdf for gene set j=1, 2, based on nj (Z-transformed) log(expression change) values. The Matlab function kstest2 was used to calculate the KS test statistic and asymptotic p-value.

REFERENCES

Bartel, D. P. (2004). MicroRNAs: Genomics, Biogenesis, Mechanism, and Function. Cell, 116, 281-297.

Bouillet, P., Metcalf, D., Huang, D. C., Tarlinton, D. M., Kay, T. W., Köntgen F, F., et al. (1999). Proapoptotic Bcl-2 Relative Bim Required for Certain Apoptotic Responses, Leukocyte Homeostasis, and to Preclude Autoimmunity. Science, 286 (5445), 1735-1738.

Chang, K., Elledge, S. J., & Hannon, G. J. (2006). Lessons from Nature: MicroRNA-based shRNA Libraries. Nature Methods, 3 (9), 707-714.

Efron, B., & Tibshirani, R. (2007). On Testing the Significance of Sets of Genes. Journal of Applied Statistics, 1 (1), 107-129.

Ellisen, L. W., Bird, J., West, D. C., Soreng, A. L., Reynolds, T. C., Smith, S. D., et al. (1991). TAN-1, the Human Homolog of the *Drosophila* Notch Gene, Is Broken by Chromosomal Translocations in T Lymphoblastic Neoplasms. Cell, 66 (4), 649-661.

He, L., Thomson, J. M., Hemann, M. T., Hernando-Monge, E., Mu, D., Goodson, S., et al. (2005). A MicroRNA Polycistron As a Potential Human Oncogene. Nature, 435 (7043), 828-833.

Mavrakis, K. J., Zhu, H., Silva, R. L., Mills, J. R., Teruya-Feldstein, J., Lowe, S. W., et al. (2008). Tumorigenic Activity and Therapeutic Inhibition of Rheb GTPase. Genes & Development, 22 (16), 2178-2188.

Paddison, P. J., Silva, J. M., Conklin, D. S., Schlabach, M., Aruleba, S., Balija, V., et al. (2004). A Resource for Large-scale RNA-interference-based Screens in Mammals. Nature, 428 (6981), 427-431.

Palermo, T., McKenna, K., O'Neil, J., Galinksky, I., Stone, R., Suzukawa, K., et al. (2006). Activating Mutations in NOTCH1 in Acute Myeloid Leukemia and Lineage Switch Leukemias. Leukemia, 20 (11), 1963-1966.

Pear, W. S., Aster, J. C., Scott, M. L., Hasserjian, R. P., Soffer, B., Sklar, J., et al. (1996). Exclusive Development of T Cell Neoplasms in Mice Transplanted with Bone Marrow Expressing Activated Notch Alleles. The Journal of Experimental Medicine, 183 (5), 2283-2291.

Petrocca, F., Visone, R., Onelli, M. R., Shah, M. H., de Martino, I., Iliopoulos, D., et al. (2008). E2F1-regulated microRNAs Impair TGFb-Dependent Cell-cycle Arrest and Apoptosis in Gastric Cancer. Cancer Cell, 13, 272-286.

Plas, D. R., Talapatra, S., Edinger, A. L., Rathmell, J. C., & Thompson, C. B. (2001). Akt and Bcl-xL Promote Growth Factor-independent Survival Through Distinct Effects on Mitochondrial Physiology. The Journal of Biological Chemistry, 276 (15), 12041-12048.

Silva, J. M., Marran, K., Parker, J. S., Silva, J., Golding, M., Schlabach, M. R., et al. (2008). Profiling Essential Genes in Human Mammary Cells by Multiplex RNAi Screening. Science, 319 (5863), 617-620.

Tusher, V. G., Tibshirani, R., & Chu, G. (2001). Significance Analysis of Microarrays Applied to the Ionizing Radiation Response. Proceedings of the National Academy of Sciences, 98 (9), 5116-5121.

Volinia, S., Calin, G. A., Liu, C. G., Ambs, S., Cimmino, A., Petrocca, F., et al. (2006). A microRNA Expression Signature of Human Solid Tumors Defines Cancer GeneTargets. Proceedings of the National Academy of Sciences, 103, 2257-2261.

Wendel, H. G., De Stanchina, E., Fridman, J. S., Malina, A., Ray, S., Kogan, S., et al. (2004). Survival Signalling by Akt and eIF4E in Oncogenesis and Cancer Therapy. Nature, 428 (6980), 332-337.

Weng, A. P., Ferrando, A. A., Lee, W., Morris, I. J., Silverman, L. P., Sanchez-Irizarry, C., et al. (2004). Activating Mutations of NOTCH1 in Human T Cell Acute Lymphoblastic Leukemia. Science, 306 (5694), 269-271.

Xiao, C., Srinivasan, L., Calado, D. P., Patterson, H. C., Zhang, B. W., Henderson, J. M., et al. (2008). Lymphoproliferative Disease and Autoimmunity in Mice with Increased miR-17~92 Expression in Lymphocytes. Nature Immunology, 9 (4), 405-414.

Yang, Y. H., Paquet, A., & Dudoit, S. (2006). R package version 1.12.0.

Example 2 microRNAs (miRNAs) are ubiquitous regulators of biological processes involved in normal development, in differentiation and in diseases, including cancer. They act by regulating gene expression at the transcriptional and translational levels (Bartel, 2004). The regulation of gene expression by miRNAs is complex. Many mRNAs contain, within their 3'UTRs, binding sites for multiple miRNAs, and most miRNAs can potentially target a large number of genes (Bartel, 2004). It is clear that not every miRNA binding site predicted by sequence analysis contributes to a phenotype. Conversely, multiple miRNAs can affect a single cellular pathway (Mavrakis, et al., 2010), (Li, et al., 2007).

T-ALL arises as a consequence of several cooperating genetic lesions (Aifantis, Raetz, & Bu, 2008). For example, most cases harbor activating lesions of NOTCH1 (Weng, et al., 2004), and tumor suppressor genes, including PTEN (Palomero, et al., 2007); NF1 (Balgobind, et al., 2008); PHF6 (Van Vlierberghe, et al., 2010); PTPN2 (Kleppe, et al., 2010); IKZF1 (Dail, et al., 2010), (Winandy, Wu, & Georgopoulos, 1995), (Marçais, et al., 2010), (Sun, et al., 1999), (Mullighan, et al., 2007); and FBXW7 (O'Neil, et al., 2007), (Thompson, et al., 2007), are targets of inactivating somatic mutations or deletions in T-ALL. The oncogenic miR-17~92 cluster is targeted by t(13;14)(q32;q11) translocation in T-ALL (Landais, Landry, Legault, & Rassart, 2007). Individual miRNAs have now been implicated in T-ALL, for example miR-19b as described above in Example 1 (Mavrakis et al, 2010). miR19b is a member of the oncogenic miR-17~92 cluster (see also FIG. 1a). miRNA expression analyses in various cancers have indicated that only a small number of miRNAs are highly expressed in cancer cells and that a pattern reminiscent of the tissue of origin is maintained (Lu, et al., 2005), (Landgraf, et al., 2007).

In these studies we have utilized three separate approaches to assess and determine miRNAs relevant to T-ALL, and potentially to other cancers. The three approaches—miRNA expression analysis, analysis of potential miRNA binding sites in known tumor suppressor genes, and an unbiased screen for oncogenic miRNAs—were used to identify miRNAs potentially important in T-ALL. The contribution of certain of these miRNAs to the pathogenesis of T-ALL was confirmed both by evaluating the activities of the miRNAs themselves in a mouse model of leukemogenesis and by evaluating the activity of antagomirs to the miRNAs in human T-ALL cell lines.

miRNA Expression Analysis

Quantitative PCR was used to measure the expression of 430 miRNAs in 50 clinical T-ALL specimens and 18 T-ALL cell lines. The pattern of miRNA expression was found to be quite consistent, with ten miRNAs (miR-223, miR-19b, miR-20a, miR-92, miR-142-3p, miR-150, miR-93, miR-26a, miR-16 and miR-342) highly expressed in T-ALL cells and cell lines and the remaining 420 miRNAs detected at significant lower levels. Comparison of the miRNA expression pattern in T-ALL cells and cell lines to that in purified progenitor (CD34$^+$ and CD3$^-$CD4$^+$CD8$^+$) cells and normal (CD3$^+$CD4$^+$CD8$^+$, CD3$^+$CD4$^+$CD8$^-$ and CD3$^+$CD4$^-$CD8$^+$) T-cells demonstrated T-ALL-specific increases in the expression of miR-223 and, to a lesser extent, in the expression of miR-376 and miR-662.

Analysis of Potential miRNA Binding Sites in Tumor Suppressor Genes Implicated in T-ALL Analysis of the 3'UTRs of twelve tumor suppressor genes implicated in the pathogenesis of T-ALL for potential miRNA binding sites generated a hierarchy of miRNAs potentially implicated in T-ALL. Five of the ten miRNAs most highly expressed in T-ALL, specifically miR-25/92, miR-26, miR-19, miR-223 and miR-20/93/106, were also among the highest ranking in this analysis. (miRNAs with identical 3'UTR-binding 'seed' sequences are grouped together in this and subsequent analyses, and it should be understood that miRNAs with identical seed sequences may be interchangeable.)

Unbiased Genetic Screen for Oncogenic miRNAs

Infection of c-MYC-transduced mouse embryo fibroblasts (MEFs) with a retroviral miRNA library and selection of cells that remained adherent after reduction in serum concentration from 10% to 0.1% was used to identify those miRNAs that protect cells from apoptotic death. To ensure that the miRNAs identified in this initial screen are truly associated with leukemogenesis and not merely with growth arrest, a library of GFP-tagged miRNAs identified in the primary screen was used to infect interleukin-3 (IL-3)-dependent FL5-12 murine pro B-cells. Enrichment of GFP-expressing cells following depletion of IL-3 allowed identification of the miRNAs associated with IL-3-independent growth. The six miRNAs confirmed to confer IL-3 independence on FL5-12 cells were miR-19b, miR-20/93/106 and miR-25/92, which are among the miRNAs most highly expressed in T-ALL cells and also among the miRNAs most highly ranked as potentially interacting with tumor suppressor genes implicated in T-ALL; miR-26 and miR-223, which are among the miRNAs most highly expressed in T-ALL cells; and miR-148/152, which is among the miRNAs most highly ranked as potentially interacting with tumor suppressor genes implicated in T-ALL.

Leukemogenic Activity of miRNAs Implicated in T-ALL

The oncogenic potential of the six miRNAs identified as potentially important in T-ALL leukemogenesis was then tested, in vivo. HPCs were transduced with NOTCH1 plus an miRNA or an empty vector control; the HPCs were transplanted into irradiated, syngenic recipients; and regular blood counts were performed to detect the onset of T-ALL. In this assay, in which retrovirally delivered miRNAs were expressed at levels 2- to 6-fold higher than in leukemic controls, miR-19b, miR-20a, miR-26, miR-92, miR-148 and miR-223 each significantly accelerated the onset of CD4$^+$ CD8$^+$ T-ALL (while miR-23, miR-24 and miR-30 did not).

Anti-Leukemogenic Activity of Antagomirs to the miRNAs Implicated in T-ALL

Finally, the effect of miRNA antagomirs on the growth rate and viability of human T-ALL cell lines, including T-ALL1, KOPTK1 and JURKAT, was assessed. Antagomirs against miR-19b, miR-26 and miR-92 reduced growth rate, significantly reduced cell viability and de-repressed the tumor suppressor genes PTEN and BCL2L11 (Bim) (while antagomirs against miR-148 and the randomly chosen miR-182 did not). An antagomir directed against miR-223 similarly reduced growth rate and cell viability. Compared to expression of the individual antagomirs, co-expression, in T-ALL cell lines, of antagomirs to miR-19b and miR-92 or to miR-19b, miR-92 and miR-26a caused a more pronounced decrease in growth rate, more than doubled the proportion of apoptotic cells, produced larger increases in the expression of PTEN and BCL2L11 and had additive effects on the 3' UTR reporter activity of PTEN and BCL2L11.

These data demonstrate that miR-19b, miR-20a, miR-26, miR-92, miR-148 and miR-223 account for the majority of miRNA expression in human T-ALL, downregulate the activity of a common set of tumor suppressor genes, including PTEN, BCL2L11, NF1, FBXW7, IKZF1 and PHF6, implicated in the pathogenesis of T-ALL via overlapping and cooperative effects on their expression and are capable of promoting T-ALL in animal models.

miR-223, which was thought to be a myeloid-specific miRNA (Fazi, et al., 2005), (Chen, Li, Lodish, & Bartel, 2004), (Johnnidis, et al., 2008) is selectively up-regulated in human T-ALL. miR-223 is a strong regulator of FBXW7 (CDC4), which acts as an E3 ubiquitin ligase for NOTCH1 and c-MYC and is mutated in ~20% of T-ALL cases as well as in other cancers (O'Neil, et al., 2007), (Thompson, et al., 2007), (Maser, et al., 2007). Other miRNAs are also found in normal progenitors and/or in differentiated T-cells and likely realize their oncogenic potential only in the context of additional mutations.

miR-148 has been implicated in gastrointestinal cancers, particularly gastric and colorectal cancer (Chen Y et al (2010) J Gastrointest Surgery 14(7):doi:10.1007/s11605-010-1202-2). In additional cell line expression studies using RT-PCR analysis of miR-148 we have observed increased expression of miR148 in several liver cell lines (HLF, HLE and HepG2 cells) (data not shown), implicating an additional role for miR-148 in liver cancer.

The present data indicate that measuring the expression of miR-19b, miR-20a, miR-26, miR-92, miR-148 and/or miR-223 can be used for the diagnosis of hematologic malignancies, including T-ALL, for predicting response to specific therapeutic regimens and/or for monitoring response to therapy. They further provide evidence that antagonists/antagomirs of miR-19b, miR-20a, miR-26, miR-92, miR-148 and/or miR-223, and particularly of miR-19b, miR-26a, miR-92 and/or miR-223, alone or particularly in combination, are candidate therapeutics against cancers, including hematologic malignancies, and any cancer(s) or condition(s) overexpressing miR-19b, miR-20a, miR-26, miR-92, miR-148 and/or miR-223.

Results

Identification of miRNAs Highly Expressed in T-ALL Cells and Cell Lines

Figure 19:
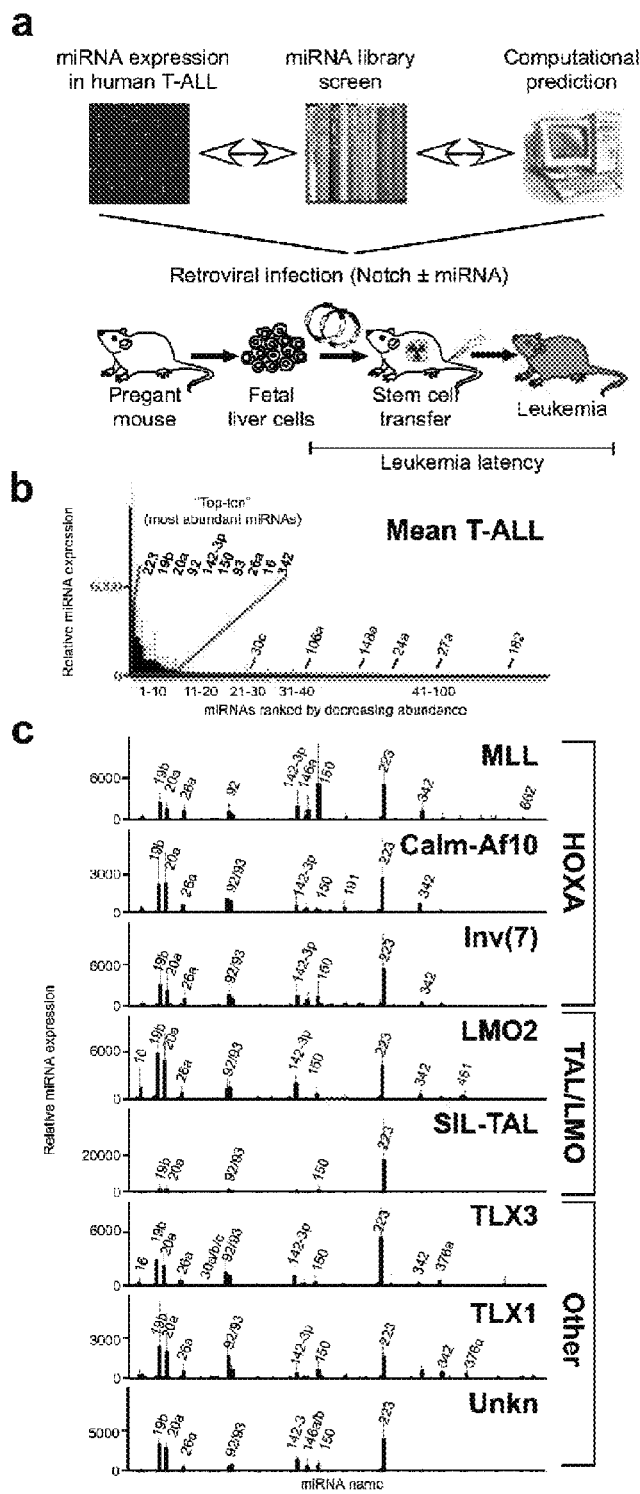
FIG. 19. Comprehensive study of oncogenic miRNAs in T-ALL. a. Schematic of the experimental strategy. b. Average miRNA expression across 50 T-ALL samples by quantitative RT-PCR normalized to the mean expression value of all expressed miRNAs in a given sample (mean and standard deviation (SD)) and ordered by expression levels with the 'top-ten' most abundantly expressed miRNAs indicated. c. miRNA expression in different cytogenetic subgroups of T-ALL (mean and SD) ordered numerically with the most abundant miRNAs indicated.
Figure 20:
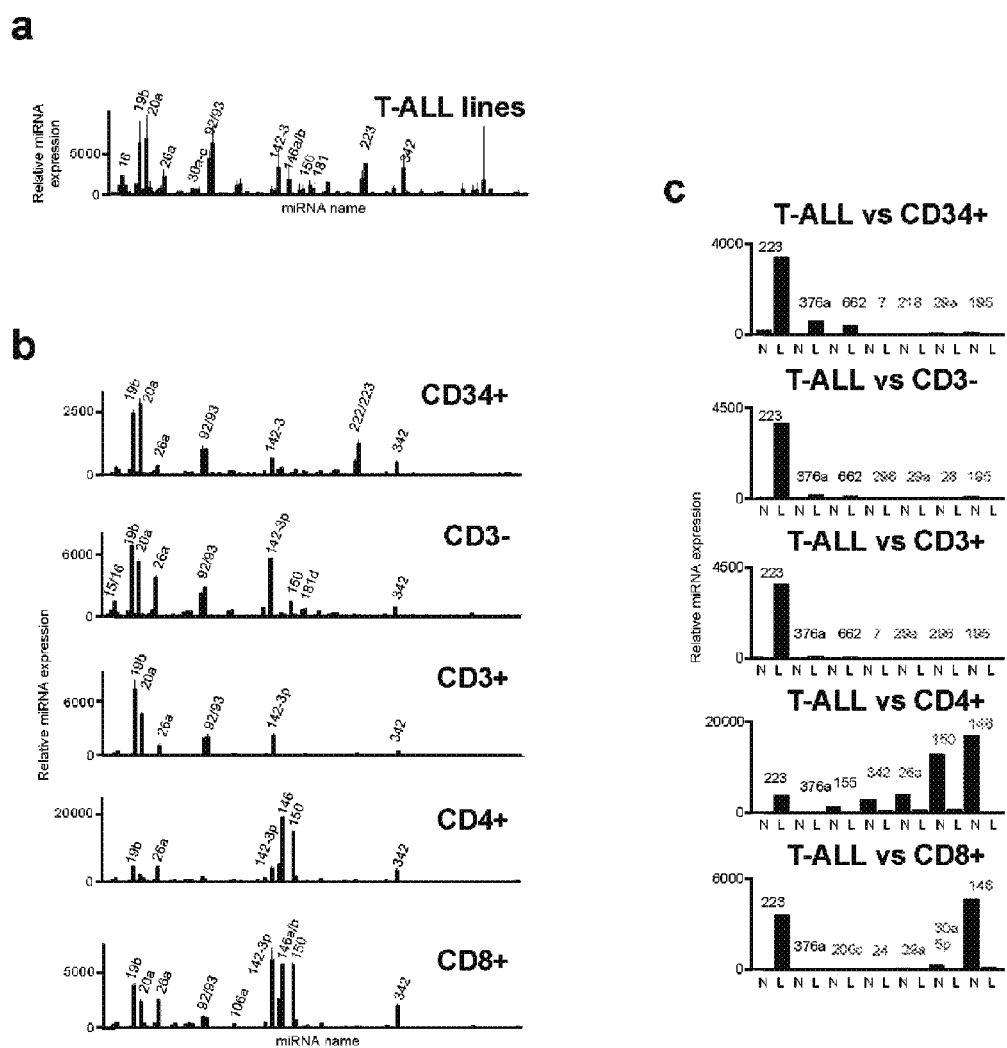
FIG. 20. mRNA expression analyses. a. Quantitative RT-PCR measurement of miRNA expression in 18 human T-ALL cell lines (mean and SD). b. Quantitative RT-PCR measurement of miRNA expression in FACS-sorted normal cell populations (mean and SD of two replicates per sample). c. Differential miRNA expression comparing the average value across all human T-ALL samples (L) to the indicated normal cell populations (N). Only miRNAs with a fold change difference>5 and detectable expression (relative value>50) in either normal or leukemic sample are shown; black numbers indicate higher expression in leukemic cells, red numbers indicate higher expression in normal cells.

An unbiased miRNA library screen was used to determine miRNA expression patterns in human T-ALL (FIG. 19a). Quantitative PCR (Mestdagh, et al., 2009) was used to measure the expression of 430 miRNAs in 50 clinical T-ALL specimens representing distinct cytogenetic groups (Aifantis, Raetz, & Bu, 2008) (including TLX1, TLX3, HOXA and TAL1/LMO2) and in a panel of 18 human T-ALL cell lines. Ten miRNAs were highly expressed, whereas most other miRNAs were barely detectable. These 'top-ten' miRNAs were (in descending order of expression levels): miR-223, miR-19b, miR-20a, miR-92, miR-142-3p, miR-150, miR-93, miR-26a, miR-16 and miR-342 (FIG. 1b). Overall the miRNA expression pattern was quite similar between cytogenetic groups and also preserved in human T-ALL cell lines (FIG. 19c, FIG. 20a). A comparison with purified progenitor ($CD34^+$ and $CD4^+CD8^+CD3^-$) cell populations and normal ($CD4^+CD8^+CD3^+$ double positive, $CD4^+$ single positive or $CD8^+$ single positive) T-cell populations revealed leukemia-specific increases in miR-223 expression and much smaller leukemia-specific increases in the expression of miR-376 and miR-662 (FIGS. 20b and c). Hence, a small number of miRNAs are highly expressed in human T-ALL.

Analysis of Potential miRNA Binding Sites in Tumor Suppressor Genes Implicated in T-ALL Next, computational approaches were used to identify miRNAs potentially important in the pathogenesis of T-ALL. 3'UTRs of twelve tumor suppressor genes implicated in the pathogenesis of T-ALL (specifically FBXW7 (O'Neil, et al., 2007), (Thompson, et al., 2007); PTEN (Palomero, et al., 2007); PHF6 (Van Vlierberghe, et al., 2010); PTPN2 (Kleppe, et al., 2010); IKZF1 (Dail, et al., 2010), (Winandy, Wu, & Georgopoulos, 1995), (Marçais, et al., 2010), (Sun, et al., 1999), (Mullighan, et al., 2007); NF1 (Balgobind, et al., 2008); BCL2L1 (Mavrakis, et al., 2010); CDK8; cyclin C; NLK; RB1; and p53) were analyzed for potential miRNA binding sites (Lewis, Shih, Jones-Rhoades, Bartel, & Burge, 2003), (Friedman, Farh, Burge, & Bartel, 2009). As expected, many miRNAs bind these genes, so a rank order was generated by calculating a cumulative context score (Table 3) or by adding the number of conserved 7- and 8-mer sites, in both cases restricting to broadly conserved miRNA seed families. Strikingly, five of the ten most highly expressed miRNAs were also among the highest-ranking miRNAs in this analysis ($p<1e-4$ using Wilcoxon for enrichment). Thus, miR-19b, miR-20a193, miR-26a, miR-92, and miR-223 are highly expressed in T-ALL and predicted to target tumor suppressor genes in T-ALL. Hence, five of the ten most abundantly expressed miRNAs in T-ALL target tumor suppressor genes implicated in this cancer.

TABLE 3

Computational analysis and ranking of miRNA binding sites in candidate tumor suppressor genes implicated in T-ALL

| | Context Score[a] | | | | | | |
| miRNA | FBXW7 | BCL2L11 | NF1 | PTEN | IKZF1 | PHF6 | Sum[b] |
| --- | --- | --- | --- | --- | --- | --- | --- |
| miR-25/92[c] | −0.9 | −0.6 | −0.2 | −0.4 | −0.2 | 0 | −3.2 |
| miR-27 | −0.8 | −0.2 | −0.2 | 0 | −0.4 | 0 | −3.0 |
| miR-203 | 0 | −0.2 | −0.2 | 0 | −0.7 | −0.6 | −2.9 |
| miR-148/152[c] | 0 | −0.8 | 0 | −0.7 | −0.3 | 0 | −2.4 |
| miR-101 | −0.2 | −0.3 | −0.4 | 0 | −0.1 | −0.2 | −2.3 |
| miR-26 | 0 | 0 | 0 | −0.9 | 0 | −0.4 | −2.3 |
| miR-103 | −0.3 | 0 | −0.9 | −0.6 | 0 | 0 | −2.2 |
| miR-200 | −0.6 | −0.2 | −0.4 | −0.2 | 0 | −0.4 | −2.2 |
| miR-144 | 0 | −0.2 | −0.9 | −0.3 | 0 | −0.2 | −2.0 |
| miR-128 | −0.3 | 0 | −0.3 | 0 | −0.4 | −0.5 | −1.9 |
| miR-19 | 0 | −0.3 | −0.3 | −0.6 | −0.1 | 0 | −1.8 |
| miR-223 | −1.4 | 0 | 0 | −0 | 0 | 0 | −1.8 |
| miR-137 | −0.3 | −0.1 | −0.4 | 0 | −0.2 | 0 | −1.7 |

TABLE 3-continued

Computational analysis and ranking of miRNA binding sites
in candidate tumor suppressor genes implicated in T-ALL

| miRNA | Context Score[a] | | | | | | |
|---|---|---|---|---|---|---|---|
| | FBXW7 | BCL2L11 | NF1 | PTEN | IKZF1 | PHF6 | Sum[b] |
| miR-217 | 0 | −0.2 | −0.6 | −0.1 | −0.2 | −0.5 | −1.6 |
| miR-20/93/106[c] | 0 | −0.2 | 0 | −0.3 | 0 | −0.2 | −1.5 |

[a]The context score is calculated by correlating contextual features at a predicted site (local AU content, predicted binding at the 3' end of the miRNA, position in the 3'UTR) with the extent of down-regulation in miRNA transfection experiments and indicates strength of miRNA-mRNA interaction; larger negative values correspond to more effective sites; only values < −0.1 are shown; scores are rounded to the nearest 0.1.
[b]The sum is calculated for all twelve genes included in the analysis.
[c]Indicates homologous miRNAs with identical seed sequences.

Unbiased Genetic Screen for Leukemogenic miRNAS

Figure 21:
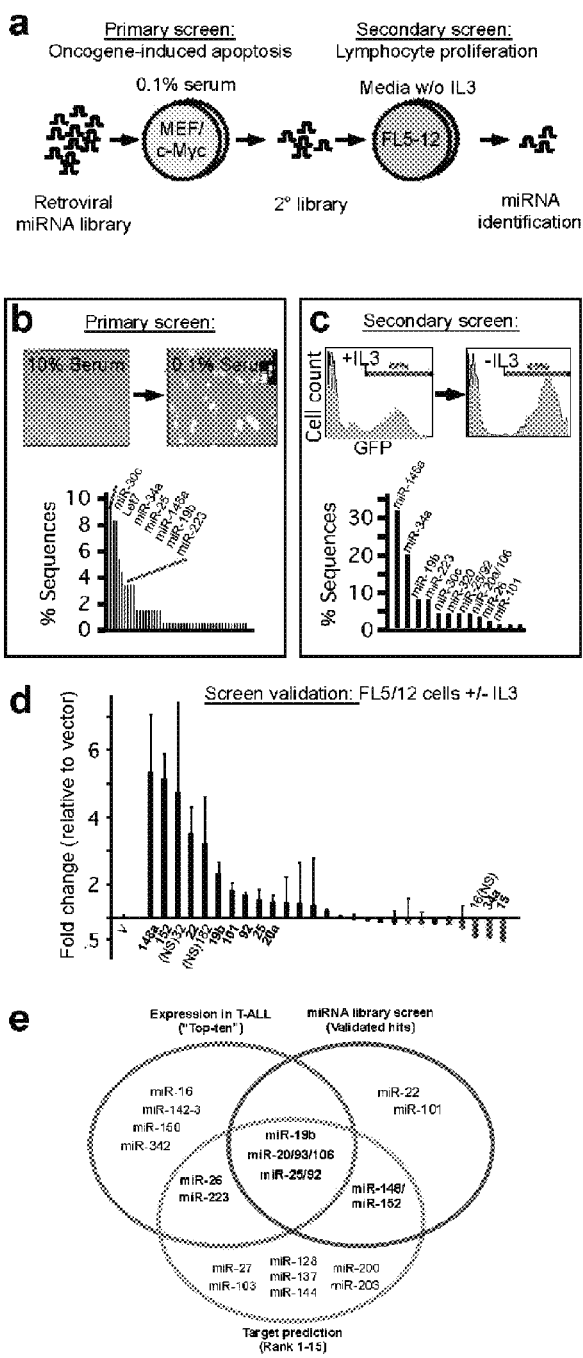
FIG. 21. Pooled library screen for oncogenic miRNAs. a. Schematic of the screening protocol: The primary screen selects for bypass of oncogene-induced apoptosis, the secondary screen for lymphocyte proliferation in the absence of IL-3. b. Primary screen: Micrograph illustrating c-MYC-induced apoptosis in MEFs (inset) and percentage of miRNA sequences retrieved from surviving/adherent cells (below). Briefly, DNA was isolated, the integrated miRNA(s) were amplified by PCR and sub-cloned, ~100 clones were picked and the integrated miRNAs were sequenced. c. Secondary screen: Enrichment of FL5-12 cells expressing the secondary miRNA library and GFP upon IL-3 depletion (inset) and percentage of miRNA sequences retrieved from FL5-12 cells after IL-3 depletion (below). d. Screen validation: The mean fold-change and SD of miRNA/GFP-expressing FL5-12 cells before and after IL-3 depletion (results of three independent experiments). e. Summary of interim results: The ten most highly expressed miRNAs in human T-ALL (red circle), the validated 'hits' in the miRNA screen (blue circle) and miRNAs that bind tumor suppressor genes implicated in T-ALL (green circle).

Finally, an unbiased miRNA library screen for leukemogenic miRNAs was conducted. A two-step, sib-selection protocol was utilized. Briefly, miRNAs were first screened for their ability to protect mouse MEF cells from apoptosis induced by c-MYC (Evan, et al., 1992), which is a key downstream effector of NOTCH1 in T-ALL (Palomero, et al., 2006), (Weng, et al., 2006), (Klinakis, Szabolcs, Politi, Kiaris, Artavanis-Tsakonas, & Efstratiadis, 2006). c-MYC-transduced MEFs were infected with a retroviral miRNA library, cells that remained adherent after reduction in serum from 10% to 0.1% were collected and the transduced miRNAs harbored by these adherent cells were identified. To ensure that the miRNAs identified in this initial screen, which included the highly expressed miR-25/92, miR-19b, and miR-223 (FIG. 21b), are truly associated with leukemogenesis and not merely with growth arrest (Seoane, Le, & Massagué, 2002), miRNAs were then screened for their ability to promote cytokine-independent growth in lymphocytes (Mavrakis, et al., 2010) (FIG. 21a). To generate a secondary library, all miRNAs from the primary screen were sub-cloned and FL5-12 lymphocytes were partially transduced with the pooled vectors expressing the individual miRNAs along with the GFP reporter. Following IL-3 depletion and enrichment of GFP expressing cells, the most abundant miRNAs were identified by sequence analysis (FIG. 21c). Retesting each of the most abundant miRNAs in the same FL5-12 lymphocyte assay confirmed that miR-148a/152, miR-22, miR-19b, miR-101, miR-25/92 and miR-20a/106 confer IL-3 independence on FL5-12 cells (FIG. 21d).

Complementary Approaches Identify Multiple Potentially Leukemogenic miRNAs in T-ALL These results are summarized in FIG. 21e. In brief, the six miRNAs confirmed to confer IL-3 independence on FL5-12 cells were miR-19b, miR-20/92/106 and miR-25/92, which are among the miRNAs most highly expressed in T-ALL cells and cell lines and also among the miRNAs most highly ranked as potentially interacting with tumor suppressor genes implicated in T-ALL; miR-26 and miR-223, which are among the miRNAs most highly expressed in T-ALL cells; and miR-148/152, which is among the miRNAs most highly ranked as potentially interacting with tumor suppressor gene implicated in T-ALL. Hence, complementary approaches define a set of potentially oncogenic miRNAs in T-ALL.

Leukemogenic Activity of miRNAs Implicated in T-ALL

Figure 22:
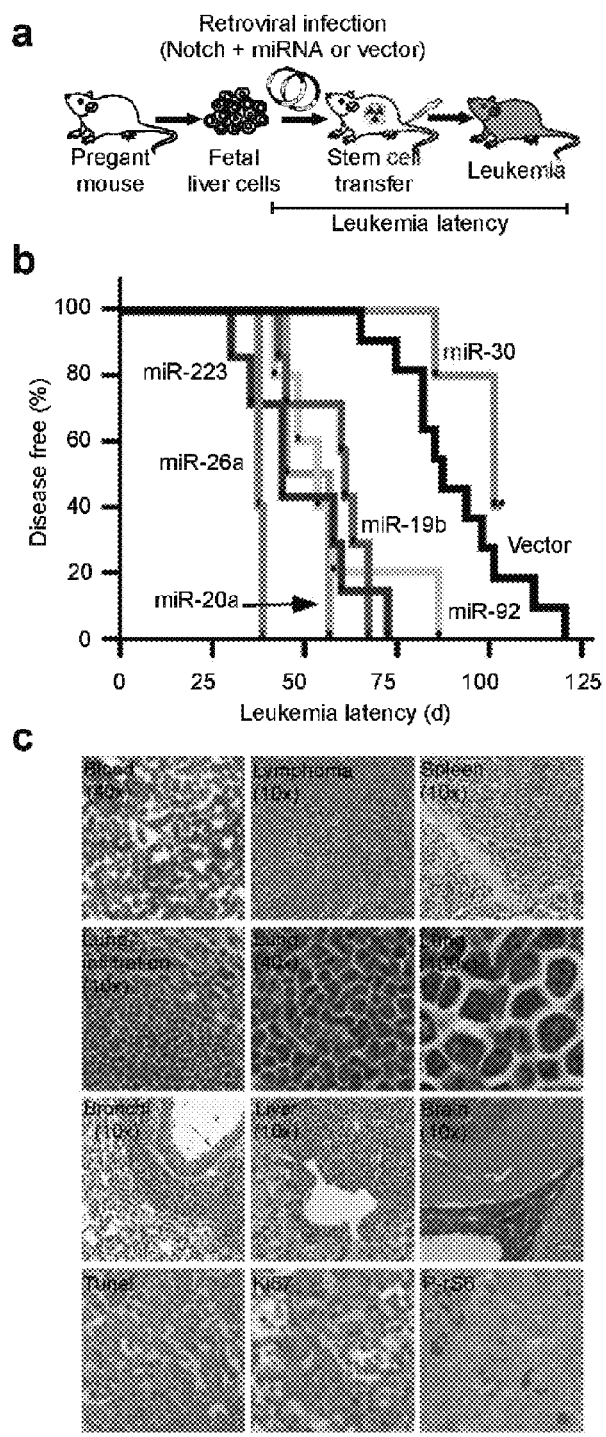
FIG. 22. Candidate miRNAs act as oncogenes in a murine T-ALL model. a. Schematic of adoptive transfer model of NOTCH1-driven T-ALL. b. Kaplan-Meier analysis of leukemia-free survival after transplantation of HPCs expressing NOTCH1-ICN and either vector (black, n=13), miR-19b (red, n=7), miR-20a (orange, n=4), miR-26a (magenta, n=5), miR-30 (grey, n=5), miR-92 (green, n=5) or miR-223 (blue, n=7). c. Representative microphotographs of NOTCH1-induced T-ALL. The pathologic appearance of leukemias expressing different miRNAs is identical (not shown).

A murine model of NOTCH1-induced T-ALL was used to directly test the oncogenic potential of the most promising miRNAs in vivo. Briefly, HPCs were transduced with NOTCH1 together with either empty vector or an miRNA and transplanted into irradiated, syngeneic recipients. Animals were monitored for leukemia onset by regular blood counts (FIG. 22a). First, disease acceleration by miR-19b (n=7, p<0.01) compared to empty vector (n=13) was confirmed (Mavrakis, et al., 2010). Similar disease acceleration was found with miR-20a (n=4, p<0.001), miR-26a (n=5, p<0.001), miR-92 (n=5, p=0.02), and miR-223 (n=7, p<0.01). Typically, animals receiving HPCs transduced with these miRNAs develop an acute leukemia by 75 days, while >80% of vector controls or animals receiving miR-30 (n=5, p=0.15) remain disease free at this time (FIG. 22b). Based on the in vitro screen and prediction, additional miRNAs were tested. Specifically, miR-148 was associated with significant disease acceleration (n=7, p<0.01), and miR-27 exhibited a strong trend in disease acceleration (n=5, p=0.05), while neither miR-23 (n=5, p>0.05) nor miR-24 (n=5, p>0.05) showed any effect (FIG. 23a). Pathological analysis revealed that all leukemias were CD4$^+$CD8$^+$ double positive T-ALLs (FIG. 21b), were highly proliferative by Ki67, were devoid of apoptosis by TUNEL, and widely infiltrated the lungs, livers and brains of leukemic animals (FIG. 22c). Quantitative PCR demonstrated 2- and 6-fold increased expression of miRNAs in leukemic cells driven by retrovirally delivered miRNAs compared to leukemic cells from controls (FIG. 23c). Thus, miR-19b, miR-20a, miR-26a, miR-223 and also the less abundant miR-27a and miR-148/152 behave as oncogenes in a murine T-ALL model.

Genes Targeted by miRNAs Implicated in T-ALL

The miRNAs that accelerate the onset of NOTCH1-induced T-ALL appear to be significantly enriched among the miRNAs that ranked highest in the computational analysis of miRNA target genes, (empirical p-value p<1e-4 for number of seeds or context scores) (Table 3). This observation was tested using an unbiased machine learning approach. Briefly, lasso regression was used to identify target genes that discriminate between leukemogenic miRNAs and groups of randomly selected miRNAs that did not accelerate the onset of NOTCH1-induced T-ALL. Since only a small number of positive training examples (leukemogenic miRNAs) were available, stability analysis was performed by repeating the learning procedure 50 times with different negative training sets. FBXW7 (identified in 46/50 runs), BCL2L11 (21/50 runs), and PTEN (11/50 runs) were among the 15 genes most frequently identified in this analysis.

Figure 24:
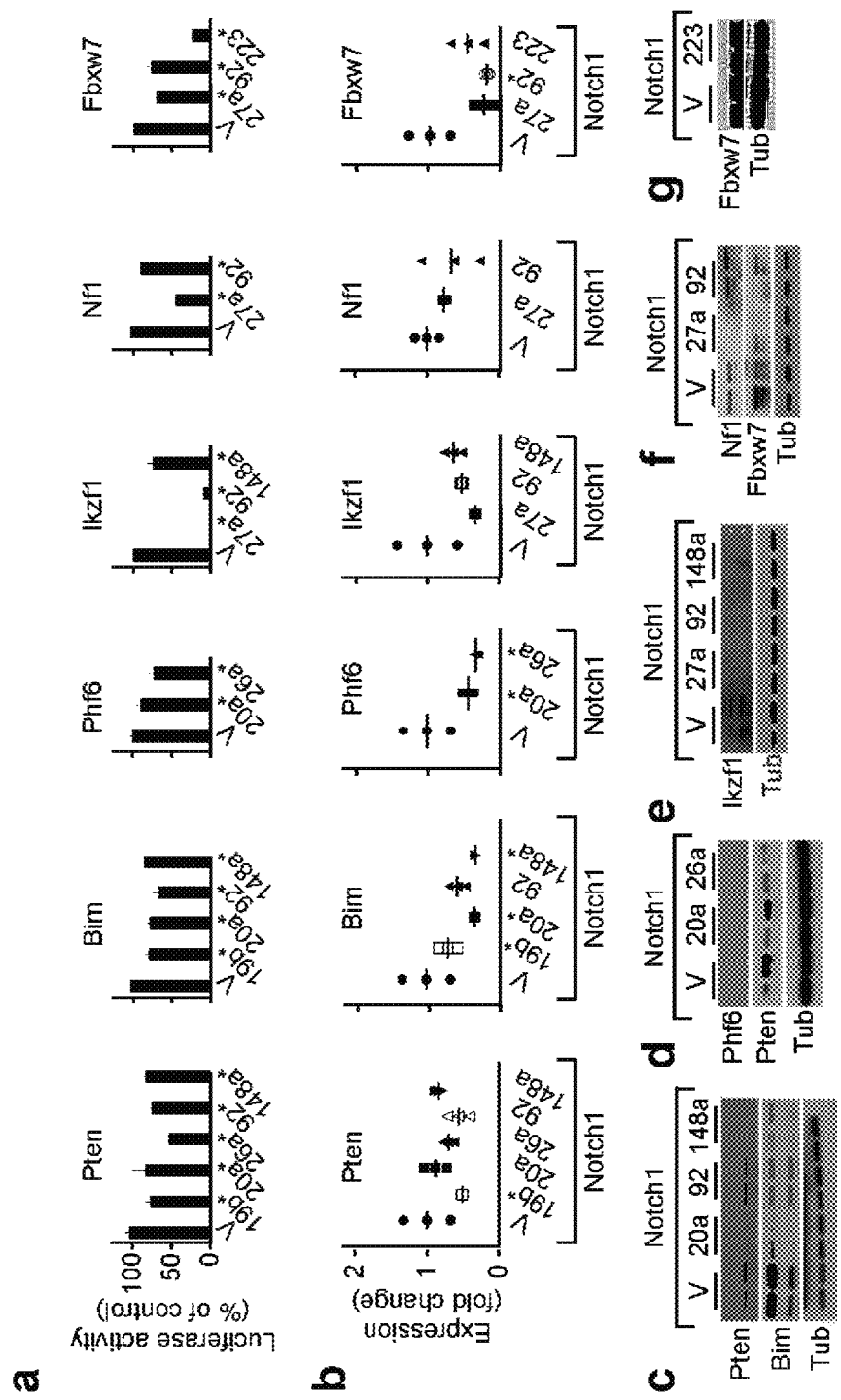
FIG. 24. miRNAs regulate the expression of tumor suppressor genes in murine T-ALL. a. Luciferase reporter assays testing the effect of miRNAs on 3'UTRs of the indicated genes, (mean and SD of triplicate experiments). V=vector, numbers indicate the miRNA name, * indicates significant (p<0.05) effects compared to vector. b. Quantitative RT-PCR measurement of gene expression in murine T-ALLs expressing NOTCH1 and the indicated miRNA. Range and mean shown as fold change vs. T-ALLs expressing the control vector, * indicates significance (p<0.05). c-g. Immunoblots of lysates from murine T-ALLs expressing NOTCH1 and vector or the indicated miRNAs and probed with indicated antibodies.
Figure 25:
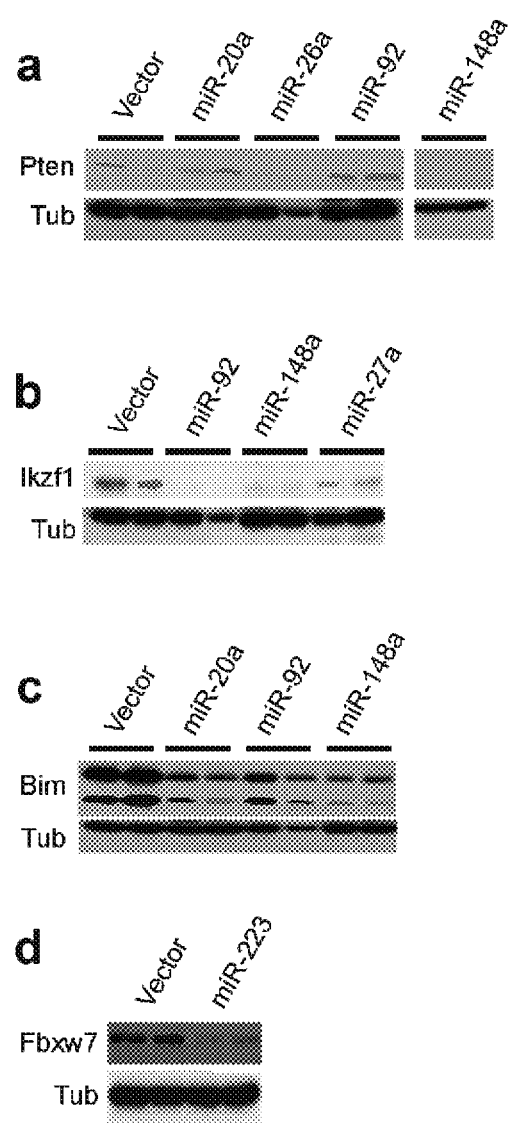
FIG. 25. miRNAs affect the expression of several tumor suppressor genes in murine FL5-12 cells. a-d. Lysates of GFP-sorted FL5-12 cells expressing either empty vector or the indicated miRNA were probed for the indicated proteins.

These target gene predictions were tested experimentally, both by using 3'UTR reporter assays (FIG. 24a) and by quantitative PCR (FIG. 24b) and immunoblot (FIG. 24c-g) assays of murine leukemias. miR-19b regulates PTEN and BCL2L11 expression (Mavrakis, et al., 2010). miR-20a has similar effects on BCL2L11, and both miR-20a and miR-26a reduce levels of PTEN and PHF6 protein and mRNA in leukemic cells. miR-27a and miR-148a regulate IKZF1, NF1 and FBXW7. Similarly, miR-92 affects IKZF1 and FBWX7 but does not target the murine NF1. As predicted, miR-223 strongly regulates FBXW7 reporter activity and protein levels. Findings in miRNA-transduced FL5-12 cells largely confirmed these results (FIG. 25). Hence, leukemogenic miRNAs produce partially overlapping effects on six tumor suppressor genes in T-ALL.

Figure 26:
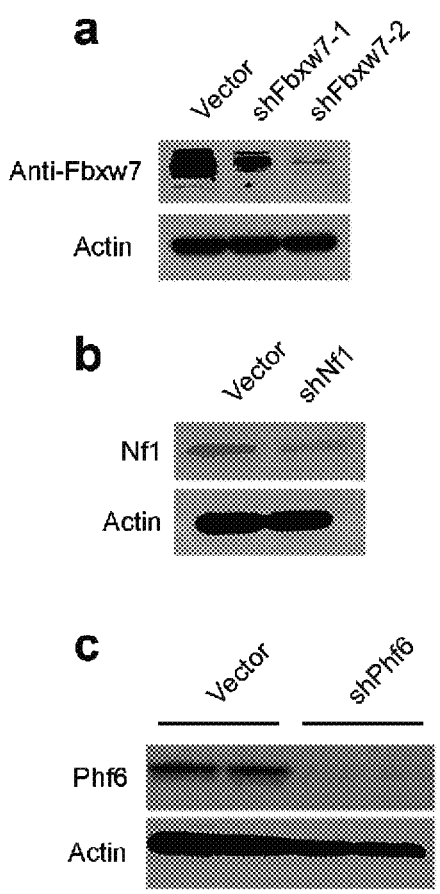
FIG. 26. Protein knockdown by shRNAs. a-c. Lysates of GFP-sorted FL5-12 cells expressing either empty vector or the indicated shRNAs were probed for the indicated proteins.
Figure 27:
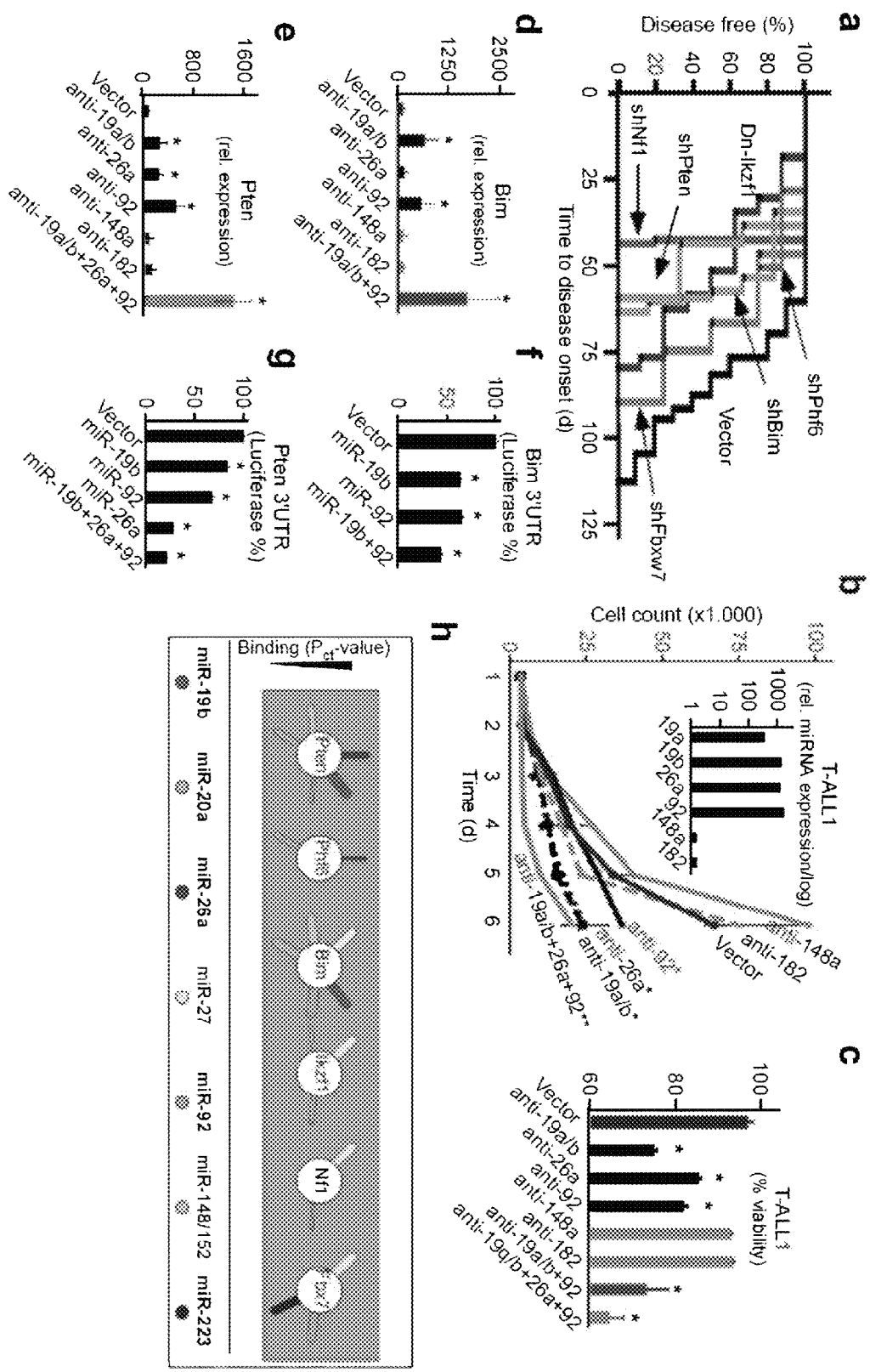
FIG. 27. Individual and cooperative miRNA on T-ALL suppressor genes. a. Kaplan-Meier analysis of leukemia-free survival after HPC transplantation. HPCs all express NOTCH1-ICN and vector (black, n=13) or shNF1 (red, n=6), shBCL2L11 (orange, n=6), shPTEN (magenta, n=3), shFBWX7 (green, n=4), do-Ikzf1 (blue, n=10) or shPHF6 (violet, n=3). b. Cell number during in vitro culture of T-ALL1 cells expressing the indicated antagomirs (mean and SD for each time point; significant differences (p<0.05) at d6* and over the 6d period** are indicated) and quantitative RT-PCR measurement of miRNA expression in T-ALL1 cells (inset). c. Viability of T-ALL1 cells transduced with the indicated antagomirs (mean and SD, *p<0.05). d and e. Quantitative RT-PCR of BCL2L11 (d) and PTEN (e) mRNA levels in T-ALL1 cells expressing the indicated antagomirs (mean and SD, *p<0.05 compared to vector). f and g. 3'UTR luciferase reporter assays of BCL2L11 (f) and PTEN (g) in cells transduced with the indicated miRNAs (mean and SD, *p<0.05 in triplicate measurements). h. Diagrammatic summary of the overlapping regulation of six tumor suppressor genes by miRNAs identified in this study.

To ensure the physiological significance of these tumor suppressor genes, knockdown analysis was conducted using the same murine NOTCH1-induced T-ALL model. Briefly, shRNAs against PTEN (Mavrakis, et al., 2010), BCL2L11 (Mavrakis, et al., 2010), NF1, PHF6, and FBXW7 (FIG. 26) and a dominant negative IKZF1 allele (Dn-Ikzf1) (Beverly & Capobianco, 2003) were used in the same adoptive transfer model described above. These experiments confirmed acceleration of NOTCH1-triggered leukemia development by shRNAs against PTEN (n=3, p<0.05) and BCL2L11 (n=6, p<0.01) (Mavrakis, et al., 2010) as well as against NF1 (n=6, p<0.01), PHF6 (n=3, p<0.05), and Dn-Ikzf1 (n=10, p<0.01). FBXW7 showed a trend but did not reach significance (n=4, p=0.1) (FIG. 27a). While shRNAs and miRNAs may differ in their mechanism and possibly in their efficiency of target knockdown, these results indicate the tumor suppressive function of these genes in NOTCH1-triggered T-ALL.

Anti-Leukemic Activity of Antagomirs to the miRNAs Implicated in T-ALL

Given the pleiotropic and partially overlapping pattern of tumor suppressor gene regulation by multiple miRNAs, the effect of miRNA antagomirs on the growth rate and viability of two human T-ALL cell lines, T-ALL1 and Koptk1, were assessed. The human T-ALL1 cell line expresses high levels of miR-19a, miR-19b, miR-26a and miR-92 but only low levels of other miRNAs, e.g. miR-148a and the randomly chosen miR-182 (FIG. 27b inset). Antagomirs against miR-19a/b, miR-26a and miR-92 reduce growth rate (FIG. 27b), significantly decrease cell viability (p<0.05; each antagomir compared to vector) (FIG. 27c) and de-repress the tumor suppressor genes PTEN and BCL2L11 (FIGS. 27d and e). By contrast, the antagomirs against miR-148a and miR-182 showed no significant (p>0.05) effect on proliferation, viability or expression of PTEN or BCL2L11. Results in the Koptk1 cell line were analogous to those in the T-ALL1 cell line (FIG. 28). Similarly, antagomirs against miR-223 reduce cell proliferation in T-ALL1, Koptk1 and Jurkat T-ALL cell lines (FIG. 29). Hence, individual miRNAs make relevant contributions to and affect viability and tumor suppressor gene expression in T-ALL, and antagonists or antagomirs targeting these miRNAs are, therefore, expected to be useful agents in the treatment of patients with T-ALL.

miRNAS that Bind Common Target Genes Exhibit Cooperative Anti-Leukemic Effects

Co-expression of antagomirs against miR-19a/b, miR-26a and miR-92 had a stronger effect on the growth of T-ALL1 cells than the individual antagomirs (p<0.001 combined antagomirs vs. vector) (FIG. 27b). The effect on cell viability was even more pronounced, such that the three antagomirs produced twice as much apoptosis in a short-term assay as did individual antagomirs (FIG. 27c). Accordingly, the combined treatment produced larger increases in BCL2L11 and PTEN expression compared to the individual antagomirs (FIGS. 27d and e). Similarly, co-expression of miR19b and miR-92 or miR-19b, miR-26a and miR-92 produced additive effects on the BCL2L11 and PTEN 3'UTR reporter activity, respectively (FIGS. 27f and g). Thus, groups of highly expressed miRNAs produce cooperative effects in human T-ALL cells. Administration of antagonists or antagomirs targeting these groups of miRNAs is, therefore, expected to have additive or synergistic benefit in the treatment of patients with T-ALL.

Materials and Methods

T-ALL Patient Samples.

Diagnostic bone marrow samples of 50 T-ALL patients were obtained from different European centers (UZ Ghent, Ghent; UZ Leuven, Leuven; Hôpital Purpan, Toulouse; CHU de Nancy-Brabois, Vandoeuvre-Les-Nancy). The resulting T-ALL patient cohort consists of 15 TAL/LMO (seven LMO2 rearranged and eight SIL-TAL), twelve HOXA (four MLL rearranged, six inv(7)(p15q35) and two CALM-AF10), ten TLX3 and five TLX1 rearranged patient samples. The remaining eight T-ALL patients could not be categorized to a known T-ALL subgroup. Total RNA from the leukemic samples was isolated using the TRIzol reagent (Invitrogen, Belgium) as described previously (Van Vlierberghe, et al., 2006). This study (2008/531) was approved by the Medical Ethical Commission of Ghent University Hospital (Belgium).

T-ALL Cell Lines.

Eighteen T-ALL cell lines (DND-41, MOLT-16, CCRF-CEM, RPMI-8402, ALL-SIL, KE-37, BE-13, HSB-2, HPB-ALL, LOUCY, PF-382, PEER, MOLT-3, CUTLL1, CTV-1, P12-ICHIKAWA, T-ALL1 and KOPTK1) and the HEK-293T cell line were cultured in RPMI-1640 medium (Invitrogen, Belgium) supplemented with 15% fetal calf serum, 1% penicillin/streptomycin, 1% kanamycin and 1% glutamine. Total RNA from the leukemic cell lines was isolated using the miRNeasy Mini kit (Qiagen, Belgium) according to the manufacturer's protocol.

Subsets of Normal T-cell Populations.

Pediatric thymuses were obtained and used according to the guidelines of the Medical Ethical Commission of Ghent University Hospital (Belgium). Five subsets of normal T-cell populations (CD34$^+$, CD3$^-$CD4$^+$CD8$^+$, CD3$^+$CD4$^+$CD8$^+$, CD3$^+$CD4$^+$CD8$^-$ and CD3$^+$CD4$^-$CD8$^+$) were obtained by cell sorting on a FACSVantage fluorescence-activated cell sorter (FACS) using Cellquest software or by use of MACS and microbeads (Van de Walle, et al., 2009). CD34$^+$ thymocytes were obtained from the pediatric thymuses by using MACS with CD34 microbeads (Miltenyi Biotec). The double positive (DP) CD3$^-$CD4$^+$CD8$^+$ and CD3$^+$CD4$^+$CD8$^+$ T-cells were sorted by staining of total thymus suspension with CD3-fluorescein isothiocyanate (FITC), CD8-phycoerythrin (PE) and CD4-allophycocyanin (APC). To sort for single positive CD3$^+$CD4$^+$CD8$^-$ and CD3$^+$CD4$^-$CD8$^+$ T-cells, depletion of immature CD1$^+$ thymocytes was first performed by use of Dynabeads (Dynal Biotech), and the resulting population, enriched for more mature cells, was subsequently labeled with CD3-FITC, CD8-PE and CD4-APC. The purity of the different subsets of normal T-cell populations was always at least 98%. Total RNA was isolated using the miRNeasy mini kit (Qiagen, Belgium) according to the manufacturer's protocol.

MicroRNA Profiling.

High-throughput, real-time quantification of miRNAs was performed by use of stem-loop reverse transcriptase (RT) primers for miRNA cDNA synthesis followed by a pre-amplification step and Taqman PCR analysis (Applied Biosystems, Belgium) (Chen, et al., 2005). In brief, 20 ng of total RNA from leukemia patient samples, leukemic cell lines or normal T-cell subsets was reverse transcribed by use of the megaplex RT stem-loop primer pool for miRNA cDNA synthesis of 448 small RNAs including 430 miRNAs and 18 small RNA controls. Next, pre-amplification of cDNA was performed in a 14-cycle PCR reaction by use of Taqman PreAmp Master Mix (2x) and PreAmp Primer Mix (5x) (Applied Biosystems, Belgium) consisting of an miRNA-specific forward primer and a universal reverse primer (Mestdagh, et al., 2008). Finally, the 448 small RNAs were profiled for each sample using a 40-cycle PCR protocol. The real-time RT-PCR reactions were all performed on a 7900HT (Applied Biosystems, Belgium) using the gene maximization strategy (Hellemans, Mortier, De Paepe, Frank Speleman, & Jo Vandesompele, 2007). SDS software version 2.1 was used to calculate raw Cq values with automatic base line settings and a threshold of 0.05. We used the mean expression value of all expressed miRNAs in a given sample as a normalization factor for normalization of the quantitative PCR data; miRNAs with a Cq-value>35 were considered unexpressed (Mestdagh, et al., 2009).

Cell Culture, Viability, Proliferation Assays and Vector Constructs.

Figure 10:
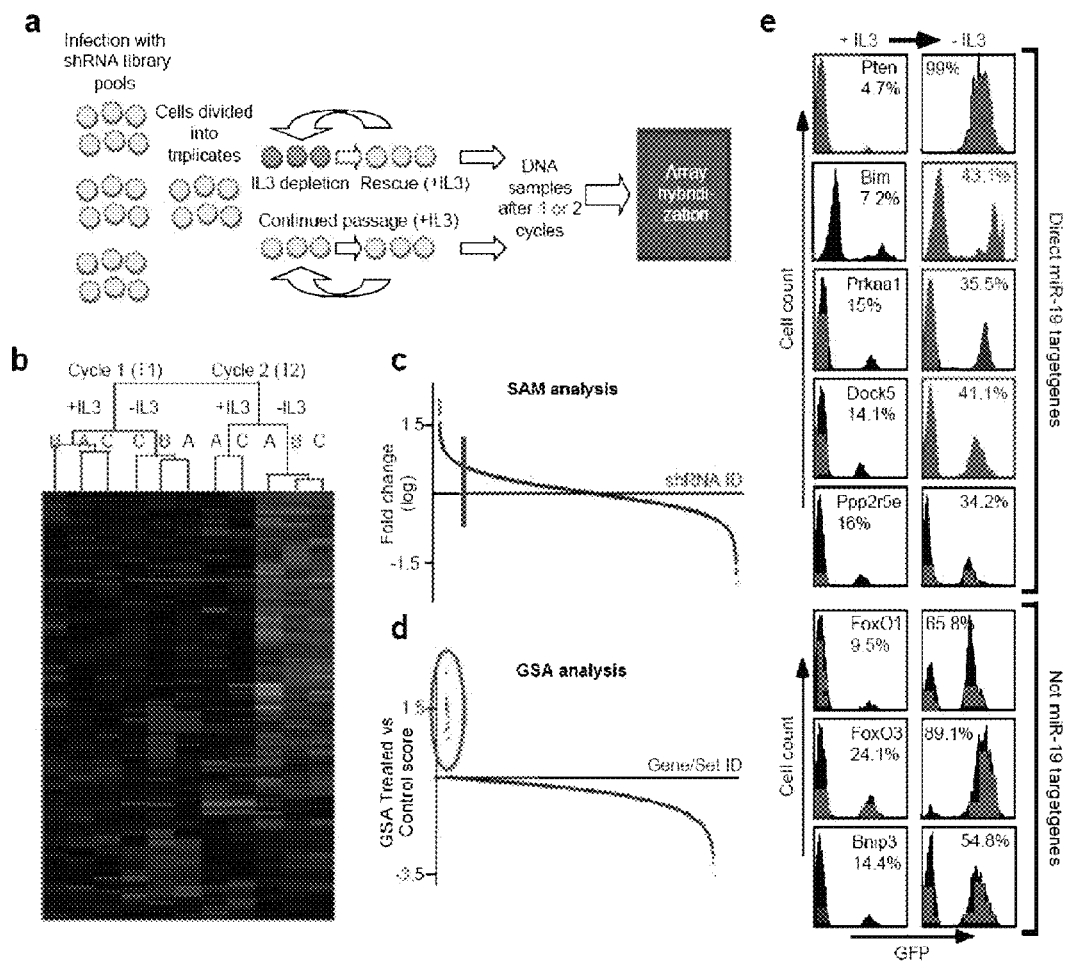
FIG. 10. Genetic screen for shRNAs that phenocopy miR-19 in lymphocyte survival. (a) Design schematic of the pooled shRNA screen. (b) Heat-map of the unsupervised clustering analysis of the half-hairpin array results. T1 and T2 indicate time points after 1 or 2 cycles of IL3 depletion; –IL3 and +IL3 indicate culture in the absence or presence of IL3; A, B and C indicate replicates (replicate B at T2/+IL3 was removed for technical reasons). (c) Statistical analysis of microarray data (SAM) indicating fold change (log 2) for individual shRNAs and the threshold for validation studies (red line). (d) Gene Set enrichment analysis (GSA) identifies enrichment of sets of shRNAs targeting 14 genes (red circle). (e) Representative validation experiments showing the enrichment of FL5-12 cells expressing the indicated shRNAs and GFP upon IL3 depletion. Five of the eight validated 'hits' are direct miR-19 targets. Vector alone showed no change (not shown).

FL5-12 murine pro B-lymphocytes, cell cycle and apoptosis studies and viral transductions were as described (Mavrakis, et al., 2008), (Plas, Talapatra, Edinger, Rathmell, & Thompson, 2001). T-ALL cell lines, including Jurkat, were cultured in RPMI 1640 medium supplemented with 10-20% fetal calf serum, 100 U/ml penicillin G and 100 μg/ml streptomycin at 37° C. in a humidified atmosphere under 5% $CO_2$. All vectors are based on murine stem cell virus (MSCV) and include the miRNA expression vector encoding all miRNAs described (He, et al., 2005), NOTCH1-ICN (Pear, et al., 1996) and the individual shRNA vectors (protein knockdown by shRNAs; FIG. 10). The miRNA pooled library (He, et al., 2005) is a generous gift from G. J. Hannon and has been expanded by PCR cloning to contain ~300 miRNAs. The antagomirs MZIP19a-PA-1, MZIP19b-PA-1, MZIP26a-PA-1, MZIP92a-PA-1, MZIP148a-PA-1, MZIP182-PA1, MZIP223-PA-1 and scrambled control (MZIP000-PA-1) were from System Biosciences.

Library Screens.

The primary screen is based on c-MYC-induced apoptosis in MEFs (Evan, et al., 1992). MEFs were transduced with c-MYC and the miRNA library and cultured in puromycin to select for homogeneous c-MYC expression; apoptosis was triggered by diluting serum from 10% to 0.1%. Surviving cells remained adherent and were collected for DNA isolation, PCR amplification of the integrated miRNA library constructs, sub-cloning into pGEM-T vector, bacterial transformation, and sequence identification of ~100 colonies. A secondary library was constructed by sub-cloning all miRNAs from the primary screen into an MSCV construct. The secondary screen is based on the IL-3 dependence of FL5-12 lymphocytes in vitro (Mavrakis, et al., 2010), (Plas, Talapatra, Edinger, Rathmell, & Thompson, 2001). FL5-12 cells were partially transduced with the pooled, GFP-tagged library and selected by IL-3 depletion. miRNAs were identified as above. Individual miRNAs were subsequently validated in the same FL5-12 assay and in vivo.

Generation of Mice.

The mouse T-ALL model has been reported (Pear, et al., 1996), (Wendel, et al., 2004). Data were analyzed in Kaplan-Meier format using the log-rank (Mantel-Cox) test for statistical significance. The surface marker analysis was as described (Wendel, et al., 2004).

Western Blot Analysis.

Immunoblots of whole cell lysates were performed as described (Wendel, et al., 2004). Antibodies were against Bim/Bcl2l11 (AAP-330, 1:1000, Assay Designs), Nf1 (sc67, 1:100, Santa Cruz), Cdc4/Fbxw7 (ab7405, 1:500, Abeam), Ikzf1 (sc-13039, 1:500, Santa Cruz), Phf6 (NB100-79861, 1:1000, Novus Biologicals), Pten (9559, 1:1000, Cell Signaling), tubulin (1:5000; Sigma, B-5-1-2) and actin (1:5000; Sigma, AC-15).

Real-Time Quantitative PCR for Gene Expression.

Total RNA and miRNA-enriched RNA was extracted using the Allprep DNA/RNA/Protein and miRNeasy Mini kits. Pathological diagnosis was by expert hematopathologists at Weill Cornell Medical Center. cDNA synthesis, PCR and analysis by the ΔΔ Ct method were as described (Mavrakis, et al., 2008) and utilized Taqman Gene Expression Assays: Bcl2l11 (Mm00437796_m1), BCL2L11 (Hs00197982_m1), Pten (Mm01212532_m1), PTEN (Hs02621230_s1), Nf1 (Mm00812430_m1), NF1 (Hs01035104_m1), Ikzf1 (Mm01187878_m1), IKZF1 (Hs00172991_m1), Fbxw7 (Mm00504452_m1), FBXW7 (Hs00217794_m1), Phf6 (Mm00804415_m1), and Mouse GAPD (GAPDH) (4352932, Applied Biosystems). Expression was normalized to RNU6B (001093, Applied Biosystems).

Computational Analyses of miRNA—Target Gene Interaction

Training Data.

A supervised learning approach was carried out to try to identify, in an unbiased way, a small set of target genes that could discriminate between miRNAs that passed all screens (+1 class) and those that did not pass (−1 class). While designed to identify a set of target genes common to the positive miRNAs, the approach may also identify genes that are commonly targeted by the negative miRNAs. The miRNAs validated through the screen (miR-19, miR-20/93, miR-25/92, miR-148, miR-26a, miR-223, miR-27ab) were used as positive training data (+1 class). Three miRNAs that failed to validate at the final stage (miR-30a, miR-23a, miR-24) as well as five additional miRNAs that are highly expressed in T-ALL but failed in the initial screen (miR-142-3p, miR-150, miR-342-3p, miR-146, miR-16) were used as negative training data (−1 class).

Target prediction. Using the seed sequence (position 2:8) for each miRNA, conserved mRNA targets were defined as those in which the complementary sequence occurs in the 3'UTRs of both the mouse and human orthologues. The minimum number of seed matches from both UTRs was used as the conserved 7 mer count for each miRNA:mRNA pair. Biopython was used to extract 3'UTR sequences for mouse and human using Refseq (Release 42). The longest 3'UTR was used when multiple RefSeq transcripts were present for a single gene.

Lasso Regression.

Lasso regression was used to identify gene sets that distinguish positive miRNAs from negative miRNAs. In this approach, each miRNA (positive or negative) is represented by its vector $x_{miR}$ of conserved 7 mer seed counts over all possible genes. The regression learns a weight vector w over genes such that the weighted sum of 7 mer seed counts for positive (resp. negative) miRNAs is close to +1 (resp. −1). The lasso constraint in the regression model encourages sparsity, i.e. most of the genes will have weight (regression coefficient) equal to 0. In this way, lasso regression identifies a smaller number of target genes that can discriminate between the two classes. Formally, the optimization problem is solved:

$$\min_w \sum_{miR} (y_{miR} - w \cdot x_{miR})^2 + \lambda \sum_g |w_g|$$

where $y_{miR}$ is +1 for validated miRNAs and −1 for non-validated miRNAs, $x_{miR}$ is the vector of conserved 7 mer counts and λ is the regularization parameter, which was given ten non-zero weights. Lasso regression was performed using the glmnet package from Bioconductor.

Enrichment of miRNAs.

The empirical p-value for enrichment of miRNAs in Table 3 was determined by selecting 10,000 random samples of genes (of size equal to the set of tumor suppressor genes) from the full list of human genes for which 3'UTRs and target predictions were available. The sum of scores was calculated for each miRNA family for each of these random gene sets. miRNA families were then ranked according to these scores, and enrichment scores for these rankings were determined by a Wilcoxon rank-sum test comparing the positive miRNAs (passed all screens) versus all other miRNAs. This procedure was repeated for (i) conserved seed match count and (ii) context scores from TargetScan using three different sets of miRNA seed families as defined by TargetScan: (a) all families; (b) conserved families; (c) broadly conserved families.

Analyses of miRNA—3'UTR Interactions.

Rank-order was determined based on a cumulative measure of site efficacy by summing the context scores of predicted binding sites for a given miRNA across the set of tumor suppressor genes using Targetscan 5.1 software (Lewis, Shih, Jones-Rhoades, Bartel, & Burge, 2003), (Friedman, Farh, Burge, & Bartel, 2009).

Luciferase Assays.

The mouse FBXW7 (bp 2793-4139; acc. no. NM_001177773), human NF1 (bp 10033-10666; acc. no NM_000267), human PHF6 (bp position 3271-4299; acc. no. NM_001015877) and Bim (bp. 3155-4773; acc. no. NM_009754) 3'UTR fragments were generated by PCR and cloned into the psi-CHECK-2 vector (Promega) with the exception of the IKZF1 3'UTR, which was purchased from Genecopoeia (cat no. HmiT000397b, by 2343-4471 of UTR). The assays were performed as described (Xiao, et al., 2008).

REFERENCES

Aifantis, I., Raetz, E., & Bu, S. (2008). Molecular Pathogenesis of T-cell Leukaemia and Lymphoma. *Nature Reviews Immunology,* 8, 380-390.

Balgobind, B. V., Van Vlierberghe, P., van den Ouweland, A. M., Beverloo, H. B., Terlouw-Kromosoeto, J. N., van Wering, E. R., et al. (2008). Leukemia-associated NF1 inactivation in patients with pediatric T-ALL and AML lacking evidence for neurofibromatosis. *Blood,* 11 (8), 4322-4328.

Bartel, D. P. (2004). MicroRNAs: Genomics, Biogenesis, Mechanism, and Function. *Cell,* 116, 281-297.

Chen, C., Ridzon, D. A., Broomer, A. J., Zhou, Z., Lee, D. H., Nguyen, J. T., et al. (2005). Real-time Quantification of microRNAs by Stem-loop RT-PCR. *Nucleic Acids Research,* 33 (20), e179.

Dail, M., Li, Q., McDaniel, A., Wong, J., Akagi, K., Huang, B., et al. (2010). Mutant Ikzf1, KrasG12D, and Notch1 cooperate in T lineage leukemogenesis and modulate responses to targeted agents. *Proceedings of the National Academy of Sciences USA,* 107 (11), 5106-5111.

Evan, G. I., Wyllie, A. H., Gilbert, C. S., Littlewood, T. D., Land, H., Brooks, M., et al. (1992). Induction of Apoptosis in Fibroblasts by c-myc Protein. *Cell,* 69 (1), 119-128.

Friedman, R. C., Farh, K. K.-H., Burge, C. B., & Bartel, D. P. (2009). Most Mammalian mRNAs Are Conserved Targets of microRNAs. *Genome Research,* 19 (1), 92-105.

He, L., Thomson, J. M., Hemann, M. T., Hernando-Monge, E., Mu, D., Goodson, S., et al. (2005). A MicroRNA Polycistron As a Potential Human Oncogene. *Nature,* 435 (7043), 828-833.

Hellemans, J., Mortier, G., De Paepe, A., Frank Speleman, F., & Jo Vandesompele, J. (2007). qBase Relative Quantification Framework and Software for Management and Automated Analysis of Real-time Quantitative PCR Data. *Genome Biology,* 8 (2), R19.

Kleppe, M., Lahortiga, I., El Chaar, T., De Keersmaecker, K., Mentens, N., Graux, C., et al. (2010). Deletion of the protein tyrosine phosphatase gene PTPN2 in T-cell acute lymphoblastic leukemia. *Nature Genetics,* 42 (6), 530-535.

Klinakis, A., Szabolcs, M., Politi, K., Kiaris, H., Artavanis-Tsakonas, S., & Efstratiadis, A. (2006). Myc is a Notch1 Transcriptional Target and a Requisite for Notch1-induced Mammary Ttumorigenesis in Mice. *Proceedings of the National Academy of Sciences USA,* 103 (24), 9262-9267.

Landais, S., Landry, S., Legault, P., & Rassart, E. (2007). Oncogenic Potential of the miR-106-363 Cluster and Its Implication in Human T-Cell Leukemia. *Cancer Research,* 67 (12), 5699-5707.

Landgraf, P., Rusu, M., Sheridan, R., Sewer, A., Iovino, N., Aravin, A., et al. (2007). A Mammalian microRNA Expression Atlas Based on Small RNA Library Sequencing. *Cell,* 129 (7), 1401-1414.

Lewis, B. P., Shih, I.-h., Jones-Rhoades, M. W., Bartel, D. P., & Burge, C. B. (2003). Prediction of Mammalian microRNA Targets. *Cell,* 115 (7), 787-798.

Li, Q.-J., Chau, J., Ebert, P. J., Sylvester, G., Min, H., Liu, G., et al. (2007). miR-181a Is an Intrinsic Modulator of T-cell Sensitivity and Selection. *Cell,* 129 (1), 147-161.

Lu, J., Getz, G., Miska, E. A., Alvarez-Saavedra, E., Lamb, J., Peck, D., et al. (2005). MicroRNA expression profiles classify human cancers. *Nature,* 435 (7043), 834-838.

Marçais, A., Jeannet, R., Hernandez, L., Soulier, J., Sigaux, F., Chan, S., et al. (2010). Genetic inactivation of Ikaros is a rare event in human T-ALL. *Leukemia Research,* 34 (4), 426-429.

Maser, R. S., Choudhury, B., Campbell, P. J., Feng, B., Wong, K.-K., Protopopov, A., et al. (2007). Chromosomally unstable mouse tumours have genomic alterations similar to diverse human cancers. *Nature,* 447 (7147), 966-971.

Mavrakis, K. J., Wolfe, A. L., Oricchio, E., Palomero, T., de Keersmaecker, K., McJunkin, K., et al. (2010). Genome-wide RNA-mediated Interference Screen Identifies miR-19 Targets in Notch-induced T-cell Acute Lymphoblastic Leukaemia. *Nature Cell Biology,* 12 (4), 372-379.

Mavrakis, K. J., Zhu, H., Silva, R. L., Mills, J. R., Teruya-Feldstein, J., Lowe, S. W., et al. (2008). Tumorigenic Activity and Therapeutic Inhibition of Rheb GTPase. *Genes & Development,* 22 (16), 2178-2188.

Mestdagh, P., Feys, T., Bernard, N., Guenther, S., Chen, C., Speleman, F., et al. (2008). High-throughput Stem-loop RT-qPCR miRNA Expression Profiling Using Minute Amounts of Input RNA. *Nucleic Acids Research,* 36 (21), e143.

Mestdagh, P., Van Vlierberghe, P., De Weer, A., Muth, D., Westermann, F., Speleman, F., et al. (2009). A Novel and Universal Method for microRNA RT-qPCR Data Normalization. *Genome Biology,* 10 (6), R64.

Mullighan, C. G., Goorha, S., Radtke, I., Miller, C. B., Coustan-Smith, E., Dalton, J. D., et al. (2007). Genome-wide analysis of genetic alterations in acute lymphoblastic leukaemia. *Nature,* 446 (7137), 758-764.

O'Neil, J., Grim, J., Strack, P., Rao, S., Tibbitts, D., Winter, C., et al. (2007). FBW7 Mutations in Leukemic Cells Mediate NOTCH Pathway Activation and Resistance to γ-Secretase Inhibitors. *The Journal of Experimental Medicine,* 204 (8), 1813-1824.

Palomero, T., Lim, W. K., Odom, D. T., Sulis, M. L., Real, P. J., Margolin, A., et al. (2006). NOTCH1 Directly Regulates c-MYC and Activates a Feed-forward-loop Transcriptional Network Promoting Leukemic Cell Growth. *Proceedings of the National Academy of Sciences USA,* 103 (48), 18261-18266.

Pear, W. S., Aster, J. C., Scott, M. L., Hasserjian, R. P., Soffer, B., Sklar, J., et al. (1996). Exclusive Development of T Cell Neoplasms in Mice Transplanted with Bone Marrow Expressing Activated Notch Alleles. *The Journal of Experimental Medicine,* 183 (5), 2283-2291.

Petrocca, F., Visone, R., Onelli, M. R., Shah, M. H., de Martino, I., Iliopoulos, D., et al. (2008). E2F1-regulated microRNAs Impair TGFb-Dependent Cell-cycle Arrest and Apoptosis in Gastric Cancer. *Cancer Cell,* 13, 272-286.

Plas, D. R., Talapatra, S., Edinger, A. L., Rathmell, J. C., & Thompson, C. B. (2001). Akt and Bcl-xL Promote Growth Factor-independent Survival Through Distinct Effects on Mitochondrial Physiology. *The Journal of Biological Chemistry,* 276 (15), 12041-12048.

Sun, L., Crotty, M.-L., Sensel, M., Sather, H., Navara, C., Nachman, J., et al. (1999). Expression of Dominant-Negative Ikaros Isoforms in T-Cell Acute Lymphoblastic Leukemia. *Clinical Cancer Research,* 5 (8), 2112-2120.

Thompson, B. J., Buonamici, S., Sulis, M. L., Palomero, T., Vilimas, T., Basso, G., et al. (2007). The SCFFBW7 ubiquitin ligase complex as a tumor suppressor in T cell leukemia. *The Journal of Experimental Medicine,* 204 (*), 1825-1835.

Van de Walle, I., De Smet, G., De Smedt, M., Vandekerckhove, B., Leclercq, G., Plum, J., et al. (2009). An early decrease in Notch activation is required for human TCR-αβ lineage differentiation at the expense of TCR-γδ T-cells. *Blood,* 113 (13), 2988-2998.

Van Vlierberghe, P., van Grotel, M., Beverloo, H. B., Lee, C., Helgason, T., Buijs-Gladdines, J., et al. (2006). The Cryptic Chromosomal Deletion del(11)(p12p13) as a New Activation Mechanism of LMO2 in Pediatric T-cell Acute Lymphoblastic Leukemia. *Blood,* 8 (10), 3520-3529.

Wendel, H. G., De Stanchina, E., Fridman, J. S., Malina, A., Ray, S., Kogan, S., et al. (2004). Survival Signalling by Akt and eIF4E in Oncogenesis and Cancer Therapy. *Nature,* 428 (6980), 332-337.

Weng, A. P., Ferrando, A. A., Lee, W., Morris, I. J., Silverman, L. P., Sanchez-Irizarry, C., et al. (2004). Activating Mutations of NOTCH1 in Human T Cell Acute Lymphoblastic Leukemia. *Science,* 306 (5694), 269-271.

Weng, A. P., Millholland, J. M., Yashiro-Ohtani, Y., Arcangeli, M. L., Lau, A., Wai, C., et al. (2006). c-Myc Is an Important Direct Target of Notch1 in T-cell Acute Lymphoblastic Leukemia/Lymphoma. *Genes & Development,* 20 (15), 2096-2109.

Winandy, S., Wu, P., & Georgopoulos, K. (1995). A dominant mutation in the Ikaros gene leads to rapid development of leukemia and lymphoma. *Cell,* 83 (2), 289-299.

Xiao, C., Srinivasan, L., Calado, D. P., Patterson, H. C., Zhang, B. W., Henderson, J. M., et al. (2008). Lymphoproliferative Disease and Autoimmunity in Mice with Increased miR-17-92 Expression in Lymphocytes. *Nature Immunology,* 9 (4), 405-414.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein. The summary, description, materials and methods and drawings are, accordingly, to be regarded in an illustrative rather than restrictive sense.

Various references, including patents and printed publications, are cited throughout this Specification, each of which is incorporated herein by reference in its entirety.

What is claimed is:

1. A pharmaceutical composition for use in treatment of a lymphoid malignancy consisting of a combination of an antagomir or RNA oligonucleotide which is complementary to miRNA miR-26 and an antagomir or RNA oligonucleotide which is complementary to miRNA miR-223, and a pharmaceutically acceptable carrier or diluent wherein the antagomir or RNA oligonucleotide specifically inhibits or blocks the expression or activity of the complementary miR-26 or miR-223 and wherein at least 90% of the corresponding antagomir or RNA oligonucleotide nucleotides are complementary to the miR-26 sequence SEQ ID NO:5 or the miR-223 sequence SEQ ID NO:10.

2. The pharmaceutical composition of claim 1 wherein said antagomir or oligonucleotide comprises at least one modified nucleotide.

3. A pharmaceutical composition for use in treatment of a lymphoid malignancy consisting of a combination of an antagomir or RNA oligonucleotide which is complementary to miRNA miR-26 and an antagomir or RNA oligonucleotide which is complementary to miRNA miR-223, and an antagomir or RNA oligonucleotide complementary to the miRNA miR-19, miR-92 or the combination thereof, and a pharmaceutically acceptable carrier or diluent wherein the antagomir or RNA oligonucleotide specifically inhibits or blocks the expression or activity of the complementary miR-26 or miR-223, and miR-19, mIR-92 or the combination thereof, and wherein at least 90% of the corresponding antagomir or RNA oligonucleotide nucleotides is complementary to the miR-26 sequence SEQ ID NO:5, the miR-223 sequence SEQ ID NO:10, and the miR-19 sequence SEQ ID NO: 1 or SEQ ID NO: 2 or the miR-92 sequence SEQ ID NO: 6 or SEQ ID NO: 7.

4. A pharmaceutical composition for use in treatment of a lymphoid malignancy comprising a therapeutically effective amount of a combination of an antagomir or RNA oligonucleotide complementary to miRNA miR-26, an antagomir or RNA oligonucleotide which is complementary to miRNA miR-223, and an antagomir or RNA oligonucleotide complementary to miRNA miR-148, wherein the antagomir or RNA oligonucleotide specifically inhibits or blocks the expression or activity of the complementary miR-26, miR-223 or miR-148 and wherein at least 90% of the corresponding antagomir or RNA oligonucleotide nucleotides are complementary to the miR-26 sequence SEQ ID NO:5, the miR-223 sequence SEQ ID NO:10 or the miR-148 sequence SEQ ID NO:8, and a pharmaceutically acceptable carrier or diluent.

5. The pharmaceutical composition of claim 4 which further comprises an antagomir or RNA oligonucleotide complementary to the miRNA miR-19, miR-92 or the combination thereof, wherein the antagomir or RNA oligonucleotide specifically inhibits or blocks the expression or activity of the complementary miR-19 or miR-92 and wherein at least 90% of the corresponding antagomir or RNA oligonucleotide nucleotide is complementary to the miR-19 sequence SEQ ID NO: 1 or SEQ ID NO: 2 or the miR-92 sequence SEQ ID NO: 6 or SEQ ID NO: 7.

6. A method of enhancing or increasing the expression of a tumor suppressor gene selected from Pten, Bim/Bcl2l11, Phf6, Ikzf1, Nf1 and Fbxw7 comprising contacting cells which are capable of expressing one or more of said tumor suppressor gene with the pharmaceutical composition of any of claim 1, 2, 3 or 4.

7. A method of treating or alleviating a lymphoid malignancy, wherein the lymphoid malignancy is selected from T-cell acute lymphoblastic leukemia (T-ALL), B-cell acute lymphoblastic leukemia (B-ALL), diffuse large B-cell lymphoma (DLBCL) and Burkitt's lymphoma, wherein the miR17~92 cluster is amplified or overexpressed comprising administering the pharmaceutical composition of any of claim 1, 2, 3 or 4.

* * * * *